US010406222B2

(12) United States Patent
Kyratsous et al.

(10) Patent No.: US 10,406,222 B2
(45) Date of Patent: *Sep. 10, 2019

(54) HUMAN ANTIBODIES TO MIDDLE EAST RESPIRATORY SYNDROME—CORONAVIRUS SPIKE PROTEIN

(71) Applicant: Regeneron Pharmaceuticals, Inc., Tarrytown, NY (US)

(72) Inventors: Christos Kyratsous, Irvington, NY (US); Neil Stahl, Carmel, NY (US); Sumathi Sivapalasingam, Brooklyn, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/633,589

(22) Filed: Jun. 26, 2017

(65) Prior Publication Data

US 2017/0340728 A1 Nov. 30, 2017

Related U.S. Application Data

(63) Continuation of application No. 14/717,760, filed on May 20, 2015, now Pat. No. 9,718,872.

(60) Provisional application No. 62/072,716, filed on Oct. 30, 2014, provisional application No. 62/051,717, filed on Sep. 17, 2014, provisional application No. 62/004,971, filed on May 30, 2014, provisional application No. 62/002,233, filed on May 23, 2014.

(51) Int. Cl.

| | | |
|---|---|---|
| *A61K 39/215* | (2006.01) | |
| *C07K 16/10* | (2006.01) | |
| *A61K 45/06* | (2006.01) | |
| *A61K 39/12* | (2006.01) | |
| *C07K 14/165* | (2006.01) | |
| *G01N 33/569* | (2006.01) | |
| *A61K 39/00* | (2006.01) | |
| *A61K 38/00* | (2006.01) | |
| *C12N 7/00* | (2006.01) | |

(52) U.S. Cl.
CPC ............ *A61K 39/215* (2013.01); *A61K 39/12* (2013.01); *A61K 45/06* (2013.01); *C07K 14/165* (2013.01); *C07K 16/10* (2013.01); *G01N 33/569* (2013.01); *A61K 38/00* (2013.01); *A61K 2039/505* (2013.01); *C07K 2317/21* (2013.01); *C07K 2317/76* (2013.01); *C07K 2317/92* (2013.01); *C12N 7/00* (2013.01); *C12N 2770/20022* (2013.01); *C12N 2770/20034* (2013.01)

(58) Field of Classification Search
CPC ............... A61K 2300/00; A61K 39/12; A61K 2039/525; A61K 2039/6056; A61K 39/215; A61K 45/06; A61K 38/00; A61K 2039/505; C12N 7/00; C12N 15/86; C12N 2770/20022; C12N 2770/20034; C07K 14/005; C07K 14/70503; C07K 2317/31; C07K 2317/33; C07K 14/165; C07K 39/12; C07K 16/10; C07K 2317/92; C07K 2317/76; C07K 2317/21; G01N 33/569

See application file for complete search history.

(56) References Cited

U.S. PATENT DOCUMENTS

| | | |
|---|---|---|
| 7,750,123 B2 | 7/2010 | Marasco et al. |
| 9,718,872 B2 | 8/2017 | Kyratsous |
| 2006/0257852 A1* | 11/2006 | Rappuoli ............. A61K 39/215 435/5 |
| 2015/0275183 A1 | 10/2015 | Haagmans et al. |
| 2015/0351372 A1 | 12/2015 | Kyratsous et al. |
| 2016/0007579 A1 | 1/2016 | Kyratsous et al. |

FOREIGN PATENT DOCUMENTS

| | | |
|---|---|---|
| WO | WO 2014/045254 | 3/2014 |
| WO | WO 2015/179535 | 11/2015 |

OTHER PUBLICATIONS

Kyratsous CA, Olson W, Stahl N. Reply to Dimitrov et al.: VelociSuite technologies are a foundation for rapid therapeutic antibody development. Proc Natl Acad Sci U S A. Sep. 15, 2015;112(37):E5116. Epub Aug. 28, 2015.*

Dimitrov DS, Jiang S, Ying T, Tseng CT, Zhang L, Yuen KY. No evidence for a superior platform to develop therapeutic antibodies rapidly in response to MERS-CoV and other emerging viruses. Proc Natl Acad Sci U S A. Sep. 15, 2015;112(37):E5115. doi: 10.1073/pnas.1513441112. Epub Aug. 28, 2015.*

(Continued)

*Primary Examiner* — Rachel B Gill
(74) *Attorney, Agent, or Firm* — Adsero IP

(57) ABSTRACT

The present invention provides monoclonal antibodies that bind to the Middle East Respiratory Syndrome-Coronavirus (MERS-CoV) spike protein, and methods of use. In various embodiments of the invention, the antibodies are fully human antibodies that bind to MERS-CoV spike protein. In some embodiments, the antibodies of the invention are useful for inhibiting or neutralizing MERS-CoV activity, thus providing a means of treating or preventing MERS infection in humans. In some embodiments, the invention provides for a combination of one or more antibodies that bind to the MERS-CoV spike protein for use in treating MERS infection. In certain embodiments, the one or more antibodies bind to distinct non-competing epitopes comprised in the receptor binding domain of the MERS-CoV spike protein.

11 Claims, 14 Drawing Sheets

Specification includes a Sequence Listing.

(56) References Cited

OTHER PUBLICATIONS

Bowie et al. (1990) Science 247(4948):1306-10 "Deciphering the message in protein sequences: tolerance to amino acid substitutions".

Chan et al. (2012) J Infect 65(6):477-489 "Is the discovery of the novel human betacoronavirus 2c EMC/2012 (HCoV-EMC) the beginning of another SARS-like pandemic?"

Corman et al. (2012) Eurosurveillance 17(49) "Assays for laboratory confirmation of novel human coronavirus (hCoV-EMC) infections".

Corti et al. (2015) PNAS "Prophylactic and postexposure efficacy of a potent human monoclonal antibody against MERS coronavirus".

Coughlin and Prabhakar (2012) Reviews in Medical Virology 22(1):2-17. Epub Sep. 8, 2011. "Neutralizing human momoclonal antibodies to severe acute respiratory syndrome coronavirus: target, mechanism of action, and therapeutic potential" http://onlinelibrary.wiley.com/doi/10.1002/rmv.706/pdf.

Du et al. (2013) Journal of Virology 87(17):9939-9942 "Identification of a Receptor-Binding Domain in the S Protein of the Novel Human Coronavirus Middle East Respiratory Syndrome Coronavirus as an Essential Target for Vaccine Develolpment".

Du et al. (2013) PLOS ONE 8(12) "A Truncated Receptor-Binding Domain of MERS-CoV Spike Protein Potently Inhibits Mers-CoV Infection and Induces Strong Neutralizing Antibody Responses: Implication for Developing Therapeutics and Vaccines".

Gierer et al. (2013) Journal of Virology 87(10):5502-5511 "The Spike Protein of the Emerging Betacoronavirus EMC Uses a Novel Coronavirus Receptor for Entry, Can Be Activated by TMPRSS2, and Is Targeted by Neutralizing Antibodies".

Jiang et al. (2014) Science Translational Medicine 6(234) "Potent Neutralization of MERS-CoV by Human Neutralizing Monoclonal Antibodies to the Viral Spike Glycoprotein".

Lu et al. (2013) Nature 500:227-232 "Molecular basis of binding between novel human coronavirus MERS-CoV and its receptor CD26".

Mou et al. (2013) Journal of Virology 87(16):9379-9383 "The Receptor Binding Domain of the New Middle East Respiratory Syndrome Coronavirus Maps to a 231-Residue Region in the Spike Protein That Efficiently Elicits Neutralizing Antibodies".

Muller et al. (2012) Mbio. 3(6) Pii: e00515-12 "Human coronavirus EMC does not require the SARS-coronavirus receptor and maintains broad replicative capability in mammalian cell lines".

Murphy et al. (2014) Proc. Natl. Acad. Sci. USA 111(14):5153-5158 "Mice with megabase humanization of their immunoglobulin genes generate antibodies as efficiently as normal mice".

Pascal et al. (2015) PNAS 112(28) "Pre- and postexposure efficacy of fully human antibodies against Spike protein in a novel humanized mouse model of MERS-CoV infection".

Raj et al. (2013) Nature 495:251-256 "Dipeptidyl peptidase 4 is a functional receptor for the emerging human coronavirus-EMC".

SinoBiological.com (Jun. 15, 2012) MERS-Cov (NCoV/Novel coronavirus) Spike Antibody, Mouse Mab. Cat. # 40070-MM04; [Online] Available Website: http://www.sinobiologicalcdn.com/reagent/40070-R723.pdf; Last Update: unknown; Accessed on: Apr. 4, 2017.

SinoBiological.com (Jun. 15, 2012) MERS-Cov (NCoV/Novel coronavirus) Spike Antibody, Rabbit Mab. Cat. # 40069-R723; [Online] Available Website: http://www.sinobiologicalcdn.com/reagent/40069-R723.pdf; Last Update: unknown; Accessed on Apr. 4, 2017.

Tang and Marasco (2015) Immunotherapy 7(6):591-594 "Human neutralizing antibodies against MERS coronavirus: implications for future immunotherapy".

Tang et al. (2014) PNAS 111(19):2022-2024 "Identification of human neutralizing antibodies against MERS-CoV and their role in virus adaptive evolution".

Van Boheemen et al. (2012) GenBank Acc. No. AFS88936.1 Dec. 4, 2012 "S protein [Human betacoronavirus 2c EMC/2012]".

Van Boheemen et al. (2012) MBio. 3(6):e00473-12 "Genomic characterization of a newly discovered coronavirus associated with acute respiratory distress syndrome in humans".

Ying et al. (2015) Microbes Infect. 17(2):142-8, Epub Nov. 29, 2014 "Development of human neutralizing monoclonal antibodies for prevention and therapy of MERS-CoV Infections".

Ying et al. (2014) Journal of Virology 88(14):7796-7805 "Exceptionally Potent Neutralization of Middle East Respiratory Syndrome Coronavirus by Human Monoclonal Antibodies".

Zaki et al. (2012) The New England Journal of Medicine 367(19):1814-1820 "Isolation of a Novel Coronavirus from a Man with Pneumonia in Saudi Arabia".

Reusken (2013) The Lancet 13(10); 859-86 "Middle East Respiratory Syndrome Coronavirus neutralising serum antibodies in dromedary camels: a comparative serological study" doi: 10.1016/S1473-3099(13)70164-6. Epub Aug. 9, 2013.

\* cited by examiner

| Sample ID | ELISA Binding | ELISA Blocking | % Neutralization (.025 μg/ml) | Neutralization IC50 (M) | KD (M) | t½ (min) |
|---|---|---|---|---|---|---|
| HBVX06H05 | 2.676 | 99.7 | 99% | 1.328E-10 | 1.72E-09 | 11.1 |
| HBVX11H04 | 2.623 | 99.7 | 99% | 1.492E-10 | 3.28E-10 | 94.1 |
| HBVX11D02 | 2.420 | 97.8 | 98% | 2.108E-10 | 2.05E-09 | 13.5 |
| HBVZ10E10 | 2.537 | 90.8 | 98% | 4.636E-10 | 2.77E-09 | 10.4 |
| HBVY09F08 | 2.044 | 99.3 | 98% | 3.245E-10 | 1.79E-09 | 17.3 |
| HBVZ05G02 | 2.515 | 92.7 | 97% | 2.212E-10 | 2.72E-09 | 9.5 |
| HBVZ09B06 | 2.751 | 100.2 | 97% | 1.759E-10 | 6.53E-09 | 7.4 |
| HBVY01F08 | 2.182 | 99.0 | 97% | 1.377E-10 | 2.66E-10 | 96.0 |
| HBVY10G02 | 2.587 | 100.1 | 97% | 2.737E-10 | 3.73E-09 | 7.7 |
| HBVY04B06 | 2.463 | 100.1 | 96% | 6.845E-11 | 1.51E-09 | 13.3 |
| HBVY07D10 | 2.417 | 25.9 | 40% | 1.02E-09 | 9.39E-09 | 29.5 |
| HBVZ08A09 | 2.782 | 100.1 | 91% | 3.567E-10 | 5.93E-10 | 67.8 |
| HBVZ05G04 | 2.675 | 99.8 | 90% | 3.054E-10 | 4.77E-10 | ≥ 115 |
| HBVY06C07 | 2.508 | 90.9 | 89% | 5.56E-10 | 3.94E-10 | ≥ 115 |
| HBVY03H06 | 2.735 | 97.6 | 89% | 4.253E-10 | 6.69E-10 | ≥ 115 |
| HBVZ10G06 | 2.383 | 98.7 | 86% | 4.357E-10 | 4.72E-10 | ≥ 115 |
| HBVZ04F10 | 2.756 | 96.3 | 83% | 5.843E-10 | 7.78E-10 | 80.7 |
| HBVX11E09 | 2.533 | 100.3 | 5% | 3.587E-09 | 2.45E-10 | ≥ 115 |
| HBVY06H09 | 2.806 | 7.4 | 2% | - | 7.12E-09 | 18.8 |
| HBVZ05B11 | 2.677 | 2.6 | -6% | - | 2.97E-09 | 94.8 |
| HBVY02E05 | 2.644 | 74.4 | -10% | - | 2.15E-08 | 13.3 |
| HBVZ04C07 | 2.405 | 14.8 | 40% | 1.534E-09 | IC | IC |

Figure 2

Figure 3 ary application Ser.

SEQUENCE LISTING

```
<160> NUMBER OF SEQ ID NOS: 458

<210> SEQ ID NO 1
<211> LENGTH: 354
<212> TYPE: DNA
<213> ORGANISM: Artificial Sequence
<220> FEATURE:
<223> OTHER INFORMATION: synthetic

<400> SEQUENCE: 1
gaggtgcagc tggtggagtc tgggggaggc ttggttcagc ctggggggtc cctgagactc      60
tcctgttcag cctctggatt caccttagc agctatgaca tgagctgggt ccgccaggct     120
ccagggaagg ggctggagtg ggtctcagct attcgtggta gtggtcatac cacatactac     180
```

```
gcagactccg tgaagggccg gttcaccatc tccagagaca attccaagaa cacgttgtat      240
ctggaaatga acagcctgag agccgaggac acggccgtat attattgtgt gaaagatggg      300
agtatcgtag gttcgaccc ctggggccag ggaaccctgg tcaccgtctc ctca            354
```

<210> SEQ ID NO 2
<211> LENGTH: 118
<212> TYPE: PRT
<213> ORGANISM: Artificial Sequence
<220> FEATURE:
<223> OTHER INFORMATION: synthetic

<400> SEQUENCE: 2

```
Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Arg Gly Ser Gly His Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Glu Met Asn Ser Leu Arg Ala Glu Asp Thr Ala Val Tyr Tyr Cys
                85                  90                  95

Val Lys Asp Gly Ser Ile Val Gly Phe Asp Pro Trp Gly Gln Gly Thr
            100                 105                 110

Leu Val Thr Val Ser Ser
        115
```

<210> SEQ ID NO 3
<211> LENGTH: 24
<212> TYPE: DNA
<213> ORGANISM: Artificial Sequence
<220> FEATURE:
<223> OTHER INFORMATION: synthetic

<400> SEQUENCE: 3

```
ggattcacct ttagcagcta tgac                                             24
```

<210> SEQ ID NO 4
<211> LENGTH: 8
<212> TYPE: PRT
<213> ORGANISM: Artificial Sequence
<220> FEATURE:
<223> OTHER INFORMATION: synthetic

<400> SEQUENCE: 4

```
Gly Phe Thr Phe Ser Ser Tyr Asp
1               5
```

<210> SEQ ID NO 5
<211> LENGTH: 24
<212> TYPE: DNA
<213> ORGANISM: Artificial Sequence
<220> FEATURE:
<223> OTHER INFORMATION: synthetic

<400> SEQUENCE: 5

```
attcgtggta gtggtcatac caca                                             24
```

<210> SEQ ID NO 6
<211> LENGTH: 8
<212> TYPE: PRT
<213> ORGANISM: Artificial Sequence
<220> FEATURE:
<223> OTHER INFORMATION: synthetic

<400> SEQUENCE: 6

Ile Arg Gly Ser Gly His Thr Thr
1               5

<210> SEQ ID NO 7
<211> LENGTH: 33
<212> TYPE: DNA
<213> ORGANISM: Artificial Sequence
<220> FEATURE:
<223> OTHER INFORMATION: synthetic

<400> SEQUENCE: 7
gtgaaagatg ggagtatcgt agggttcgac ccc                           33

<210> SEQ ID NO 8
<211> LENGTH: 11
<212> TYPE: PRT
<213> ORGANISM: Artificial Sequence
<220> FEATURE:
<223> OTHER INFORMATION: synthetic

<400> SEQUENCE: 8

Val Lys Asp Gly Ser Ile Val Gly Phe Asp Pro
1               5                   10

<210> SEQ ID NO 9
<211> LENGTH: 321
<212> TYPE: DNA
<213> ORGANISM: Artificial Sequence
<220> FEATURE:
<223> OTHER INFORMATION: synthetic

<400> SEQUENCE: 9
gacatccaga tgacccagtc tccttccacc ctgtctgcat ctgtaggaga cagagtcacc    60
atcacttgcc gggccagtca gactattagt agctggttgg cctggtatca gcagaaacca   120
gggaaagccc ctaagctcct gatctataag gcgtctagtt tagaaagtgg ggtcccatca   180
aggttcagcg gcagtggatc tgggacagaa ttcactctca ccatcagcag cctgcagcct   240
gatgattttg caacttatta ctgccaacag tataatagtt attcgtacac ttttggccag   300
gggaccaagc tggagatcaa a                                            321

<210> SEQ ID NO 10
<211> LENGTH: 107
<212> TYPE: PRT
<213> ORGANISM: Artificial Sequence
<220> FEATURE:
<223> OTHER INFORMATION: synthetic

<400> SEQUENCE: 10

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Thr Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly

```
                    50                  55                  60
Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Ser Tyr Ser Tyr
                 85                  90                  95

Thr Phe Gly Gln Gly Thr Lys Leu Glu Ile Lys
            100                 105
```

```
<210> SEQ ID NO 11
<211> LENGTH: 18
<212> TYPE: DNA
<213> ORGANISM: Artificial Sequence
<220> FEATURE:
<223> OTHER INFORMATION: synthetic

<400> SEQUENCE: 11
cagactatta gtagctgg                                              18

<210> SEQ ID NO 12
<211> LENGTH: 6
<212> TYPE: PRT
<213> ORGANISM: Artificial Sequence
<220> FEATURE:
<223> OTHER INFORMATION: synthetic

<400> SEQUENCE: 12

Gln Thr Ile Ser Ser Trp
 1               5

<210> SEQ ID NO 13
<211> LENGTH: 9
<212> TYPE: DNA
<213> ORGANISM: Artificial Sequence
<220> FEATURE:
<223> OTHER INFORMATION: synthetic

<400> SEQUENCE: 13 aaggcgtct                                                         9

<210> SEQ ID NO 14
<211> LENGTH: 3
<212> TYPE: PRT
<213> ORGANISM: Artificial Sequence
<220> FEATURE:
<223> OTHER INFORMATION: synthetic

<400> SEQUENCE: 14

Lys Ala Ser
 1

<210> SEQ ID NO 15
<211> LENGTH: 27
<212> TYPE: DNA
<213> ORGANISM: Artificial Sequence
<220> FEATURE:
<223> OTHER INFORMATION: synthetic

<400> SEQUENCE: 15
caacagtata atagttattc gtacact                                    27

<210> SEQ ID NO 16
<211> LENGTH: 9
<212> TYPE: PRT
<213> ORGANISM: Artificial Sequence
<220> FEATURE:
```

<223> OTHER INFORMATION: synthetic

<400> SEQUENCE: 16

Gln Gln Tyr Asn Ser Tyr Ser Tyr Thr
1               5

<210> SEQ ID NO 17
<211> LENGTH: 375
<212> TYPE: DNA
<213> ORGANISM: Artificial Sequence
<220> FEATURE:
<223> OTHER INFORMATION: synthetic

<400> SEQUENCE: 17
caggtgcagc tggtgcagtc tggggctgag gtgaagaagc ctgggtcctc ggtgaaggtc      60
tcctgcaagg cttctggagg ctccttcagc gtctatgcta tcagctgggt gcgccaggcc     120
cctggacaag ggcttgagtg gatgggaggg atcatcccaa tctttggtac agcaaactac     180
gcacagaagt tccaggacag attcacgatt accacggacg aatccacgag cacagcctac     240
atggagctga gcagcctgag atctgaggac acggccatgt attactgtgc gagagagggg     300
gatattgtag tactaccagc tggtaagggg ggtatggacg tctggggcca agggaccacg     360
gtcaccgtct cctca                                                      375

<210> SEQ ID NO 18
<211> LENGTH: 125
<212> TYPE: PRT
<213> ORGANISM: Artificial Sequence
<220> FEATURE:
<223> OTHER INFORMATION: synthetic

<400> SEQUENCE: 18

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ser Phe Ser Val Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Asp Arg Phe Thr Ile Thr Thr Asp Glu Ser Thr Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Glu Gly Asp Ile Val Val Leu Pro Ala Gly Lys Gly Gly Met
            100                 105                 110

Asp Val Trp Gly Gln Gly Thr Thr Val Thr Val Ser Ser
        115                 120                 125

<210> SEQ ID NO 19
<211> LENGTH: 24
<212> TYPE: DNA
<213> ORGANISM: Artificial Sequence
<220> FEATURE:
<223> OTHER INFORMATION: synthetic

<400> SEQUENCE: 19
ggaggctcct tcagcgtcta tgct                                            24

<210> SEQ ID NO 20

<211> LENGTH: 8
<212> TYPE: PRT
<213> ORGANISM: Artificial Sequence
<220> FEATURE:
<223> OTHER INFORMATION: synthetic

<400> SEQUENCE: 20

Gly Gly Ser Phe Ser Val Tyr Ala
1               5

<210> SEQ ID NO 21
<211> LENGTH: 24
<212> TYPE: DNA
<213> ORGANISM: Artificial Sequence
<220> FEATURE:
<223> OTHER INFORMATION: synthetic

<400> SEQUENCE: 21
atcatcccaa tctttggtac agca                                              24

<210> SEQ ID NO 22
<211> LENGTH: 8
<212> TYPE: PRT
<213> ORGANISM: Artificial Sequence
<220> FEATURE:
<223> OTHER INFORMATION: synthetic

<400> SEQUENCE: 22

Ile Ile Pro Ile Phe Gly Thr Ala
1               5

<210> SEQ ID NO 23
<211> LENGTH: 54
<212> TYPE: DNA
<213> ORGANISM: Artificial Sequence
<220> FEATURE:
<223> OTHER INFORMATION: synthetic

<400> SEQUENCE: 23
gcgagagagg gggatattgt agtactacca gctggtaagg ggggtatgga cgtc            54

<210> SEQ ID NO 24
<211> LENGTH: 18
<212> TYPE: PRT
<213> ORGANISM: Artificial Sequence
<220> FEATURE:
<223> OTHER INFORMATION: synthetic

<400> SEQUENCE: 24

Ala Arg Glu Gly Asp Ile Val Val Leu Pro Ala Gly Lys Gly Gly Met
1               5                   10                  15

Asp Val

<210> SEQ ID NO 25
<211> LENGTH: 336
<212> TYPE: DNA
<213> ORGANISM: Artificial Sequence
<220> FEATURE:
<223> OTHER INFORMATION: synthetic

<400> SEQUENCE: 25
gatattgtga tgactcagtc tccactctcc ctgcccgtca cccctggaga gccggcctcc      60
atctcctgca ggtctagtca gagcctcctg catggtaatg gatacaacta tttggattgg    120
tacctgcaga agccagggca gtctccacag ctcctgatct atttggtttc tcatcgggcc    180

```
tccggggtcc ctgacaggtt cagtggcagt ggatcaggca cagatttttac actgaaaatc      240 agcagagtgg aggctgagga tgttggggtt tattactgca tgcaagctct acaaagtcct      300
tggacgttcg gccaagggac caaggtggaa atcaaa                                336
```

```
<210> SEQ ID NO 26
<211> LENGTH: 112
<212> TYPE: PRT
<213> ORGANISM: Artificial Sequence
<220> FEATURE:
<223> OTHER INFORMATION: synthetic

<400> SEQUENCE: 26
```

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Gly
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Val Ser His Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Ser Pro Trp Thr Phe Gly Gln Gly Thr Lys Val Glu Ile Lys
            100                 105                 110
```

```
<210> SEQ ID NO 27
<211> LENGTH: 33
<212> TYPE: DNA
<213> ORGANISM: Artificial Sequence
<220> FEATURE:
<223> OTHER INFORMATION: synthetic

<400> SEQUENCE: 27
cagagcctcc tgcatggtaa tggatacaac tat                                    33
```

```
<210> SEQ ID NO 28
<211> LENGTH: 11
<212> TYPE: PRT
<213> ORGANISM: Artificial Sequence
<220> FEATURE:
<223> OTHER INFORMATION: synthetic

<400> SEQUENCE: 28
```

```
Gln Ser Leu Leu His Gly Asn Gly Tyr Asn Tyr
1               5                   10
```

```
<210> SEQ ID NO 29
<211> LENGTH: 9
<212> TYPE: DNA
<213> ORGANISM: Artificial Sequence
<220> FEATURE:
<223> OTHER INFORMATION: synthetic

<400> SEQUENCE: 29 ttggtttct                                                                9
```

```
<210> SEQ ID NO 30
<211> LENGTH: 3
<212> TYPE: PRT
<213> ORGANISM: Artificial Sequence
```

<220> FEATURE:
<223> OTHER INFORMATION: synthetic

<400> SEQUENCE: 30

Leu Val Ser
1

<210> SEQ ID NO 31
<211> LENGTH: 27
<212> TYPE: DNA
<213> ORGANISM: Artificial Sequence
<220> FEATURE:
<223> OTHER INFORMATION: synthetic

<400> SEQUENCE: 31
atgcaagctc tacaaagtcc ttggacg                                            27

<210> SEQ ID NO 32
<211> LENGTH: 9
<212> TYPE: PRT
<213> ORGANISM: Artificial Sequence
<220> FEATURE:
<223> OTHER INFORMATION: synthetic

<400> SEQUENCE: 32

Met Gln Ala Leu Gln Ser Pro Trp Thr
1               5

<210> SEQ ID NO 33
<211> LENGTH: 354
<212> TYPE: DNA
<213> ORGANISM: Artificial Sequence
<220> FEATURE:
<223> OTHER INFORMATION: synthetic

<400> SEQUENCE: 33
gaggtgcagc tggtggagtc tgggggagac ttggtacagc cggggggtc cctgagagtc          60
tcctgtgcag cctctggatt caccttagc aactatgaca tgtactgggt ccgccaggct         120
ccagggaagg gctggagtg gtctcagtt attagtggta ttggtgctac cacatattac         180
gcagactccg tgaagggccg gttccacata tccagagaca attccaagaa cacggtgttt         240
ctgcaaatga atagtctgag agccgaggac acggccgtat attactgtgt gaagggggga         300
cctatagtgg ctacggatta ctgggggccag ggaaccctgg tcaccgtctc ctca              354

<210> SEQ ID NO 34
<211> LENGTH: 118
<212> TYPE: PRT
<213> ORGANISM: Artificial Sequence
<220> FEATURE:
<223> OTHER INFORMATION: synthetic

<400> SEQUENCE: 34

Glu Val Gln Leu Val Glu Ser Gly Gly Asp Leu Val Gln Pro Gly Gly
1               5                   10                  15

Ser Leu Arg Val Ser Cys Ala Ala Ser Gly Phe Thr Phe Ser Asn Tyr
            20                  25                  30

Asp Met Tyr Trp Val Arg Gln Ala Pro Gly Lys Gly Leu Glu Trp Val
        35                  40                  45

Ser Val Ile Ser Gly Ile Gly Ala Thr Thr Tyr Tyr Ala Asp Ser Val
    50                  55                  60

Lys Gly Arg Phe Thr Ile Ser Arg Asp Asn Ser Lys Asn Thr Val Phe
65                  70                  75                  80

```
Leu Gln Met Asn Ser Leu Arg Ala Glu Asp Thr Ala Val Tyr Tyr Cys
                 85                  90                  95

Val Lys Gly Gly Pro Ile Val Ala Thr Asp Tyr Trp Gly Gln Gly Thr
            100                 105                 110

Leu Val Thr Val Ser Ser
        115

<210> SEQ ID NO 35
<211> LENGTH: 24
<212> TYPE: DNA
<213> ORGANISM: Artificial Sequence
<220> FEATURE:
<223> OTHER INFORMATION: synthetic

<400> SEQUENCE: 35
ggattcacct ttagcaacta tgac                                          24

<210> SEQ ID NO 36
<211> LENGTH: 8
<212> TYPE: PRT
<213> ORGANISM: Artificial Sequence
<220> FEATURE:
<223> OTHER INFORMATION: synthetic

<400> SEQUENCE: 36

Gly Phe Thr Phe Ser Asn Tyr Asp
1               5

<210> SEQ ID NO 37
<211> LENGTH: 24
<212> TYPE: DNA
<213> ORGANISM: Artificial Sequence
<220> FEATURE:
<223> OTHER INFORMATION: synthetic

<400> SEQUENCE: 37
attagtggta ttggtgctac caca                                          24

<210> SEQ ID NO 38
<211> LENGTH: 8
<212> TYPE: PRT
<213> ORGANISM: Artificial Sequence
<220> FEATURE:
<223> OTHER INFORMATION: synthetic

<400> SEQUENCE: 38

Ile Ser Gly Ile Gly Ala Thr Thr
1               5

<210> SEQ ID NO 39
<211> LENGTH: 33
<212> TYPE: DNA
<213> ORGANISM: Artificial Sequence
<220> FEATURE:
<223> OTHER INFORMATION: synthetic

<400> SEQUENCE: 39
gtgaaagggg gacctatagt ggctacggat tac                                33

<210> SEQ ID NO 40
<211> LENGTH: 11
<212> TYPE: PRT
<213> ORGANISM: Artificial Sequence
<220> FEATURE:
<223> OTHER INFORMATION: synthetic
```

<400> SEQUENCE: 40

Val Lys Gly Gly Pro Ile Val Ala Thr Asp Tyr
1               5                   10

<210> SEQ ID NO 41
<211> LENGTH: 321
<212> TYPE: DNA
<213> ORGANISM: Artificial Sequence
<220> FEATURE:
<223> OTHER INFORMATION: synthetic

<400> SEQUENCE: 41

```
gacatccaga tgacccagtc tccttccacc ctgtctgcat ctgtaggaga cagagtcacc      60
atcacttgcc gggccagtca gagtattagt agctggttgg cctggcatca gcagaaacca    120
gggaaagccc ctaagctcct gatctataag gcgtctagtt tagaaagtgg ggtcccatca    180
aggttcagcg gcagtggatc tgggacagaa ttcactctca ccatcagcag cctgcagcct    240
gatgattttg caacttatta ctgccaacag tataatagtt attcgtggac gttcggccaa    300
gggaccaagg tggaaatcaa a                                              321
```

<210> SEQ ID NO 42
<211> LENGTH: 107
<212> TYPE: PRT
<213> ORGANISM: Artificial Sequence
<220> FEATURE:
<223> OTHER INFORMATION: synthetic

<400> SEQUENCE: 42

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp His Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Trp
                85                  90                  95

Thr Phe Gly Gln Gly Thr Lys Val Glu Ile Lys
            100                 105

<210> SEQ ID NO 43
<211> LENGTH: 18
<212> TYPE: DNA
<213> ORGANISM: Artificial Sequence
<220> FEATURE:
<223> OTHER INFORMATION: synthetic

<400> SEQUENCE: 43

```
cagagtatta gtagctgg                                                   18
```

<210> SEQ ID NO 44
<211> LENGTH: 6
<212> TYPE: PRT
<213> ORGANISM: Artificial Sequence
<220> FEATURE:
<223> OTHER INFORMATION: synthetic -continued

<400> SEQUENCE: 44

Gln Ser Ile Ser Ser Trp
1               5

<210> SEQ ID NO 45
<211> LENGTH: 9
<212> TYPE: DNA
<213> ORGANISM: Artificial Sequence
<220> FEATURE:
<223> OTHER INFORMATION: synthetic

<400> SEQUENCE: 45 aaggcgtct                                                                 9

<210> SEQ ID NO 46
<211> LENGTH: 3
<212> TYPE: PRT
<213> ORGANISM: Artificial Sequence
<220> FEATURE:
<223> OTHER INFORMATION: synthetic

<400> SEQUENCE: 46

Lys Ala Ser
1

<210> SEQ ID NO 47
<211> LENGTH: 27
<212> TYPE: DNA
<213> ORGANISM: Artificial Sequence
<220> FEATURE:
<223> OTHER INFORMATION: synthetic

<400> SEQUENCE: 47
caacagtata atagttattc gtggacg                                            27

<210> SEQ ID NO 48
<211> LENGTH: 9
<212> TYPE: PRT
<213> ORGANISM: Artificial Sequence
<220> FEATURE:
<223> OTHER INFORMATION: synthetic

<400> SEQUENCE: 48

Gln Gln Tyr Asn Ser Tyr Ser Trp Thr
1               5

<210> SEQ ID NO 49
<211> LENGTH: 354
<212> TYPE: DNA
<213> ORGANISM: Artificial Sequence
<220> FEATURE:
<223> OTHER INFORMATION: synthetic

<400> SEQUENCE: 49
gaggtgcagc tggtggagtc tgggggagac ttggtacagc ctggagggtc cctaagactc        60
tcctgtacag cctctggatt caccttcagt aattatgaaa tgaactgggt ccgccaggct       120
ccagagaagg ggctggactg ggtttcattc attagtagta gtggtggtgc catatactac       180
gcagactctg tgaagggccg attcaccatc tccagagaca cgccaagaa ctcactgtat        240 ctgcaaatga acagcctgag agccgaggac tcggctattt atttctgtgc gcgatccgac       300
tccggtggta actcgaggta ctggggccag ggaaccctgg tcaccgtctc ctca             354

<210> SEQ ID NO 50

<211> LENGTH: 118
<212> TYPE: PRT
<213> ORGANISM: Artificial Sequence
<220> FEATURE:
<223> OTHER INFORMATION: synthetic

<400> SEQUENCE: 50

Glu Val Gln Leu Val Glu Ser Gly Gly Asp Leu Val Gln Pro Gly Gly
1               5                   10                  15
Ser Leu Arg Leu Ser Cys Thr Ala Ser Gly Phe Thr Phe Ser Asn Tyr
            20                  25                  30
Glu Met Asn Trp Val Arg Gln Ala Pro Glu Lys Gly Leu Asp Trp Val
        35                  40                  45
Ser Phe Ile Ser Ser Ser Gly Gly Ala Ile Tyr Tyr Ala Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Ser Ala Ile Tyr Phe Cys
                85                  90                  95
Ala Arg Ser Asp Ser Gly Gly Asn Ser Arg Tyr Trp Gly Gln Gly Thr
            100                 105                 110
Leu Val Thr Val Ser Ser
        115

<210> SEQ ID NO 51
<211> LENGTH: 24
<212> TYPE: DNA
<213> ORGANISM: Artificial Sequence
<220> FEATURE:
<223> OTHER INFORMATION: synthetic

<400> SEQUENCE: 51
ggattcacct tcagtaatta tgaa                                          24

<210> SEQ ID NO 52
<211> LENGTH: 8
<212> TYPE: PRT
<213> ORGANISM: Artificial Sequence
<220> FEATURE:
<223> OTHER INFORMATION: synthetic

<400> SEQUENCE: 52

Gly Phe Thr Phe Ser Asn Tyr Glu
1               5

<210> SEQ ID NO 53
<211> LENGTH: 24
<212> TYPE: DNA
<213> ORGANISM: Artificial Sequence
<220> FEATURE:
<223> OTHER INFORMATION: synthetic

<400> SEQUENCE: 53
attagtagta gtggtggtgc cata                                          24

<210> SEQ ID NO 54
<211> LENGTH: 8
<212> TYPE: PRT
<213> ORGANISM: Artificial Sequence
<220> FEATURE:
<223> OTHER INFORMATION: synthetic

<400> SEQUENCE: 54

Ile Ser Ser Ser Gly Gly Ala Ile
1               5

<210> SEQ ID NO 55
<211> LENGTH: 33
<212> TYPE: DNA
<213> ORGANISM: Artificial Sequence
<220> FEATURE:
<223> OTHER INFORMATION: synthetic

<400> SEQUENCE: 55
gcgcgatccg actccggtgg taactcgagg tac                                33

<210> SEQ ID NO 56
<211> LENGTH: 11
<212> TYPE: PRT
<213> ORGANISM: Artificial Sequence
<220> FEATURE:
<223> OTHER INFORMATION: synthetic

<400> SEQUENCE: 56

Ala Arg Ser Asp Ser Gly Gly Asn Ser Arg Tyr
1               5                   10

<210> SEQ ID NO 57
<211> LENGTH: 321
<212> TYPE: DNA
<213> ORGANISM: Artificial Sequence
<220> FEATURE:
<223> OTHER INFORMATION: synthetic

<400> SEQUENCE: 57
gacatccaga tgacccagtc tccatcttcc gtgtctgcat ctgtaggaga cagagtcacc     60
gtcacttgtc gggcgagtca ggatattagc aactggttag tctggtatca gcagaaacca    120
gggaaagccc ctaagttcct gatctatgct gcatccagtt tgcaaagtgg ggtcccatca    180
aggttcagcg gcagtggatc tgggacagat ttcactctca ccatcagcag cctacagcct    240
gaagattttg cgacttacta ttgtcaacag gctaacagtt tccctcctac tttcggcgga    300
gggaccaagg tggagatcaa a                                              321

<210> SEQ ID NO 58
<211> LENGTH: 107
<212> TYPE: PRT
<213> ORGANISM: Artificial Sequence
<220> FEATURE:
<223> OTHER INFORMATION: synthetic

<400> SEQUENCE: 58

Asp Ile Gln Met Thr Gln Ser Pro Ser Ser Val Ser Ala Ser Val Gly
1               5                   10                  15

Asp Arg Val Thr Val Thr Cys Arg Ala Ser Gln Asp Ile Ser Asn Trp
            20                  25                  30

Leu Val Trp Tyr Gln Gln Lys Pro Gly Lys Ala Pro Lys Phe Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Pro
                85                  90                  95

Thr Phe Gly Gly Gly Thr Lys Val Glu Ile Lys
            100                 105

<210> SEQ ID NO 59
<211> LENGTH: 18
<212> TYPE: DNA
<213> ORGANISM: Artificial Sequence
<220> FEATURE:
<223> OTHER INFORMATION: synthetic

<400> SEQUENCE: 59
caggatatta gcaactgg                                                    18

<210> SEQ ID NO 60
<211> LENGTH: 6
<212> TYPE: PRT
<213> ORGANISM: Artificial Sequence
<220> FEATURE:
<223> OTHER INFORMATION: synthetic

<400> SEQUENCE: 60

Gln Asp Ile Ser Asn Trp
1               5

<210> SEQ ID NO 61
<211> LENGTH: 9
<212> TYPE: DNA
<213> ORGANISM: Artificial Sequence
<220> FEATURE:
<223> OTHER INFORMATION: synthetic

<400> SEQUENCE: 61 gctgcatcc                                                               9

<210> SEQ ID NO 62
<211> LENGTH: 3
<212> TYPE: PRT
<213> ORGANISM: Artificial Sequence
<220> FEATURE:
<223> OTHER INFORMATION: synthetic

<400> SEQUENCE: 62

Ala Ala Ser
1

<210> SEQ ID NO 63
<211> LENGTH: 27
<212> TYPE: DNA
<213> ORGANISM: Artificial Sequence
<220> FEATURE:
<223> OTHER INFORMATION: synthetic

<400> SEQUENCE: 63
caacaggcta acagtttccc tcctact                                          27

<210> SEQ ID NO 64
<211> LENGTH: 9
<212> TYPE: PRT
<213> ORGANISM: Artificial Sequence
<220> FEATURE:
<223> OTHER INFORMATION: synthetic

<400> SEQUENCE: 64

Gln Gln Ala Asn Ser Phe Pro Pro Thr
1               5

<210> SEQ ID NO 65

<211> LENGTH: 354
<212> TYPE: DNA
<213> ORGANISM: Artificial Sequence
<220> FEATURE:
<223> OTHER INFORMATION: synthetic

<400> SEQUENCE: 65

```
gaggtgcagc tggtggagtc tgggggaggc ttggtacagc ctggggggtc cctgagactc      60
tcctgtgtag tttctggatt cacctttagt aattatgaca tgagctgggt ccgccaggct     120
ccagggaggg ggctggagtg ggtctcagct attaggggta gtggttttaa cacatattac     180
gcagactccg tgaagggccg gttcaccatc tccagagaca attccaagaa cacgctgtat     240
ctgcaaatga acagcctgag agccgaggac acggccgtat attactgtgc gaaagatggg     300
tctatagtga gtatggacta ctggggccag ggaaccctgg tcaccgtctc ctca           354
```

<210> SEQ ID NO 66
<211> LENGTH: 118
<212> TYPE: PRT
<213> ORGANISM: Artificial Sequence
<220> FEATURE:
<223> OTHER INFORMATION: synthetic

<400> SEQUENCE: 66

```
Glu Val Gln Leu Val Glu Ser Gly Gly Gly Leu Val Gln Pro Gly Gly
1               5                   10                  15
Ser Leu Arg Leu Ser Cys Val Val Ser Gly Phe Thr Phe Ser Asn Tyr
            20                  25                  30
Asp Met Ser Trp Val Arg Gln Ala Pro Gly Arg Gly Leu Glu Trp Val
        35                  40                  45
Ser Ala Ile Arg Gly Ser Gly Phe Asn Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys Asp Gly Ser Ile Val Ser Met Asp Tyr Trp Gly Gln Gly Thr
            100                 105                 110
Leu Val Thr Val Ser Ser
        115
```

<210> SEQ ID NO 67
<211> LENGTH: 24
<212> TYPE: DNA
<213> ORGANISM: Artificial Sequence
<220> FEATURE:
<223> OTHER INFORMATION: synthetic

<400> SEQUENCE: 67

```
ggattcacct ttagtaatta tgac                                              24
```

<210> SEQ ID NO 68
<211> LENGTH: 8
<212> TYPE: PRT
<213> ORGANISM: Artificial Sequence
<220> FEATURE:
<223> OTHER INFORMATION: synthetic

<400> SEQUENCE: 68

```
Gly Phe Thr Phe Ser Asn Tyr Asp
1               5
```

<210> SEQ ID NO 69
<211> LENGTH: 24
<212> TYPE: DNA
<213> ORGANISM: Artificial Sequence
<220> FEATURE:
<223> OTHER INFORMATION: synthetic

<400> SEQUENCE: 69 attagggta gtggttttaa caca                                            24

<210> SEQ ID NO 70
<211> LENGTH: 8
<212> TYPE: PRT
<213> ORGANISM: Artificial Sequence
<220> FEATURE:
<223> OTHER INFORMATION: synthetic

<400> SEQUENCE: 70

Ile Arg Gly Ser Gly Phe Asn Thr
1               5

<210> SEQ ID NO 71
<211> LENGTH: 33
<212> TYPE: DNA
<213> ORGANISM: Artificial Sequence
<220> FEATURE:
<223> OTHER INFORMATION: synthetic

<400> SEQUENCE: 71
gcgaaagatg ggtctatagt gagtatggac tac                                 33

<210> SEQ ID NO 72
<211> LENGTH: 11
<212> TYPE: PRT
<213> ORGANISM: Artificial Sequence
<220> FEATURE:
<223> OTHER INFORMATION: synthetic

<400> SEQUENCE: 72

Ala Lys Asp Gly Ser Ile Val Ser Met Asp Tyr
1               5                   10

<210> SEQ ID NO 73
<211> LENGTH: 321
<212> TYPE: DNA
<213> ORGANISM: Artificial Sequence
<220> FEATURE:
<223> OTHER INFORMATION: synthetic

<400> SEQUENCE: 73
gacatccaga tgacccagtc tccttccgcc ctgtctgcat ctgtaggaga cagagtcacc    60
atcacttgcc gggccagtca gagtattagt agctggttgg cctggtatca gcagaaacca   120
gggaaagccc ctaaactcct gatctataag gcgtctagtt tagaaagtgg ggtcccatca   180
aggttcagtg gcagtggatc tgggacagaa ttcactctca ccatcagcag cctgcagcct   240
gatgattttg caacttatta ctgccaacag tataatagtt attcgtggac gttcggccaa   300
gggaccaagg tggaaatcaa a                                             321

<210> SEQ ID NO 74
<211> LENGTH: 107
<212> TYPE: PRT
<213> ORGANISM: Artificial Sequence
<220> FEATURE:
<223> OTHER INFORMATION: synthetic

<400> SEQUENCE: 74

Asp Ile Gln Met Thr Gln Ser Pro Ser Ala Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Trp
                85                  90                  95

Thr Phe Gly Gln Gly Thr Lys Val Glu Ile Lys
            100                 105

<210> SEQ ID NO 75
<211> LENGTH: 18
<212> TYPE: DNA
<213> ORGANISM: Artificial Sequence
<220> FEATURE:
<223> OTHER INFORMATION: synthetic

<400> SEQUENCE: 75
cagagtatta gtagctgg                                                 18

<210> SEQ ID NO 76
<211> LENGTH: 6
<212> TYPE: PRT
<213> ORGANISM: Artificial Sequence
<220> FEATURE:
<223> OTHER INFORMATION: synthetic

<400> SEQUENCE: 76

Gln Ser Ile Ser Ser Trp
1               5

<210> SEQ ID NO 77
<211> LENGTH: 9
<212> TYPE: DNA
<213> ORGANISM: Artificial Sequence
<220> FEATURE:
<223> OTHER INFORMATION: synthetic

<400> SEQUENCE: 77 aaggcgtct                                                            9

<210> SEQ ID NO 78
<211> LENGTH: 3
<212> TYPE: PRT
<213> ORGANISM: Artificial Sequence
<220> FEATURE:
<223> OTHER INFORMATION: synthetic

<400> SEQUENCE: 78

Lys Ala Ser
1

<210> SEQ ID NO 79
<211> LENGTH: 27
<212> TYPE: DNA
<213> ORGANISM: Artificial Sequence

```
<220> FEATURE:
<223> OTHER INFORMATION: synthetic

<400> SEQUENCE: 79
caacagtata atagttattc gtggacg                                             27

<210> SEQ ID NO 80
<211> LENGTH: 9
<212> TYPE: PRT
<213> ORGANISM: Artificial Sequence
<220> FEATURE:
<223> OTHER INFORMATION: synthetic

<400> SEQUENCE: 80

Gln Gln Tyr Asn Ser Tyr Ser Trp Thr
1               5

<210> SEQ ID NO 81
<211> LENGTH: 354
<212> TYPE: DNA
<213> ORGANISM: Artificial Sequence
<220> FEATURE:
<223> OTHER INFORMATION: synthetic

<400> SEQUENCE: 81
gaggtgcagc tggtggagtc tgggggaggc ttggtacagc cggggggtc cctgagactc        60 tcctgtgcag cctctggatt cacctttagc acctatggca tgagctgggt ccgccaggct       120
ccagggaagg ggctggagtg ggtctcaact attattggta gtggttataa cacatactac       180
tcagactccg tgaagggccg gttcaccatg tccagagaca attccaagag cacgctgtat       240
ctgcaaatga acagcctgag agccgaggac acggccgtat attactgtac gaaagaaggc       300
cctataattg gaaccacgaa ctggggccag ggaaccctgg tcaccgtctc ctca             354

<210> SEQ ID NO 82
<211> LENGTH: 118
<212> TYPE: PRT
<213> ORGANISM: Artificial Sequence
<220> FEATURE:
<223> OTHER INFORMATION: synthetic

<400> SEQUENCE: 82

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Met Ser Trp Val Arg Gln Ala Pro Gly Lys Gly Leu Glu Trp Val
        35                  40                  45

Ser Thr Ile Ile Gly Ser Gly Tyr Asn Thr Tyr Tyr Ser Asp Ser Val
    50                  55                  60

Lys Gly Arg Phe Thr Met Ser Arg Asp Asn Ser Lys Ser Thr Leu Tyr
65                  70                  75                  80

Leu Gln Met Asn Ser Leu Arg Ala Glu Asp Thr Ala Val Tyr Tyr Cys
                85                  90                  95

Thr Lys Glu Gly Pro Ile Ile Gly Thr Thr Asn Trp Gly Gln Gly Thr
            100                 105                 110

Leu Val Thr Val Ser Ser
        115

<210> SEQ ID NO 83
<211> LENGTH: 24
```

```
<212> TYPE: DNA
<213> ORGANISM: Artificial Sequence
<220> FEATURE:
<223> OTHER INFORMATION: synthetic

<400> SEQUENCE: 83
ggattcacct ttagcaccta tggc                                         24

<210> SEQ ID NO 84
<211> LENGTH: 8
<212> TYPE: PRT
<213> ORGANISM: Artificial Sequence
<220> FEATURE:
<223> OTHER INFORMATION: synthetic

<400> SEQUENCE: 84

Gly Phe Thr Phe Ser Thr Tyr Gly
1               5

<210> SEQ ID NO 85
<211> LENGTH: 24
<212> TYPE: DNA
<213> ORGANISM: Artificial Sequence
<220> FEATURE:
<223> OTHER INFORMATION: synthetic

<400> SEQUENCE: 85
attattggta gtggttataa caca                                         24

<210> SEQ ID NO 86
<211> LENGTH: 8
<212> TYPE: PRT
<213> ORGANISM: Artificial Sequence
<220> FEATURE:
<223> OTHER INFORMATION: synthetic

<400> SEQUENCE: 86

Ile Ile Gly Ser Gly Tyr Asn Thr
1               5

<210> SEQ ID NO 87
<211> LENGTH: 33
<212> TYPE: DNA
<213> ORGANISM: Artificial Sequence
<220> FEATURE:
<223> OTHER INFORMATION: synthetic

<400> SEQUENCE: 87
acgaaagaag gccctataat tggaaccacg aac                               33

<210> SEQ ID NO 88
<211> LENGTH: 11
<212> TYPE: PRT
<213> ORGANISM: Artificial Sequence
<220> FEATURE:
<223> OTHER INFORMATION: synthetic

<400> SEQUENCE: 88

Thr Lys Glu Gly Pro Ile Ile Gly Thr Thr Asn
1               5                   10

<210> SEQ ID NO 89
<211> LENGTH: 321
<212> TYPE: DNA
<213> ORGANISM: Artificial Sequence
<220> FEATURE:
<223> OTHER INFORMATION: synthetic
```

<400> SEQUENCE: 89

```
gacatccaga tgacccagtc tccttccacc ctgtctgcat ctgtaggaga cagagtcacc    60
atcacttgcc gggccagtca gagtattagt agctggttgg cctggtatca acagaaacca   120
gggaaagccc ctaagctcct gatctataag gcgtctagtt tagaaagtgg ggtcccatca   180
aggttcagcg gcagtggatc tgggacagaa ttcactctca ccatcagcag cctgcagcct   240
gacgattttg caacttatta ctgccaccaa tataatagtt attcgtggac gttcggccaa   300
gggaccaagg tggaaatcaa a                                             321
```

<210> SEQ ID NO 90
<211> LENGTH: 107
<212> TYPE: PRT
<213> ORGANISM: Artificial Sequence
<220> FEATURE:
<223> OTHER INFORMATION: synthetic

<400> SEQUENCE: 90

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys His Gln Tyr Asn Ser Tyr Ser Trp
                85                  90                  95

Thr Phe Gly Gln Gly Thr Lys Val Glu Ile Lys
            100                 105

<210> SEQ ID NO 91
<211> LENGTH: 18
<212> TYPE: DNA
<213> ORGANISM: Artificial Sequence
<220> FEATURE:
<223> OTHER INFORMATION: synthetic

<400> SEQUENCE: 91

```
cagagtatta gtagctgg                                                  18
```

<210> SEQ ID NO 92
<211> LENGTH: 6
<212> TYPE: PRT
<213> ORGANISM: Artificial Sequence
<220> FEATURE:
<223> OTHER INFORMATION: synthetic

<400> SEQUENCE: 92

Gln Ser Ile Ser Ser Trp
1               5

<210> SEQ ID NO 93
<211> LENGTH: 9
<212> TYPE: DNA
<213> ORGANISM: Artificial Sequence
<220> FEATURE:
<223> OTHER INFORMATION: synthetic

```
<400> SEQUENCE: 93 aaggcgtct                                                                    9

<210> SEQ ID NO 94
<211> LENGTH: 3
<212> TYPE: PRT
<213> ORGANISM: Artificial Sequence
<220> FEATURE:
<223> OTHER INFORMATION: synthetic

<400> SEQUENCE: 94

Lys Ala Ser
1

<210> SEQ ID NO 95
<211> LENGTH: 27
<212> TYPE: DNA
<213> ORGANISM: Artificial Sequence
<220> FEATURE:
<223> OTHER INFORMATION: synthetic

<400> SEQUENCE: 95
caccaatata atagttattc gtggacg                                               27

<210> SEQ ID NO 96
<211> LENGTH: 9
<212> TYPE: PRT
<213> ORGANISM: Artificial Sequence
<220> FEATURE:
<223> OTHER INFORMATION: synthetic

<400> SEQUENCE: 96

His Gln Tyr Asn Ser Tyr Ser Trp Thr
1               5

<210> SEQ ID NO 97
<211> LENGTH: 351
<212> TYPE: DNA
<213> ORGANISM: Artificial Sequence
<220> FEATURE:
<223> OTHER INFORMATION: synthetic

<400> SEQUENCE: 97
gaggtgcagc tggtggagtc tgggggaggc ttggtgcagc ctggggggtc cctgagactc           60
tcctgtgcag tctttggatt cacctttagc ggctatgcca tgagctgggt ccgccaggct          120
ccagggaagg gctggagtg gtctcagct attagtggtg gtggtggtag cacatactac           180
acagactccg tgaagggccg gttcaccatc tccagagaca attccaagaa cacgctgtat          240
ctgcaaatga acagcctgag agccgaggac acggccgtat attactgtgc gtcctactgg          300
aacaacggta tggacgtctg gggccaaggg accacggtca ccgtctcctc a                   351

<210> SEQ ID NO 98
<211> LENGTH: 117
<212> TYPE: PRT
<213> ORGANISM: Artificial Sequence
<220> FEATURE:
<223> OTHER INFORMATION: synthetic

<400> SEQUENCE: 98

Glu Val Gln Leu Val Glu Ser Gly Gly Gly Leu Val Gln Pro Gly Gly
1               5                   10                  15

Ser Leu Arg Leu Ser Cys Ala Val Phe Gly Phe Thr Phe Ser Gly Tyr
            20                  25                  30
```

```
Ala Met Ser Trp Val Arg Gln Ala Pro Gly Lys Gly Leu Glu Trp Val
        35                  40                  45
Ser Ala Ile Ser Gly Gly Gly Gly Ser Thr Tyr Tyr Thr Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Ser Tyr Trp Asn Asn Gly Met Asp Val Trp Gly Gln Gly Thr Thr
                100                 105                 110
Val Thr Val Ser Ser
        115

<210> SEQ ID NO 99
<211> LENGTH: 24
<212> TYPE: DNA
<213> ORGANISM: Artificial Sequence
<220> FEATURE:
<223> OTHER INFORMATION: synthetic

<400> SEQUENCE: 99
ggattcacct ttagcggcta tgcc                                          24

<210> SEQ ID NO 100
<211> LENGTH: 8
<212> TYPE: PRT
<213> ORGANISM: Artificial Sequence
<220> FEATURE:
<223> OTHER INFORMATION: synthetic

<400> SEQUENCE: 100

Gly Phe Thr Phe Ser Gly Tyr Ala
 1               5

<210> SEQ ID NO 101
<211> LENGTH: 24
<212> TYPE: DNA
<213> ORGANISM: Artificial Sequence
<220> FEATURE:
<223> OTHER INFORMATION: synthetic

<400> SEQUENCE: 101
attagtggtg gtggtggtag caca                                          24

<210> SEQ ID NO 102
<211> LENGTH: 8
<212> TYPE: PRT
<213> ORGANISM: Artificial Sequence
<220> FEATURE:
<223> OTHER INFORMATION: synthetic

<400> SEQUENCE: 102

Ile Ser Gly Gly Gly Gly Ser Thr
 1               5

<210> SEQ ID NO 103
<211> LENGTH: 30
<212> TYPE: DNA
<213> ORGANISM: Artificial Sequence
<220> FEATURE:
<223> OTHER INFORMATION: synthetic

<400> SEQUENCE: 103
```

```
gcgtcctact ggaacaacgg tatggacgtc                                        30
```

<210> SEQ ID NO 104
<211> LENGTH: 10
<212> TYPE: PRT
<213> ORGANISM: Artificial Sequence
<220> FEATURE:
<223> OTHER INFORMATION: synthetic

<400> SEQUENCE: 104

```
Ala Ser Tyr Trp Asn Asn Gly Met Asp Val
1               5                   10
```

<210> SEQ ID NO 105
<211> LENGTH: 324
<212> TYPE: DNA
<213> ORGANISM: Artificial Sequence
<220> FEATURE:
<223> OTHER INFORMATION: synthetic

<400> SEQUENCE: 105

```
gacatccaga tgacccagtc tccatcctcc ctgtctgcat ctgtaggaga cagagtcacc       60
atcacttgcc gggcaagtca gagcattagc agctatttaa attggtatca gcagaaacca      120
gggaaagccc ctaagctcct gatctatgct gcatccagtt tgcaaagtgg ggtcccgtca      180
aggttcagtg gcagtggatc tgggacagat ttcactctca ccatcagcag tctgcaacct      240
gaagattttg caacttacta ctgtcaacag agttacagta cccctccgat caccttcggc      300
caagggacac gactggagat taaa                                            324
```

<210> SEQ ID NO 106
<211> LENGTH: 108
<212> TYPE: PRT
<213> ORGANISM: Artificial Sequence
<220> FEATURE:
<223> OTHER INFORMATION: synthetic

<400> SEQUENCE: 106

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105
```

<210> SEQ ID NO 107
<211> LENGTH: 18
<212> TYPE: DNA
<213> ORGANISM: Artificial Sequence
<220> FEATURE:
<223> OTHER INFORMATION: synthetic

<400> SEQUENCE: 107

```
cagagcatta gcagctat                                                     18
```

<210> SEQ ID NO 108
<211> LENGTH: 6
<212> TYPE: PRT
<213> ORGANISM: Artificial Sequence
<220> FEATURE:
<223> OTHER INFORMATION: synthetic

<400> SEQUENCE: 108

Gln Ser Ile Ser Ser Tyr
1               5

<210> SEQ ID NO 109
<211> LENGTH: 9
<212> TYPE: DNA
<213> ORGANISM: Artificial Sequence
<220> FEATURE:
<223> OTHER INFORMATION: synthetic

<400> SEQUENCE: 109 gctgcatcc                                                                 9

<210> SEQ ID NO 110
<211> LENGTH: 3
<212> TYPE: PRT
<213> ORGANISM: Artificial Sequence
<220> FEATURE:
<223> OTHER INFORMATION: synthetic

<400> SEQUENCE: 110

Ala Ala Ser
1

<210> SEQ ID NO 111
<211> LENGTH: 30
<212> TYPE: DNA
<213> ORGANISM: Artificial Sequence
<220> FEATURE:
<223> OTHER INFORMATION: synthetic

<400> SEQUENCE: 111
caacagagtt acagtacccc tccgatcacc                                         30

<210> SEQ ID NO 112
<211> LENGTH: 10
<212> TYPE: PRT
<213> ORGANISM: Artificial Sequence
<220> FEATURE:
<223> OTHER INFORMATION: synthetic

<400> SEQUENCE: 112

Gln Gln Ser Tyr Ser Thr Pro Pro Ile Thr
1               5                   10

<210> SEQ ID NO 113
<211> LENGTH: 360
<212> TYPE: DNA
<213> ORGANISM: Artificial Sequence
<220> FEATURE:
<223> OTHER INFORMATION: synthetic

<400> SEQUENCE: 113
cagctgcagc tgcaggagtc gggcccagga ctagtgaagc cttcggagac cctgtccctc         60
acctgcactg tctctggtgg ctccatcagt agtaatactt actactgggg ctggatccgc        120
cagcccccag ggaaggggct ggagtggatt ggaactatat attatactgg gaacacctac        180

```
tacaagtcgt ccctcaagag tcgagtcacc atatccgtag acacgtccag gaaccagttc        240
tccctgaagc tgacctctgt gaccgccgca gacacggctg tctattactg tgcgcgacag        300
tttgctgact tgaactacgt tgactactgg ggccagggaa ccctggtcac cgtctcctca        360
```

<210> SEQ ID NO 114
<211> LENGTH: 120
<212> TYPE: PRT
<213> ORGANISM: Artificial Sequence
<220> FEATURE:
<223> OTHER INFORMATION: synthetic

<400> SEQUENCE: 114

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Asn
            20                  25                  30

Thr Tyr Tyr Trp Gly Trp Ile Arg Gln Pro Pro Gly Lys Gly Leu Glu
        35                  40                  45

Trp Ile Gly Thr Ile Tyr Tyr Thr Gly Asn Thr Tyr Tyr Lys Ser Ser
    50                  55                  60

Leu Lys Ser Arg Val Thr Ile Ser Val Asp Thr Ser Arg Asn Gln Phe
65                  70                  75                  80

Ser Leu Lys Leu Thr Ser Val Thr Ala Ala Asp Thr Ala Val Tyr Tyr
            85                  90                  95

Cys Ala Arg Gln Phe Ala Asp Leu Asn Tyr Val Asp Tyr Trp Gly Gln
        100                 105                 110

Gly Thr Leu Val Thr Val Ser Ser
    115                 120
```

<210> SEQ ID NO 115
<211> LENGTH: 30
<212> TYPE: DNA
<213> ORGANISM: Artificial Sequence
<220> FEATURE:
<223> OTHER INFORMATION: synthetic

<400> SEQUENCE: 115

```
ggtggctcca tcagtagtaa tacttactac                                          30
```

<210> SEQ ID NO 116
<211> LENGTH: 10
<212> TYPE: PRT
<213> ORGANISM: Artificial Sequence
<220> FEATURE:
<223> OTHER INFORMATION: synthetic

<400> SEQUENCE: 116

```
Gly Gly Ser Ile Ser Ser Asn Thr Tyr Tyr
1               5                   10
```

<210> SEQ ID NO 117
<211> LENGTH: 21
<212> TYPE: DNA
<213> ORGANISM: Artificial Sequence
<220> FEATURE:
<223> OTHER INFORMATION: synthetic

<400> SEQUENCE: 117

```
atatattata ctgggaacac c                                                   21
```

```
<210> SEQ ID NO 118
<211> LENGTH: 7
<212> TYPE: PRT
<213> ORGANISM: Artificial Sequence
<220> FEATURE:
<223> OTHER INFORMATION: synthetic

<400> SEQUENCE: 118

Ile Tyr Tyr Thr Gly Asn Thr
1               5

<210> SEQ ID NO 119
<211> LENGTH: 36
<212> TYPE: DNA
<213> ORGANISM: Artificial Sequence
<220> FEATURE:
<223> OTHER INFORMATION: synthetic

<400> SEQUENCE: 119
gcgcgacagt ttgctgactt gaactacgtt gactac                              36

<210> SEQ ID NO 120
<211> LENGTH: 12
<212> TYPE: PRT
<213> ORGANISM: Artificial Sequence
<220> FEATURE:
<223> OTHER INFORMATION: synthetic

<400> SEQUENCE: 120

Ala Arg Gln Phe Ala Asp Leu Asn Tyr Val Asp Tyr
1               5                   10

<210> SEQ ID NO 121
<211> LENGTH: 363
<212> TYPE: DNA
<213> ORGANISM: Artificial Sequence
<220> FEATURE:
<223> OTHER INFORMATION: synthetic

<400> SEQUENCE: 121
gaggtgcagc tggtggagtc ggggggaggc ttggttcagc ctggggggtc cctgagactc      60
tcctgtgcag cctctggatt ctcctttagc agctatggca tgaactgggt ccgccaggct     120
ccagggaagg gctgagtg gtctcagct attagtggtc gtggtggtaa cacatactcc        180
gcagactccg tgaagggccg gttcaccatc tccagagaca attccaagaa cacgctgttt     240
cttcaaatga atggcctgag agccgaggac tcggcctttt attactgtgc gaaagtgggg     300
acttatagtt cttcgtcccc ctttgactac tggggccagg gaaccctggt caccgtctcc     360
tca                                                                  363

<210> SEQ ID NO 122
<211> LENGTH: 121
<212> TYPE: PRT
<213> ORGANISM: Artificial Sequence
<220> FEATURE:
<223> OTHER INFORMATION: synthetic

<400> SEQUENCE: 122

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Gly Met Asn Trp Val Arg Gln Ala Pro Gly Lys Gly Leu Glu Trp Val
        35                  40                  45
```

Ser Ala Ile Ser Gly Arg Gly Gly Asn Thr Tyr Ser Ala Asp Ser Val
        50                  55                  60

Lys Gly Arg Phe Thr Ile Ser Arg Asp Asn Ser Lys Asn Thr Leu Phe
 65                  70                  75                  80

Leu Gln Met Asn Gly Leu Arg Ala Glu Asp Ser Ala Phe Tyr Tyr Cys
                85                  90                  95

Ala Lys Val Gly Thr Tyr Ser Ser Ser Pro Phe Asp Tyr Trp Gly
            100                 105                 110

Gln Gly Thr Leu Val Thr Val Ser Ser
            115                 120

<210> SEQ ID NO 123
<211> LENGTH: 24
<212> TYPE: DNA
<213> ORGANISM: Artificial Sequence
<220> FEATURE:
<223> OTHER INFORMATION: synthetic

<400> SEQUENCE: 123
ggattctcct ttagcagcta tggc                                    24

<210> SEQ ID NO 124
<211> LENGTH: 8
<212> TYPE: PRT
<213> ORGANISM: Artificial Sequence
<220> FEATURE:
<223> OTHER INFORMATION: synthetic

<400> SEQUENCE: 124

Gly Phe Ser Phe Ser Ser Tyr Gly
 1               5

<210> SEQ ID NO 125
<211> LENGTH: 24
<212> TYPE: DNA
<213> ORGANISM: Artificial Sequence
<220> FEATURE:
<223> OTHER INFORMATION: synthetic

<400> SEQUENCE: 125
attagtggtc gtggtggtaa caca                                    24

<210> SEQ ID NO 126
<211> LENGTH: 8
<212> TYPE: PRT
<213> ORGANISM: Artificial Sequence
<220> FEATURE:
<223> OTHER INFORMATION: synthetic

<400> SEQUENCE: 126

Ile Ser Gly Arg Gly Gly Asn Thr
 1               5

<210> SEQ ID NO 127
<211> LENGTH: 42
<212> TYPE: DNA
<213> ORGANISM: Artificial Sequence
<220> FEATURE:
<223> OTHER INFORMATION: synthetic

<400> SEQUENCE: 127
gcgaaagtgg ggacttatag ttcttcgtcc cccttttgact ac                42

<210> SEQ ID NO 128
<211> LENGTH: 14
<212> TYPE: PRT
<213> ORGANISM: Artificial Sequence
<220> FEATURE:
<223> OTHER INFORMATION: synthetic

<400> SEQUENCE: 128

Ala Lys Val Gly Thr Tyr Ser Ser Ser Pro Phe Asp Tyr
1               5                   10

<210> SEQ ID NO 129
<211> LENGTH: 348
<212> TYPE: DNA
<213> ORGANISM: Artificial Sequence
<220> FEATURE:
<223> OTHER INFORMATION: synthetic

<400> SEQUENCE: 129
gaggtgcagc tggtggagtc tgggggaggc ttggttcagc ctgggggtc cctgagactc      60 tcctgtgcag cctctggatt cacctctaac agctatccca tgagctgggt ccgccaggct    120
ccagggaagg gctggagtg gtctcaggt attagtggta gaggtggtaa cacatactac      180
gcagactccg tgaagggccg gttcaccatc tccagagaca attccaagaa cactctgtat    240
ctgcaaatga acagcctgag agtcgaggac acggccgtat attactgtgc ggaaactgga    300
actgcctttg actactgggg ccagggaacc ctggtcaccg tctcctca                 348

<210> SEQ ID NO 130
<211> LENGTH: 116
<212> TYPE: PRT
<213> ORGANISM: Artificial Sequence
<220> FEATURE:
<223> OTHER INFORMATION: synthetic

<400> SEQUENCE: 130

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ser Asn Ser Tyr
            20                  25                  30

Pro Met Ser Trp Val Arg Gln Ala Pro Gly Lys Gly Leu Glu Trp Val
        35                  40                  45

Ser Gly Ile Ser Gly Arg Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Glu Thr Gly Thr Ala Phe Asp Tyr Trp Gly Gln Gly Thr Leu Val
            100                 105                 110

Thr Val Ser Ser
        115

<210> SEQ ID NO 131
<211> LENGTH: 24
<212> TYPE: DNA
<213> ORGANISM: Artificial Sequence
<220> FEATURE:
<223> OTHER INFORMATION: synthetic

<400> SEQUENCE: 131
ggattcacct ctaacagcta tccc                                            24

<210> SEQ ID NO 132
<211> LENGTH: 8
<212> TYPE: PRT
<213> ORGANISM: Artificial Sequence
<220> FEATURE:
<223> OTHER INFORMATION: synthetic

<400> SEQUENCE: 132

Gly Phe Thr Ser Asn Ser Tyr Pro
1               5

<210> SEQ ID NO 133
<211> LENGTH: 24
<212> TYPE: DNA
<213> ORGANISM: Artificial Sequence
<220> FEATURE:
<223> OTHER INFORMATION: synthetic

<400> SEQUENCE: 133
attagtggta gaggtggtaa caca                                           24

<210> SEQ ID NO 134
<211> LENGTH: 8
<212> TYPE: PRT
<213> ORGANISM: Artificial Sequence
<220> FEATURE:
<223> OTHER INFORMATION: synthetic

<400> SEQUENCE: 134

Ile Ser Gly Arg Gly Gly Asn Thr
1               5

<210> SEQ ID NO 135
<211> LENGTH: 27
<212> TYPE: DNA
<213> ORGANISM: Artificial Sequence
<220> FEATURE:
<223> OTHER INFORMATION: synthetic

<400> SEQUENCE: 135
gcggaaactg gaactgcctt tgactac                                        27

<210> SEQ ID NO 136
<211> LENGTH: 9
<212> TYPE: PRT
<213> ORGANISM: Artificial Sequence
<220> FEATURE:
<223> OTHER INFORMATION: synthetic

<400> SEQUENCE: 136

Ala Glu Thr Gly Thr Ala Phe Asp Tyr
1               5

<210> SEQ ID NO 137
<211> LENGTH: 360
<212> TYPE: DNA
<213> ORGANISM: Artificial Sequence
<220> FEATURE:
<223> OTHER INFORMATION: synthetic

<400> SEQUENCE: 137
cagctgcagc tgcaggagtc gggcccagga ctggtgaagc cttcggagac cctgtccctc     60
acctgcactg tctctggtgg ctccatcagc aataataatt actactgggg ctggatccgc    120
cagcccccag ggaaggggct ggactggatt gggagtatct attatagtgg gaatacctac    180

```
tacaacccgt ccctcaagag tcgagtcacc atatccgttg acacgtccaa gaaccagttc    240
tccctgaaga tgagttctgt gaccgccaca gacacggctc tgtattactg tgcgagacag    300
ggagcagatc acaactgggt cgaccccctgg ggccagggaa ccctggtcac cgtctcctca   360
```

```
<210> SEQ ID NO 138
<211> LENGTH: 120
<212> TYPE: PRT
<213> ORGANISM: Artificial Sequence
<220> FEATURE:
<223> OTHER INFORMATION: synthetic

<400> SEQUENCE: 138
```

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Asn Asn
            20                  25                  30

Asn Tyr Tyr Trp Gly Trp Ile Arg Gln Pro Pro Gly Lys Gly Leu Asp
        35                  40                  45

Trp Ile Gly Ser Ile Tyr Tyr Ser Gly Asn Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Met Ser Ser Val Thr Ala Thr Asp Thr Ala Leu Tyr Tyr
                85                  90                  95

Cys Ala Arg Gln Gly Ala Asp His Asn Trp Val Asp Pro Trp Gly Gln
            100                 105                 110

Gly Thr Leu Val Thr Val Ser Ser
        115                 120

```
<210> SEQ ID NO 139
<211> LENGTH: 30
<212> TYPE: DNA
<213> ORGANISM: Artificial Sequence
<220> FEATURE:
<223> OTHER INFORMATION: synthetic

<400> SEQUENCE: 139
ggtggctcca tcagcaataa taattactac                                      30

<210> SEQ ID NO 140
<211> LENGTH: 10
<212> TYPE: PRT
<213> ORGANISM: Artificial Sequence
<220> FEATURE:
<223> OTHER INFORMATION: synthetic

<400> SEQUENCE: 140
```

Gly Gly Ser Ile Ser Asn Asn Tyr Tyr
1               5                   10

```
<210> SEQ ID NO 141
<211> LENGTH: 21
<212> TYPE: DNA
<213> ORGANISM: Artificial Sequence
<220> FEATURE:
<223> OTHER INFORMATION: synthetic

<400> SEQUENCE: 141
atctattata gtgggaatac c                                               21
```

```
<210> SEQ ID NO 142
<211> LENGTH: 7
<212> TYPE: PRT
<213> ORGANISM: Artificial Sequence
<220> FEATURE:
<223> OTHER INFORMATION: synthetic

<400> SEQUENCE: 142

Ile Tyr Tyr Ser Gly Asn Thr
1               5

<210> SEQ ID NO 143
<211> LENGTH: 36
<212> TYPE: DNA
<213> ORGANISM: Artificial Sequence
<220> FEATURE:
<223> OTHER INFORMATION: synthetic

<400> SEQUENCE: 143
gcgagacagg gagcagatca caactgggtc gacccc                              36

<210> SEQ ID NO 144
<211> LENGTH: 12
<212> TYPE: PRT
<213> ORGANISM: Artificial Sequence
<220> FEATURE:
<223> OTHER INFORMATION: synthetic

<400> SEQUENCE: 144

Ala Arg Gln Gly Ala Asp His Asn Trp Val Asp Pro
1               5                   10

<210> SEQ ID NO 145
<211> LENGTH: 351
<212> TYPE: DNA
<213> ORGANISM: Artificial Sequence
<220> FEATURE:
<223> OTHER INFORMATION: synthetic

<400> SEQUENCE: 145
gaggtgcagc tggtggagtc tgggggaggc ttggtacagc ctgggggtc cctgagactc      60 tcctgtgttg tctctggatt cacctctaga aactatgcca tgagctgggt ccgccaggct    120
ccagggaagg ggctggagtg ggtctcagct attagtggta gtggtgggag cacatactac    180
gcagactccg tgaagggccg gttcaccatc tccagagaca tcccaagaa cacgttgtat    240 ctacaaatga acagcctgag agccgaggac acggccctat attactgtgc ggaagatcct    300
ggaacttctt ttgactactg gggccaggga accctggtca ccgtctcctc a            351

<210> SEQ ID NO 146
<211> LENGTH: 117
<212> TYPE: PRT
<213> ORGANISM: Artificial Sequence
<220> FEATURE:
<223> OTHER INFORMATION: synthetic

<400> SEQUENCE: 146

Glu Val Gln Leu Val Glu Ser Gly Gly Gly Leu Val Gln Pro Gly Gly
1               5                   10                  15

Ser Leu Arg Leu Ser Cys Val Val Ser Gly Phe Thr Ser Arg Asn Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
```

```
                50                  55                  60
Lys Gly Arg Phe Thr Ile Ser Arg Asp Asn Pro Lys Asn Thr Leu Tyr
 65                  70                  75                  80

Leu Gln Met Asn Ser Leu Arg Ala Glu Asp Thr Ala Leu Tyr Tyr Cys
                 85                  90                  95

Ala Glu Asp Pro Gly Thr Ser Phe Asp Tyr Trp Gly Gln Gly Thr Leu
            100                 105                 110

Val Thr Val Ser Ser
            115

<210> SEQ ID NO 147
<211> LENGTH: 24
<212> TYPE: DNA
<213> ORGANISM: Artificial Sequence
<220> FEATURE:
<223> OTHER INFORMATION: synthetic

<400> SEQUENCE: 147
ggattcacct ctagaaacta tgcc                                        24

<210> SEQ ID NO 148
<211> LENGTH: 8
<212> TYPE: PRT
<213> ORGANISM: Artificial Sequence
<220> FEATURE:
<223> OTHER INFORMATION: synthetic

<400> SEQUENCE: 148

Gly Phe Thr Ser Arg Asn Tyr Ala
 1               5

<210> SEQ ID NO 149
<211> LENGTH: 24
<212> TYPE: DNA
<213> ORGANISM: Artificial Sequence
<220> FEATURE:
<223> OTHER INFORMATION: synthetic

<400> SEQUENCE: 149
attagtggta gtggtgggag caca                                        24

<210> SEQ ID NO 150
<211> LENGTH: 8
<212> TYPE: PRT
<213> ORGANISM: Artificial Sequence
<220> FEATURE:
<223> OTHER INFORMATION: synthetic

<400> SEQUENCE: 150

Ile Ser Gly Ser Gly Gly Ser Thr
 1               5

<210> SEQ ID NO 151
<211> LENGTH: 30
<212> TYPE: DNA
<213> ORGANISM: Artificial Sequence
<220> FEATURE:
<223> OTHER INFORMATION: synthetic

<400> SEQUENCE: 151
gcggaagatc ctggaacttc ttttgactac                                  30

<210> SEQ ID NO 152
<211> LENGTH: 10
```

```
<212> TYPE: PRT
<213> ORGANISM: Artificial Sequence
<220> FEATURE:
<223> OTHER INFORMATION: synthetic

<400> SEQUENCE: 152

Ala Glu Asp Pro Gly Thr Ser Phe Asp Tyr
1               5                   10

<210> SEQ ID NO 153
<211> LENGTH: 390
<212> TYPE: DNA
<213> ORGANISM: Artificial Sequence
<220> FEATURE:
<223> OTHER INFORMATION: synthetic

<400> SEQUENCE: 153
caggtgcagc tggtggagtc tgggggaggc gtggtccagc ctggagggtc cctgagactc    60
tcctgtgcag cgtctggatt caccttcagt aactatggca tacactgggt ccgccaggct   120
ccaggcaagg ggctggagtg ggtggcaggt atatactatg atggaagtaa taaatactat   180
ggagactccg tgaagggccg attcaccatc tccagagaca attccaagaa cacgctatat   240
ctgcaaatga acagcctgag agccgaggac acggctgttt attactgtgc gagagatcgg   300
ggtaataacc actactatca taataatccc tactactatt atcacggttt ggacgtctgg   360
ggccaaggga ccacggtcac cgtctcctca                                     390

<210> SEQ ID NO 154
<211> LENGTH: 130
<212> TYPE: PRT
<213> ORGANISM: Artificial Sequence
<220> FEATURE:
<223> OTHER INFORMATION: synthetic

<400> SEQUENCE: 154

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Ile His Trp Val Arg Gln Ala Pro Gly Lys Gly Leu Glu Trp Val
        35                  40                  45

Ala Gly Ile Tyr Tyr Asp Gly Ser Asn Lys Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Asn Asn His Tyr Tyr His Asn Asn Pro Tyr Tyr
            100                 105                 110

Tyr Tyr His Gly Leu Asp Val Trp Gly Gln Gly Thr Thr Val Thr Val
        115                 120                 125

Ser Ser
    130

<210> SEQ ID NO 155
<211> LENGTH: 24
<212> TYPE: DNA
<213> ORGANISM: Artificial Sequence
<220> FEATURE:
<223> OTHER INFORMATION: synthetic
```

<400> SEQUENCE: 155
ggattcacct tcagtaacta tggc                                          24

<210> SEQ ID NO 156
<211> LENGTH: 8
<212> TYPE: PRT
<213> ORGANISM: Artificial Sequence
<220> FEATURE:
<223> OTHER INFORMATION: synthetic

<400> SEQUENCE: 156

Gly Phe Thr Phe Ser Asn Tyr Gly
1               5

<210> SEQ ID NO 157
<211> LENGTH: 24
<212> TYPE: DNA
<213> ORGANISM: Artificial Sequence
<220> FEATURE:
<223> OTHER INFORMATION: synthetic

<400> SEQUENCE: 157
atatactatg atggaagtaa taaa                                          24

<210> SEQ ID NO 158
<211> LENGTH: 8
<212> TYPE: PRT
<213> ORGANISM: Artificial Sequence
<220> FEATURE:
<223> OTHER INFORMATION: synthetic

<400> SEQUENCE: 158

Ile Tyr Tyr Asp Gly Ser Asn Lys
1               5

<210> SEQ ID NO 159
<211> LENGTH: 69
<212> TYPE: DNA
<213> ORGANISM: Artificial Sequence
<220> FEATURE:
<223> OTHER INFORMATION: synthetic

<400> SEQUENCE: 159
gcgagagatc ggggtaataa ccactactat cataataatc cctactacta ttatcacggt    60
ttggacgtc                                                           69

<210> SEQ ID NO 160
<211> LENGTH: 23
<212> TYPE: PRT
<213> ORGANISM: Artificial Sequence
<220> FEATURE:
<223> OTHER INFORMATION: synthetic

<400> SEQUENCE: 160

Ala Arg Asp Arg Gly Asn Asn His Tyr Tyr His Asn Asn Pro Tyr Tyr
1               5                   10                  15

Tyr Tyr His Gly Leu Asp Val
            20

<210> SEQ ID NO 161
<211> LENGTH: 324
<212> TYPE: DNA
<213> ORGANISM: Artificial Sequence
<220> FEATURE:
<223> OTHER INFORMATION: synthetic

<400> SEQUENCE: 161

```
gaaatagttt tgacacagag tcccggcaca ctgtcactct ctcccgggga aagagccacc    60
ttgtcatgta gagcaagtca gtcagtctct agctcttatc tcgcctggta ccagcagaag   120
ccgggacagg ccctagact gctgatctac ggggcaagtt ccagggccac cggaatcccc   180
gaccggttca gtggaagcgg aagcggaacc gatttactt tgacgatttc tagactggag   240
ccagaggatt tcgccgttta ctattgtcaa cagtacggaa gcagcccgtg acgtttggc   300 cagggcacga aggtagaaat caag                                        324
```

<210> SEQ ID NO 162
<211> LENGTH: 108
<212> TYPE: PRT
<213> ORGANISM: Artificial Sequence
<220> FEATURE:
<223> OTHER INFORMATION: synthetic

<400> SEQUENCE: 162

```
Glu Ile Val Leu Thr Gln Ser Pro Gly Thr Leu Ser Leu Ser Pro Gly
1               5                  10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105
```

<210> SEQ ID NO 163
<211> LENGTH: 36
<212> TYPE: DNA
<213> ORGANISM: Artificial Sequence
<220> FEATURE:
<223> OTHER INFORMATION: synthetic

<400> SEQUENCE: 163

```
agagcaagtc agtcagtctc tagctcttat ctcgcc                            36
```

<210> SEQ ID NO 164
<211> LENGTH: 12
<212> TYPE: PRT
<213> ORGANISM: Artificial Sequence
<220> FEATURE:
<223> OTHER INFORMATION: synthetic

<400> SEQUENCE: 164

```
Arg Ala Ser Gln Ser Val Ser Ser Ser Tyr Leu Ala
1               5                  10
```

<210> SEQ ID NO 165
<211> LENGTH: 21
<212> TYPE: DNA
<213> ORGANISM: Artificial Sequence
<220> FEATURE:
<223> OTHER INFORMATION: synthetic

<400> SEQUENCE: 165
ggggcaagtt ccagggccac c                                                    21

<210> SEQ ID NO 166
<211> LENGTH: 7
<212> TYPE: PRT
<213> ORGANISM: Artificial Sequence
<220> FEATURE:
<223> OTHER INFORMATION: synthetic

<400> SEQUENCE: 166

Gly Ala Ser Ser Arg Ala Thr
1               5

<210> SEQ ID NO 167
<211> LENGTH: 27
<212> TYPE: DNA
<213> ORGANISM: Artificial Sequence
<220> FEATURE:
<223> OTHER INFORMATION: synthetic

<400> SEQUENCE: 167
caacagtacg gaagcagccc gtggacg                                              27

<210> SEQ ID NO 168
<211> LENGTH: 9
<212> TYPE: PRT
<213> ORGANISM: Artificial Sequence
<220> FEATURE:
<223> OTHER INFORMATION: synthetic

<400> SEQUENCE: 168

Gln Gln Tyr Gly Ser Ser Pro Trp Thr
1               5

<210> SEQ ID NO 169
<211> LENGTH: 345
<212> TYPE: DNA
<213> ORGANISM: Artificial Sequence
<220> FEATURE:
<223> OTHER INFORMATION: synthetic

<400> SEQUENCE: 169
caggtgcagc tgcaggagtc gggcccagga ctggtgaagc cttcggagac cctgtccctc          60
acctgctctg tctctggtgg ctccatcact agttcctatt ggagctggat ccggcagccc         120
ccaggaaggg gcctggagtg gattggatat gtctattact acgggaccac caaatacaac         180
ccctccctca agagtcgagt caccacatca atggacacgt ccaagaacca gttctccctg         240
aaactgaact ctgtgaccgc tgcggacacg gccgtttatt actgtgcgag actggaacta         300
ctctttgact actggggcca gggaaccctg gtcactgtct cctca                        345

<210> SEQ ID NO 170
<211> LENGTH: 115
<212> TYPE: PRT
<213> ORGANISM: Artificial Sequence
<220> FEATURE:
<223> OTHER INFORMATION: synthetic

<400> SEQUENCE: 170

Gln Val Gln Leu Gln Glu Ser Gly Pro Gly Leu Val Lys Pro Ser Glu
1               5                   10                  15

Thr Leu Ser Leu Thr Cys Ser Val Ser Gly Gly Ser Ile Thr Ser Ser
            20                  25                  30

```
Tyr Trp Ser Trp Ile Arg Gln Pro Pro Gly Arg Gly Leu Glu Trp Ile
            35                  40                  45
Gly Tyr Val Tyr Tyr Gly Thr Thr Lys Tyr Asn Pro Ser Leu Lys
     50                  55                  60
Ser Arg Val Thr Thr Ser Met Asp Thr Ser Lys Asn Gln Phe Ser Leu
 65                  70                  75                  80
Lys Leu Asn Ser Val Thr Ala Ala Asp Thr Ala Val Tyr Tyr Cys Ala
                 85                  90                  95
Arg Leu Glu Leu Leu Phe Asp Tyr Trp Gly Gln Gly Thr Leu Val Thr
            100                 105                 110
Val Ser Ser
        115
```

<210> SEQ ID NO 171
<211> LENGTH: 24
<212> TYPE: DNA
<213> ORGANISM: Artificial Sequence
<220> FEATURE:
<223> OTHER INFORMATION: synthetic

<400> SEQUENCE: 171
ggtggctcca tcactagttc ctat        24

<210> SEQ ID NO 172
<211> LENGTH: 8
<212> TYPE: PRT
<213> ORGANISM: Artificial Sequence
<220> FEATURE:
<223> OTHER INFORMATION: synthetic

<400> SEQUENCE: 172

```
Gly Gly Ser Ile Thr Ser Ser Tyr
 1               5
```

<210> SEQ ID NO 173
<211> LENGTH: 21
<212> TYPE: DNA
<213> ORGANISM: Artificial Sequence
<220> FEATURE:
<223> OTHER INFORMATION: synthetic

<400> SEQUENCE: 173
gtctattact acgggaccac c        21

<210> SEQ ID NO 174
<211> LENGTH: 7
<212> TYPE: PRT
<213> ORGANISM: Artificial Sequence
<220> FEATURE:
<223> OTHER INFORMATION: synthetic

<400> SEQUENCE: 174

```
Val Tyr Tyr Tyr Gly Thr Thr
 1               5
```

<210> SEQ ID NO 175
<211> LENGTH: 27
<212> TYPE: DNA
<213> ORGANISM: Artificial Sequence
<220> FEATURE:
<223> OTHER INFORMATION: synthetic

<400> SEQUENCE: 175
gcgagactgg aactactctt tgactac 27

<210> SEQ ID NO 176
<211> LENGTH: 9
<212> TYPE: PRT
<213> ORGANISM: Artificial Sequence
<220> FEATURE:
<223> OTHER INFORMATION: synthetic

<400> SEQUENCE: 176

Ala Arg Leu Glu Leu Leu Phe Asp Tyr
1               5

<210> SEQ ID NO 177
<211> LENGTH: 363
<212> TYPE: DNA
<213> ORGANISM: Artificial Sequence
<220> FEATURE:
<223> OTHER INFORMATION: synthetic

<400> SEQUENCE: 177
cagctgcagc tgcaggagtc gggcccagga ctggtgaagc cttcggagac cctgtccctc    60
acctgcagtg tctctggtgg ctccatcaac aataataatt actactgggg ctggatccgc   120
cagcccccag ggagggggct ggagtggatt gggagtttct tttatagtgg gcccacctac   180
tacaacccgt ccctcaggag tcgagtcacc atatccgtag acacgtccaa gaaccagttc   240
tccctgaagc tgaactctgt aaccgccgca gacacggcta tattactg tgcgagacag   300
gatgggaact actacccccct ctttgactac tggggccagg gaaccctggt caccgtctcc   360
tca                                                                 363

<210> SEQ ID NO 178
<211> LENGTH: 121
<212> TYPE: PRT
<213> ORGANISM: Artificial Sequence
<220> FEATURE:
<223> OTHER INFORMATION: synthetic

<400> SEQUENCE: 178

Gln Leu Gln Leu Gln Glu Ser Gly Pro Gly Leu Val Lys Pro Ser Glu
1               5                   10                  15

Thr Leu Ser Leu Thr Cys Ser Val Ser Gly Gly Ser Ile Asn Asn Asn
            20                  25                  30

Asn Tyr Tyr Trp Gly Trp Ile Arg Gln Pro Pro Gly Arg Gly Leu Glu
        35                  40                  45

Trp Ile Gly Ser Phe Phe Tyr Ser Gly Pro Thr Tyr Tyr Asn Pro Ser
    50                  55                  60

Leu Arg Ser Arg Val Thr Ile Ser Val Asp Thr Ser Lys Asn Gln Phe
65                  70                  75                  80

Ser Leu Lys Leu Asn Ser Val Thr Ala Ala Asp Thr Ala Ile Tyr Tyr
                85                  90                  95

Cys Ala Arg Gln Asp Gly Asn Tyr Tyr Pro Leu Phe Asp Tyr Trp Gly
            100                 105                 110

Gln Gly Thr Leu Val Thr Val Ser Ser
        115                 120

<210> SEQ ID NO 179
<211> LENGTH: 30
<212> TYPE: DNA
<213> ORGANISM: Artificial Sequence
<220> FEATURE:

<223> OTHER INFORMATION: synthetic

<400> SEQUENCE: 179
ggtggctcca tcaacaataa taattactac                                    30

<210> SEQ ID NO 180
<211> LENGTH: 10
<212> TYPE: PRT
<213> ORGANISM: Artificial Sequence
<220> FEATURE:
<223> OTHER INFORMATION: synthetic

<400> SEQUENCE: 180

Gly Gly Ser Ile Asn Asn Asn Tyr Tyr
1               5                   10

<210> SEQ ID NO 181
<211> LENGTH: 21
<212> TYPE: DNA
<213> ORGANISM: Artificial Sequence
<220> FEATURE:
<223> OTHER INFORMATION: synthetic

<400> SEQUENCE: 181
ttcttttata gtgggcccac c                                             21

<210> SEQ ID NO 182
<211> LENGTH: 7
<212> TYPE: PRT
<213> ORGANISM: Artificial Sequence
<220> FEATURE:
<223> OTHER INFORMATION: synthetic

<400> SEQUENCE: 182

Phe Phe Tyr Ser Gly Pro Thr
1               5

<210> SEQ ID NO 183
<211> LENGTH: 39
<212> TYPE: DNA
<213> ORGANISM: Artificial Sequence
<220> FEATURE:
<223> OTHER INFORMATION: synthetic

<400> SEQUENCE: 183
gcgagacagg atgggaacta ctaccccctc tttgactac                           39

<210> SEQ ID NO 184
<211> LENGTH: 13
<212> TYPE: PRT
<213> ORGANISM: Artificial Sequence
<220> FEATURE:
<223> OTHER INFORMATION: synthetic

<400> SEQUENCE: 184

Ala Arg Gln Asp Gly Asn Tyr Tyr Pro Leu Phe Asp Tyr
1               5                   10

<210> SEQ ID NO 185
<211> LENGTH: 354
<212> TYPE: DNA
<213> ORGANISM: Artificial Sequence
<220> FEATURE:
<223> OTHER INFORMATION: synthetic

<400> SEQUENCE: 185

```
caggtgcagc tgcaggagtc gggcccaggg ctggtgaagc cttcggagac cctgtccctc      60
acctgcactg tctctggtgg ctccatcagt agttactact ggagctggat ccggcagccc     120
ccagggaagg gactggagtg gattgggtat atctattaca gtgggagccc caactacaac     180
ccctccctca agagtcgagt caccatatca gtagacacgt ccaagaacca gttctccctg     240
aagctgacct ctgtgaccgc tgcggacacg gccgtgtatt actgtgcgag atcccttaac     300
tggggacccc cttttgacta ctggggccag ggaaccctgg tcaccgtctc ctca           354
```

```
<210> SEQ ID NO 186
<211> LENGTH: 118
<212> TYPE: PRT
<213> ORGANISM: Artificial Sequence
<220> FEATURE:
<223> OTHER INFORMATION: synthetic

<400> SEQUENCE: 186
```

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Pro Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Thr Ser Val Thr Ala Ala Asp Thr Ala Val Tyr Tyr Cys Ala
                85                  90                  95

Arg Ser Leu Asn Trp Gly Pro Pro Phe Asp Tyr Trp Gly Gln Gly Thr
            100                 105                 110

Leu Val Thr Val Ser Ser
        115

```
<210> SEQ ID NO 187
<211> LENGTH: 24
<212> TYPE: DNA
<213> ORGANISM: Artificial Sequence
<220> FEATURE:
<223> OTHER INFORMATION: synthetic

<400> SEQUENCE: 187
ggtggctcca tcagtagtta ctac                                              24

<210> SEQ ID NO 188
<211> LENGTH: 8
<212> TYPE: PRT
<213> ORGANISM: Artificial Sequence
<220> FEATURE:
<223> OTHER INFORMATION: synthetic

<400> SEQUENCE: 188
```

Gly Gly Ser Ile Ser Ser Tyr Tyr
1               5

```
<210> SEQ ID NO 189
<211> LENGTH: 21
<212> TYPE: DNA
<213> ORGANISM: Artificial Sequence
<220> FEATURE:
<223> OTHER INFORMATION: synthetic
```

<400> SEQUENCE: 189
atctattaca gtgggagccc c                                              21

<210> SEQ ID NO 190
<211> LENGTH: 7
<212> TYPE: PRT
<213> ORGANISM: Artificial Sequence
<220> FEATURE:
<223> OTHER INFORMATION: synthetic

<400> SEQUENCE: 190

Ile Tyr Tyr Ser Gly Ser Pro
1               5

<210> SEQ ID NO 191
<211> LENGTH: 36
<212> TYPE: DNA
<213> ORGANISM: Artificial Sequence
<220> FEATURE:
<223> OTHER INFORMATION: synthetic

<400> SEQUENCE: 191
gcgagatccc ttaactgggg accccctttt gactac                              36

<210> SEQ ID NO 192
<211> LENGTH: 12
<212> TYPE: PRT
<213> ORGANISM: Artificial Sequence
<220> FEATURE:
<223> OTHER INFORMATION: synthetic

<400> SEQUENCE: 192

Ala Arg Ser Leu Asn Trp Gly Pro Pro Phe Asp Tyr
1               5                   10

<210> SEQ ID NO 193
<211> LENGTH: 321
<212> TYPE: DNA
<213> ORGANISM: Artificial Sequence
<220> FEATURE:
<223> OTHER INFORMATION: synthetic

<400> SEQUENCE: 193
gaaatagtga tgacgcagtc tccagccacc ctgtctctgt ctccagggga aagagccacc    60
ctctcctgca gggccagtca gagtgttagc agcaacttag cctggtacca gcaaaaacct   120
ggccaggctc ccaggctcct catctatggt gcatccacca gggccactgg tatcccagcc   180
aggttcagtg gcagtgggtc tgggacagag ttcactctca ccatcagcag cctgcagtct   240
gaagattttg cagttttatta ctgtcagcag tttaataact ggccgtacac ttttggccag   300
gggaccaagc tggagatcaa a                                             321

<210> SEQ ID NO 194
<211> LENGTH: 107
<212> TYPE: PRT
<213> ORGANISM: Artificial Sequence
<220> FEATURE:
<223> OTHER INFORMATION: synthetic

<400> SEQUENCE: 194

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Phe Asn Asn Trp Pro Tyr
                85                  90                  95

Thr Phe Gly Gln Gly Thr Lys Leu Glu Ile Lys
            100                 105

<210> SEQ ID NO 195
<211> LENGTH: 18
<212> TYPE: DNA
<213> ORGANISM: Artificial Sequence
<220> FEATURE:
<223> OTHER INFORMATION: synthetic

<400> SEQUENCE: 195
cagagtgtta gcagcaac                                                18

<210> SEQ ID NO 196
<211> LENGTH: 6
<212> TYPE: PRT
<213> ORGANISM: Artificial Sequence
<220> FEATURE:
<223> OTHER INFORMATION: synthetic

<400> SEQUENCE: 196

Gln Ser Val Ser Ser Asn
1               5

<210> SEQ ID NO 197
<211> LENGTH: 9
<212> TYPE: DNA
<213> ORGANISM: Artificial Sequence
<220> FEATURE:
<223> OTHER INFORMATION: synthetic

<400> SEQUENCE: 197 ggtgcatcc                                                           9

<210> SEQ ID NO 198
<211> LENGTH: 3
<212> TYPE: PRT
<213> ORGANISM: Artificial Sequence
<220> FEATURE:
<223> OTHER INFORMATION: synthetic

<400> SEQUENCE: 198

Gly Ala Ser
1

<210> SEQ ID NO 199
<211> LENGTH: 27
<212> TYPE: DNA
<213> ORGANISM: Artificial Sequence
<220> FEATURE:
<223> OTHER INFORMATION: synthetic

<400> SEQUENCE: 199
cagcagttta taactggcc gtacact                                        27

<210> SEQ ID NO 200
<211> LENGTH: 9
<212> TYPE: PRT
<213> ORGANISM: Artificial Sequence
<220> FEATURE:
<223> OTHER INFORMATION: synthetic

<400> SEQUENCE: 200

Gln Gln Phe Asn Asn Trp Pro Tyr Thr
1               5

<210> SEQ ID NO 201
<211> LENGTH: 375
<212> TYPE: DNA
<213> ORGANISM: Artificial Sequence
<220> FEATURE:
<223> OTHER INFORMATION: synthetic

<400> SEQUENCE: 201

```
gaggtgcagc tgttggagtc tgggggaggc ttggtacagc ctgggggtc cctgagactc      60
tcctgtccag cctctggatt cacctttagc aactatgcca tgacctgggt ccgccaggct    120
ccagggaagg ggctggagtg ggtctcagct attagtggta gtggtgctac cacaaagtac    180
gcagactccg tgaagggccg gttcaccatt tccagagaca attccaggaa tacgctatat    240
ctgcaaatga acagtctgag agccgaggac acggccgtat attactgtgc aaggggggt    300
tcggggagtt atttccctta ctactactac ggtttggacg tctggggcca agggaccacg    360
gtcaccgtct cctca                                                    375
```

<210> SEQ ID NO 202
<211> LENGTH: 125
<212> TYPE: PRT
<213> ORGANISM: Artificial Sequence
<220> FEATURE:
<223> OTHER INFORMATION: synthetic

<400> SEQUENCE: 202

Glu Val Gln Leu Leu Glu Ser Gly Gly Gly Leu Val Gln Pro Gly Gly
1               5                   10                  15

Ser Leu Arg Leu Ser Cys Pro Ala Ser Gly Phe Thr Phe Ser Asn Tyr
            20                  25                  30

Ala Met Thr Trp Val Arg Gln Ala Pro Gly Lys Gly Leu Glu Trp Val
        35                  40                  45

Ser Ala Ile Ser Gly Ser Gly Ala Thr Thr Lys Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Ser Gly Ser Tyr Phe Pro Tyr Tyr Tyr Gly Leu
            100                 105                 110

Asp Val Trp Gly Gln Gly Thr Thr Val Thr Val Ser Ser
        115                 120                 125

<210> SEQ ID NO 203
<211> LENGTH: 24
<212> TYPE: DNA
<213> ORGANISM: Artificial Sequence
<220> FEATURE:
<223> OTHER INFORMATION: synthetic

<400> SEQUENCE: 203
ggattcacct ttagcaacta tgcc                                          24

<210> SEQ ID NO 204
<211> LENGTH: 8
<212> TYPE: PRT
<213> ORGANISM: Artificial Sequence
<220> FEATURE:
<223> OTHER INFORMATION: synthetic

<400> SEQUENCE: 204

Gly Phe Thr Phe Ser Asn Tyr Ala
1               5

<210> SEQ ID NO 205
<211> LENGTH: 24
<212> TYPE: DNA
<213> ORGANISM: Artificial Sequence
<220> FEATURE:
<223> OTHER INFORMATION: synthetic

<400> SEQUENCE: 205
attagtggta gtggtgctac caca                                          24

<210> SEQ ID NO 206
<211> LENGTH: 8
<212> TYPE: PRT
<213> ORGANISM: Artificial Sequence
<220> FEATURE:
<223> OTHER INFORMATION: synthetic

<400> SEQUENCE: 206

Ile Ser Gly Ser Gly Ala Thr Thr
1               5

<210> SEQ ID NO 207
<211> LENGTH: 54
<212> TYPE: DNA
<213> ORGANISM: Artificial Sequence
<220> FEATURE:
<223> OTHER INFORMATION: synthetic

<400> SEQUENCE: 207
gcgaaggggg gttcggggag ttatttccct tactactact acggtttgga cgtc         54

<210> SEQ ID NO 208
<211> LENGTH: 18
<212> TYPE: PRT
<213> ORGANISM: Artificial Sequence
<220> FEATURE:
<223> OTHER INFORMATION: synthetic

<400> SEQUENCE: 208

Ala Lys Gly Gly Ser Gly Ser Tyr Phe Pro Tyr Tyr Tyr Tyr Gly Leu
1               5                   10                  15

Asp Val

<210> SEQ ID NO 209
<211> LENGTH: 318
<212> TYPE: DNA
<213> ORGANISM: Artificial Sequence
<220> FEATURE:
<223> OTHER INFORMATION: synthetic

<400> SEQUENCE: 209
gaaatagtga tgacgcagtc tccagccacc ctgtctgtgt ctccagggga tagtgccacc   60

```
ctctcctgca gggccagtca gactgttagc agcaacttag cctggtacca gcagaaacct    120
ggccaggctc ccaggctcct catctatggt gcatccacca gggccactgg tatcccagcc    180
aggttcagtg gcagtggctc tgggacagag ttcactctca ccatcagcag cctgcagtct    240
gaagattttg cagtttatta ctgtcagcag tattataact ggtggacgtt cggccaaggg    300
accaaggtgg aaatcaaa                                                  318
```

```
<210> SEQ ID NO 210
<211> LENGTH: 106
<212> TYPE: PRT
<213> ORGANISM: Artificial Sequence
<220> FEATURE:
<223> OTHER INFORMATION: synthetic

<400> SEQUENCE: 210

Glu Ile Val Met Thr Gln Ser Pro Ala Thr Leu Ser Val Ser Pro Gly
1               5                   10                  15

Asp Ser Ala Thr Leu Ser Cys Arg Ala Ser Gln Thr Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Tyr Asn Trp Trp Thr
                85                  90                  95

Phe Gly Gln Gly Thr Lys Val Glu Ile Lys
            100                 105
```

```
<210> SEQ ID NO 211
<211> LENGTH: 18
<212> TYPE: DNA
<213> ORGANISM: Artificial Sequence
<220> FEATURE:
<223> OTHER INFORMATION: synthetic

<400> SEQUENCE: 211
cagactgtta gcagcaac                                                   18
```

```
<210> SEQ ID NO 212
<211> LENGTH: 6
<212> TYPE: PRT
<213> ORGANISM: Artificial Sequence
<220> FEATURE:
<223> OTHER INFORMATION: synthetic

<400> SEQUENCE: 212

Gln Thr Val Ser Ser Asn
1               5
```

```
<210> SEQ ID NO 213
<211> LENGTH: 9
<212> TYPE: DNA
<213> ORGANISM: Artificial Sequence
<220> FEATURE:
<223> OTHER INFORMATION: synthetic

<400> SEQUENCE: 213 ggtgcatcc                                                              9
```

<210> SEQ ID NO 214
<211> LENGTH: 3
<212> TYPE: PRT
<213> ORGANISM: Artificial Sequence
<220> FEATURE:
<223> OTHER INFORMATION: synthetic

<400> SEQUENCE: 214

Gly Ala Ser
1

<210> SEQ ID NO 215
<211> LENGTH: 24
<212> TYPE: DNA
<213> ORGANISM: Artificial Sequence
<220> FEATURE:
<223> OTHER INFORMATION: synthetic

<400> SEQUENCE: 215
cagcagtatt ataactggtg gacg                                              24

<210> SEQ ID NO 216
<211> LENGTH: 8
<212> TYPE: PRT
<213> ORGANISM: Artificial Sequence
<220> FEATURE:
<223> OTHER INFORMATION: synthetic

<400> SEQUENCE: 216

Gln Gln Tyr Tyr Asn Trp Trp Thr
1               5

<210> SEQ ID NO 217
<211> LENGTH: 354
<212> TYPE: DNA
<213> ORGANISM: Artificial Sequence
<220> FEATURE:
<223> OTHER INFORMATION: synthetic

<400> SEQUENCE: 217
gaggtgcagc tgttggagtc tgggggaggc ttggtacagc ctggggggtc cctgagactc        60
tcctgtgcag cctctggatt cacctttagc agctatgcca tgagctgggt ccgccaggct       120
ccagggaagg ggctggagtg ggtctcagct attagtggtc gtggtggtaa cacatactac       180
gcagactccg tgaagggccg gttcaccatc tccagagaca attccaagaa cacgctgttt       240
ctgcaaatga acaccctgag agccgaggac acggccgtat attactgtgc gaaagatagg       300
ggttttgggt tcttcgatat ctggggccgt ggcaccctgg ccactgtctc ctca             354

<210> SEQ ID NO 218
<211> LENGTH: 118
<212> TYPE: PRT
<213> ORGANISM: Artificial Sequence
<220> FEATURE:
<223> OTHER INFORMATION: synthetic

<400> SEQUENCE: 218

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Arg Gly Gly Asn Thr Tyr Tyr Ala Asp Ser Val
            50                  55                  60

Lys Gly Arg Phe Thr Ile Ser Arg Asp Asn Ser Lys Asn Thr Leu Phe
 65                  70                  75                  80

Leu Gln Met Asn Thr Leu Arg Ala Glu Asp Thr Ala Val Tyr Tyr Cys
                 85                  90                  95

Ala Lys Asp Arg Gly Phe Gly Phe Phe Asp Ile Trp Gly Arg Gly Thr
            100                 105                 110

Leu Ala Thr Val Ser Ser
        115

<210> SEQ ID NO 219
<211> LENGTH: 24
<212> TYPE: DNA
<213> ORGANISM: Artificial Sequence
<220> FEATURE:
<223> OTHER INFORMATION: synthetic

<400> SEQUENCE: 219
ggattcacct ttagcagcta tgcc                                    24

<210> SEQ ID NO 220
<211> LENGTH: 8
<212> TYPE: PRT
<213> ORGANISM: Artificial Sequence
<220> FEATURE:
<223> OTHER INFORMATION: synthetic

<400> SEQUENCE: 220

Gly Phe Thr Phe Ser Ser Tyr Ala
 1               5

<210> SEQ ID NO 221
<211> LENGTH: 24
<212> TYPE: DNA
<213> ORGANISM: Artificial Sequence
<220> FEATURE:
<223> OTHER INFORMATION: synthetic

<400> SEQUENCE: 221
attagtggtc gtggtggtaa caca                                    24

<210> SEQ ID NO 222
<211> LENGTH: 8
<212> TYPE: PRT
<213> ORGANISM: Artificial Sequence
<220> FEATURE:
<223> OTHER INFORMATION: synthetic

<400> SEQUENCE: 222

Ile Ser Gly Arg Gly Gly Asn Thr
 1               5

<210> SEQ ID NO 223
<211> LENGTH: 33
<212> TYPE: DNA
<213> ORGANISM: Artificial Sequence
<220> FEATURE:
<223> OTHER INFORMATION: synthetic

<400> SEQUENCE: 223
gcgaaagata ggggtttttgg gttcttcgat atc                          33

<210> SEQ ID NO 224

```
<211> LENGTH: 11
<212> TYPE: PRT
<213> ORGANISM: Artificial Sequence
<220> FEATURE:
<223> OTHER INFORMATION: synthetic

<400> SEQUENCE: 224

Ala Lys Asp Arg Gly Phe Gly Phe Phe Asp Ile
1               5                   10

<210> SEQ ID NO 225
<211> LENGTH: 321
<212> TYPE: DNA
<213> ORGANISM: Artificial Sequence
<220> FEATURE:
<223> OTHER INFORMATION: synthetic

<400> SEQUENCE: 225
gacatccaga tgacccagtc tccatcctcc ctgtctgcat ctgtaggaga cagagtcacc      60
atcacttgcc aggcgagtca ggacattagt aactatttaa attggtatca gcagaaacca     120
gggaaagccc ctaagttcct gatctacgat gcatccaatt tggaaacagg ggtcccatca     180
aggttcagtg gaagtggatc tgggacagat tttactttca ccatcagcag cctgcagcct     240
gaagatattg caacatatta ctgtcaacag tatgataatc tcccattcac tttcggccct     300
gggaccaaaa taaatatcaa a                                                321

<210> SEQ ID NO 226
<211> LENGTH: 107
<212> TYPE: PRT
<213> ORGANISM: Artificial Sequence
<220> FEATURE:
<223> OTHER INFORMATION: synthetic

<400> SEQUENCE: 226

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Phe Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Phe
                85                  90                  95

Thr Phe Gly Pro Gly Thr Lys Ile Asn Ile Lys
            100                 105

<210> SEQ ID NO 227
<211> LENGTH: 18
<212> TYPE: DNA
<213> ORGANISM: Artificial Sequence
<220> FEATURE:
<223> OTHER INFORMATION: synthetic

<400> SEQUENCE: 227
caggacatta gtaactat                                                     18

<210> SEQ ID NO 228
<211> LENGTH: 6
```

<212> TYPE: PRT
<213> ORGANISM: Artificial Sequence
<220> FEATURE:
<223> OTHER INFORMATION: synthetic

<400> SEQUENCE: 228

Gln Asp Ile Ser Asn Tyr
1               5

<210> SEQ ID NO 229
<211> LENGTH: 9
<212> TYPE: DNA
<213> ORGANISM: Artificial Sequence
<220> FEATURE:
<223> OTHER INFORMATION: synthetic

<400> SEQUENCE: 229 gatgcatcc                                                                 9

<210> SEQ ID NO 230
<211> LENGTH: 3
<212> TYPE: PRT
<213> ORGANISM: Artificial Sequence
<220> FEATURE:
<223> OTHER INFORMATION: synthetic

<400> SEQUENCE: 230

Asp Ala Ser
1

<210> SEQ ID NO 231
<211> LENGTH: 27
<212> TYPE: DNA
<213> ORGANISM: Artificial Sequence
<220> FEATURE:
<223> OTHER INFORMATION: synthetic

<400> SEQUENCE: 231
caacagtatg ataatctccc attcact                                            27

<210> SEQ ID NO 232
<211> LENGTH: 9
<212> TYPE: PRT
<213> ORGANISM: Artificial Sequence
<220> FEATURE:
<223> OTHER INFORMATION: synthetic

<400> SEQUENCE: 232

Gln Gln Tyr Asp Asn Leu Pro Phe Thr
1               5

<210> SEQ ID NO 233
<211> LENGTH: 351
<212> TYPE: DNA
<213> ORGANISM: Artificial Sequence
<220> FEATURE:
<223> OTHER INFORMATION: synthetic

<400> SEQUENCE: 233
gaggtgcagc tgttggagtc tgggggaggc ttggtacagc ctgggggtc cctgagactc         60 tcctgtgcag cctctggatt cacctttagc agctatgcca tgagctgggt ccgccaggct       120
ccagggaagg ggctggagtg ggtctcagct attagtggta gtggtagtag cacatactac       180
gcagactccg tgaagggccg gttcaccatc tccagagaca attccaagaa cacgctgttt       240
ctgcaaatga acagcctgag agccgaggac acggccgtct attactgtgc ggaagggga       300 gacgtggatt ttgactactg gggccaggga accctggtca ccgtctcctc a    351

<210> SEQ ID NO 234
<211> LENGTH: 117
<212> TYPE: PRT
<213> ORGANISM: Artificial Sequence
<220> FEATURE:
<223> OTHER INFORMATION: synthetic

<400> SEQUENCE: 234

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Ser Ser Thr Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Glu Gly Gly Asp Val Asp Phe Asp Tyr Trp Gly Gln Gly Thr Leu
            100                 105                 110

Val Thr Val Ser Ser
        115

<210> SEQ ID NO 235
<211> LENGTH: 24
<212> TYPE: DNA
<213> ORGANISM: Artificial Sequence
<220> FEATURE:
<223> OTHER INFORMATION: synthetic

<400> SEQUENCE: 235
ggattcacct ttagcagcta tgcc    24

<210> SEQ ID NO 236
<211> LENGTH: 8
<212> TYPE: PRT
<213> ORGANISM: Artificial Sequence
<220> FEATURE:
<223> OTHER INFORMATION: synthetic

<400> SEQUENCE: 236

Gly Phe Thr Phe Ser Ser Tyr Ala
1               5

<210> SEQ ID NO 237
<211> LENGTH: 24
<212> TYPE: DNA
<213> ORGANISM: Artificial Sequence
<220> FEATURE:
<223> OTHER INFORMATION: synthetic

<400> SEQUENCE: 237
attagtggta gtggtagtag caca    24

<210> SEQ ID NO 238
<211> LENGTH: 8
<212> TYPE: PRT
<213> ORGANISM: Artificial Sequence
<220> FEATURE:
<223> OTHER INFORMATION: synthetic

<400> SEQUENCE: 238

Ile Ser Gly Ser Gly Ser Ser Thr
1               5

<210> SEQ ID NO 239
<211> LENGTH: 30
<212> TYPE: DNA
<213> ORGANISM: Artificial Sequence
<220> FEATURE:
<223> OTHER INFORMATION: synthetic

<400> SEQUENCE: 239
gcggaagggg gagacgtgga ttttgactac                                       30

<210> SEQ ID NO 240
<211> LENGTH: 10
<212> TYPE: PRT
<213> ORGANISM: Artificial Sequence
<220> FEATURE:
<223> OTHER INFORMATION: synthetic

<400> SEQUENCE: 240

Ala Glu Gly Gly Asp Val Asp Phe Asp Tyr
1               5                   10

<210> SEQ ID NO 241
<211> LENGTH: 324
<212> TYPE: DNA
<213> ORGANISM: Artificial Sequence
<220> FEATURE:
<223> OTHER INFORMATION: synthetic

<400> SEQUENCE: 241
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcaacag agttacagta cccctccgat caccttcggc     300
caagggacac gactggagat taaa                                            324

<210> SEQ ID NO 242
<211> LENGTH: 108
<212> TYPE: PRT
<213> ORGANISM: Artificial Sequence
<220> FEATURE:
<223> OTHER INFORMATION: synthetic

<400> SEQUENCE: 242

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
            85                  90                  95

Ile Thr Phe Gly Gln Gly Thr Arg Leu Glu Ile Lys
            100                 105

<210> SEQ ID NO 243
<211> LENGTH: 18
<212> TYPE: DNA
<213> ORGANISM: Artificial Sequence
<220> FEATURE:
<223> OTHER INFORMATION: synthetic

<400> SEQUENCE: 243
cagagcatta gcagctat                                                 18

<210> SEQ ID NO 244
<211> LENGTH: 6
<212> TYPE: PRT
<213> ORGANISM: Artificial Sequence
<220> FEATURE:
<223> OTHER INFORMATION: synthetic

<400> SEQUENCE: 244

Gln Ser Ile Ser Ser Tyr
1               5

<210> SEQ ID NO 245
<211> LENGTH: 9
<212> TYPE: DNA
<213> ORGANISM: Artificial Sequence
<220> FEATURE:
<223> OTHER INFORMATION: synthetic

<400> SEQUENCE: 245 gctgcatcc                                                           9

<210> SEQ ID NO 246
<211> LENGTH: 3
<212> TYPE: PRT
<213> ORGANISM: Artificial Sequence
<220> FEATURE:
<223> OTHER INFORMATION: synthetic

<400> SEQUENCE: 246

Ala Ala Ser
1

<210> SEQ ID NO 247
<211> LENGTH: 30
<212> TYPE: DNA
<213> ORGANISM: Artificial Sequence
<220> FEATURE:
<223> OTHER INFORMATION: synthetic

<400> SEQUENCE: 247
caacagagtt acagtacccc tccgatcacc                                    30

<210> SEQ ID NO 248
<211> LENGTH: 10
<212> TYPE: PRT
<213> ORGANISM: Artificial Sequence
<220> FEATURE:
<223> OTHER INFORMATION: synthetic

<400> SEQUENCE: 248

Gln Gln Ser Tyr Ser Thr Pro Pro Ile Thr
1               5                   10

<210> SEQ ID NO 249
<211> LENGTH: 348
<212> TYPE: DNA
<213> ORGANISM: Artificial Sequence
<220> FEATURE:
<223> OTHER INFORMATION: synthetic

<400> SEQUENCE: 249
caggtgcagc tgcaggagtc gggcccagga ctggtgaagc cttcggagac cctgtccctc      60
acctgcactg tctctggtgg ctccatcagt agttactact ggagctggat ccggcagccc     120
ccagggaagg gactggaatg gattgggtac atctattaca gtgggagcgc caactacaac     180
ccctccctca gagtcgagt caccatatca gtagacacgt ccaagaacca gttctccctg     240
aagctaagct ctgtgaccgc tgcggacacg gccgtgtatt actgtgtgag agaccgggac     300
ctactccttg accactgggg ccagggaacc ctggtcaccg tctcctca                  348

<210> SEQ ID NO 250
<211> LENGTH: 116
<212> TYPE: PRT
<213> ORGANISM: Artificial Sequence
<220> FEATURE:
<223> OTHER INFORMATION: synthetic

<400> SEQUENCE: 250

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
                20                  25                  30

Tyr Trp Ser Trp Ile Arg Gln Pro Pro Gly Lys Gly Leu Glu Trp Ile
            35                  40                  45

Gly Tyr Ile Tyr Tyr Ser Gly Ser Ala Asn Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Val
                85                  90                  95

Arg Asp Arg Asp Leu Leu Leu Asp His Trp Gly Gln Gly Thr Leu Val
            100                 105                 110

Thr Val Ser Ser
        115

<210> SEQ ID NO 251
<211> LENGTH: 24
<212> TYPE: DNA
<213> ORGANISM: Artificial Sequence
<220> FEATURE:
<223> OTHER INFORMATION: synthetic

<400> SEQUENCE: 251
ggtggctcca tcagtagtta ctac                                            24

<210> SEQ ID NO 252
<211> LENGTH: 8
<212> TYPE: PRT
<213> ORGANISM: Artificial Sequence
<220> FEATURE:
<223> OTHER INFORMATION: synthetic

<400> SEQUENCE: 252

Gly Gly Ser Ile Ser Ser Tyr Tyr
1               5

<210> SEQ ID NO 253
<211> LENGTH: 21
<212> TYPE: DNA
<213> ORGANISM: Artificial Sequence
<220> FEATURE:
<223> OTHER INFORMATION: synthetic

<400> SEQUENCE: 253
atctattaca gtgggagcgc c                                              21

<210> SEQ ID NO 254
<211> LENGTH: 7
<212> TYPE: PRT
<213> ORGANISM: Artificial Sequence
<220> FEATURE:
<223> OTHER INFORMATION: synthetic

<400> SEQUENCE: 254

Ile Tyr Tyr Ser Gly Ser Ala
1               5

<210> SEQ ID NO 255
<211> LENGTH: 30
<212> TYPE: DNA
<213> ORGANISM: Artificial Sequence
<220> FEATURE:
<223> OTHER INFORMATION: synthetic

<400> SEQUENCE: 255
gtgagagacc gggacctact ccttgaccac                                     30

<210> SEQ ID NO 256
<211> LENGTH: 10
<212> TYPE: PRT
<213> ORGANISM: Artificial Sequence
<220> FEATURE:
<223> OTHER INFORMATION: synthetic

<400> SEQUENCE: 256

Val Arg Asp Arg Asp Leu Leu Leu Asp His
1               5                   10

<210> SEQ ID NO 257
<211> LENGTH: 321
<212> TYPE: DNA
<213> ORGANISM: Artificial Sequence
<220> FEATURE:
<223> OTHER INFORMATION: synthetic

<400> SEQUENCE: 257
gaaatagtga tgacgcagtc tccagccacc ctgtctgtgt ctccagggaa aagagccacc     60
ctctcctgca gggccagtca gagtgttagc agcaacttag cctggtacca gcagaaacct    120
ggccaggctc ccaggctcct catctatggt gcatccacca ggaccactgg tttcccagcc    180
aggttcagtg gcagtgggtc tgggacagac ttcactctca ccatcagcag cctgcagtct    240
gaagattttg cagtttatta ctgtcagcag tataataact ggccgtacac ttttggccag    300
gggaccatgc tggagatcaa a                                             321

<210> SEQ ID NO 258

```
<211> LENGTH: 107
<212> TYPE: PRT
<213> ORGANISM: Artificial Sequence
<220> FEATURE:
<223> OTHER INFORMATION: synthetic

<400> SEQUENCE: 258

Glu Ile Val Met Thr Gln Ser Pro Ala Thr Leu Ser Val Ser Pro Gly
1               5                   10                  15

Lys Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Thr Thr Gly Phe Pro Ala Arg Phe Ser Gly
50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Tyr
                85                  90                  95

Thr Phe Gly Gln Gly Thr Met Leu Glu Ile Lys
            100                 105

<210> SEQ ID NO 259
<211> LENGTH: 18
<212> TYPE: DNA
<213> ORGANISM: Artificial Sequence
<220> FEATURE:
<223> OTHER INFORMATION: synthetic

<400> SEQUENCE: 259
cagagtgtta gcagcaac                                                 18

<210> SEQ ID NO 260
<211> LENGTH: 6
<212> TYPE: PRT
<213> ORGANISM: Artificial Sequence
<220> FEATURE:
<223> OTHER INFORMATION: synthetic

<400> SEQUENCE: 260

Gln Ser Val Ser Ser Asn
1               5

<210> SEQ ID NO 261
<211> LENGTH: 9
<212> TYPE: DNA
<213> ORGANISM: Artificial Sequence
<220> FEATURE:
<223> OTHER INFORMATION: synthetic

<400> SEQUENCE: 261 ggtgcatcc                                                            9

<210> SEQ ID NO 262
<211> LENGTH: 3
<212> TYPE: PRT
<213> ORGANISM: Artificial Sequence
<220> FEATURE:
<223> OTHER INFORMATION: synthetic

<400> SEQUENCE: 262

Gly Ala Ser
1
```

<210> SEQ ID NO 263
<211> LENGTH: 27
<212> TYPE: DNA
<213> ORGANISM: Artificial Sequence
<220> FEATURE:
<223> OTHER INFORMATION: synthetic

<400> SEQUENCE: 263
cagcagtata ataactggcc gtacact                                          27

<210> SEQ ID NO 264
<211> LENGTH: 9
<212> TYPE: PRT
<213> ORGANISM: Artificial Sequence
<220> FEATURE:
<223> OTHER INFORMATION: synthetic

<400> SEQUENCE: 264

Gln Gln Tyr Asn Asn Trp Pro Tyr Thr
1               5

<210> SEQ ID NO 265
<211> LENGTH: 387
<212> TYPE: DNA
<213> ORGANISM: Artificial Sequence
<220> FEATURE:
<223> OTHER INFORMATION: synthetic

<400> SEQUENCE: 265
caggtccagc tggtgcagtc tggggctgag gtgaagaagc ctgggtcctc ggtgaaggtc       60
tcctgcaagg cttctggagg caccttcagc acttatgcta tcagctgggt gcgacaggcc     120
cctggacaag gcttgagtg gatgggaggg atcatccctt tctttggtac agcaaactac      180
gcacagaagt tccagggcag agtcacgatt accacggacg aatccacgag cacagcctac     240
atggagttga gcagcctgag atctgaggac acggccgtgt attactgtgc gagagaggga     300
acgtattacg attctttgac tggttattac acccactact accgtatgga cgtctggggc     360
caagggacca cggtcaccgt ctcctca                                        387

<210> SEQ ID NO 266
<211> LENGTH: 129
<212> TYPE: PRT
<213> ORGANISM: Artificial Sequence
<220> FEATURE:
<223> OTHER INFORMATION: synthetic

<400> SEQUENCE: 266

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
                20                  25                  30

Ala Ile Ser Trp Val Arg Gln Ala Pro Gly Gln Gly Leu Glu Trp Met
            35                  40                  45

Gly Gly Ile Ile Pro Phe Phe Gly Thr Ala Asn Tyr Ala Gln Lys Phe
        50                  55                  60

Gln Gly Arg Val Thr Ile Thr Thr Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Thr Tyr Tyr Asp Ser Leu Thr Gly Tyr Tyr Thr His
                100                 105                 110

Tyr Tyr Arg Met Asp Val Trp Gly Gln Gly Thr Thr Val Thr Val Ser
        115                 120                 125

Ser

<210> SEQ ID NO 267
<211> LENGTH: 24
<212> TYPE: DNA
<213> ORGANISM: Artificial Sequence
<220> FEATURE:
<223> OTHER INFORMATION: synthetic

<400> SEQUENCE: 267
ggaggcacct tcagcactta tgct                                          24

<210> SEQ ID NO 268
<211> LENGTH: 8
<212> TYPE: PRT
<213> ORGANISM: Artificial Sequence
<220> FEATURE:
<223> OTHER INFORMATION: synthetic

<400> SEQUENCE: 268

Gly Gly Thr Phe Ser Thr Tyr Ala
1               5

<210> SEQ ID NO 269
<211> LENGTH: 24
<212> TYPE: DNA
<213> ORGANISM: Artificial Sequence
<220> FEATURE:
<223> OTHER INFORMATION: synthetic

<400> SEQUENCE: 269
atcatccctt tctttggtac agca                                          24

<210> SEQ ID NO 270
<211> LENGTH: 8
<212> TYPE: PRT
<213> ORGANISM: Artificial Sequence
<220> FEATURE:
<223> OTHER INFORMATION: synthetic

<400> SEQUENCE: 270

Ile Ile Pro Phe Phe Gly Thr Ala
1               5

<210> SEQ ID NO 271
<211> LENGTH: 66
<212> TYPE: DNA
<213> ORGANISM: Artificial Sequence
<220> FEATURE:
<223> OTHER INFORMATION: synthetic

<400> SEQUENCE: 271
gcgagagagg gaacgtatta cgattctttg actggttatt acacccacta ctaccgtatg    60
gacgtc                                                              66

<210> SEQ ID NO 272
<211> LENGTH: 22
<212> TYPE: PRT
<213> ORGANISM: Artificial Sequence
<220> FEATURE:
<223> OTHER INFORMATION: synthetic

<400> SEQUENCE: 272

Ala Arg Glu Gly Thr Tyr Tyr Asp Ser Leu Thr Gly Tyr Tyr Thr His
1               5                   10                  15

Tyr Tyr Arg Met Asp Val
            20

<210> SEQ ID NO 273
<211> LENGTH: 324
<212> TYPE: DNA
<213> ORGANISM: Artificial Sequence
<220> FEATURE:
<223> OTHER INFORMATION: synthetic

<400> SEQUENCE: 273
gacatccaga tgacccagtc tccatcctcc ctgtctgcat ctgtgggaga cagagtcacc      60
atcacttgcc gggcaagtca gaccattagc agctatttaa attggtatca gcagaaacca     120
gggaaagccc ctaagctcct gatctatgct gcatccagtt tgcaaagtgg ggtcccatca     180
aggttcagtg gcagtgggtc tgggacagat ttcactctca ccatcagcag tctgcaacct     240
gaagattttg cgacttacta ctgtcaacag agttacagta cccctccgat caccttcggc     300
caagggacac gactggagat taaa                                            324

<210> SEQ ID NO 274
<211> LENGTH: 108
<212> TYPE: PRT
<213> ORGANISM: Artificial Sequence
<220> FEATURE:
<223> OTHER INFORMATION: synthetic

<400> SEQUENCE: 274

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 275
<211> LENGTH: 18
<212> TYPE: DNA
<213> ORGANISM: Artificial Sequence
<220> FEATURE:
<223> OTHER INFORMATION: synthetic

<400> SEQUENCE: 275
cagaccatta gcagctat                                                    18

<210> SEQ ID NO 276
<211> LENGTH: 6
<212> TYPE: PRT
<213> ORGANISM: Artificial Sequence
<220> FEATURE:
<223> OTHER INFORMATION: synthetic

<400> SEQUENCE: 276

Gln Thr Ile Ser Ser Tyr
1               5

<210> SEQ ID NO 277
<211> LENGTH: 9
<212> TYPE: DNA
<213> ORGANISM: Artificial Sequence
<220> FEATURE:
<223> OTHER INFORMATION: synthetic

<400> SEQUENCE: 277 gctgcatcc                                                                9

<210> SEQ ID NO 278
<211> LENGTH: 3
<212> TYPE: PRT
<213> ORGANISM: Artificial Sequence
<220> FEATURE:
<223> OTHER INFORMATION: synthetic

<400> SEQUENCE: 278

Ala Ala Ser
1

<210> SEQ ID NO 279
<211> LENGTH: 30
<212> TYPE: DNA
<213> ORGANISM: Artificial Sequence
<220> FEATURE:
<223> OTHER INFORMATION: synthetic

<400> SEQUENCE: 279
caacagagtt acagtaccccc tccgatcacc                                         30

<210> SEQ ID NO 280
<211> LENGTH: 10
<212> TYPE: PRT
<213> ORGANISM: Artificial Sequence
<220> FEATURE:
<223> OTHER INFORMATION: synthetic

<400> SEQUENCE: 280

Gln Gln Ser Tyr Ser Thr Pro Pro Ile Thr
1               5                   10

<210> SEQ ID NO 281
<211> LENGTH: 381
<212> TYPE: DNA
<213> ORGANISM: Artificial Sequence
<220> FEATURE:
<223> OTHER INFORMATION: synthetic

<400> SEQUENCE: 281
caggtccagc tggtgcagtc tggggctgag gtgaagaagc ctgggtcctc ggtgaaggtc          60
tcctgcaagg tttctggagt caccttcagc agctatgcta tcagctgggt gcgacaggcc        120
cctggacaag gcttgagtg gatgggaggg atcatcccct tctttggtac agcaagctac         180
gcacagaagt tccagggcag agtcacggtt accacggacg aatccacgag cacagcctac        240
atggaggtga gcagcctgag atctgaggac acggccgtgt attactgtgc gagagataat        300
ccggaactaa ctaaggaggg gtactaccac tactacgcta tggacgtctg gggccaaggg        360
accacggtca ccgtctcctc a                                                  381

<210> SEQ ID NO 282
<211> LENGTH: 127
<212> TYPE: PRT
<213> ORGANISM: Artificial Sequence
<220> FEATURE:
<223> OTHER INFORMATION: synthetic

<400> SEQUENCE: 282

Gln Val Gln Leu Val Gln Ser Gly Ala Glu Val Lys Lys Pro Gly Ser
1               5                   10                  15

Ser Val Lys Val Ser Cys Lys Val Ser Gly Val Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Phe Phe Gly Thr Ala Ser Tyr Ala Gln Lys Phe
    50                  55                  60

Gln Gly Arg Val Thr Val Thr Thr Asp Glu Ser Thr Ser Thr Ala Tyr
65                  70                  75                  80

Met Glu Val Ser Ser Leu Arg Ser Glu Asp Thr Ala Val Tyr Tyr Cys
                85                  90                  95

Ala Arg Asp Asn Pro Glu Leu Thr Lys Glu Gly Tyr Tyr His Tyr Tyr
            100                 105                 110

Ala Met Asp Val Trp Gly Gln Gly Thr Thr Val Thr Val Ser Ser
        115                 120                 125

<210> SEQ ID NO 283
<211> LENGTH: 24
<212> TYPE: DNA
<213> ORGANISM: Artificial Sequence
<220> FEATURE:
<223> OTHER INFORMATION: synthetic

<400> SEQUENCE: 283
ggagtcacct tcagcagcta tgct                                          24

<210> SEQ ID NO 284
<211> LENGTH: 8
<212> TYPE: PRT
<213> ORGANISM: Artificial Sequence
<220> FEATURE:
<223> OTHER INFORMATION: synthetic

<400> SEQUENCE: 284

Gly Val Thr Phe Ser Ser Tyr Ala
1               5

<210> SEQ ID NO 285
<211> LENGTH: 24
<212> TYPE: DNA
<213> ORGANISM: Artificial Sequence
<220> FEATURE:
<223> OTHER INFORMATION: synthetic

<400> SEQUENCE: 285
atcatccctt tctttggtac agca                                          24

<210> SEQ ID NO 286
<211> LENGTH: 8
<212> TYPE: PRT
<213> ORGANISM: Artificial Sequence
<220> FEATURE:
<223> OTHER INFORMATION: synthetic

<400> SEQUENCE: 286

Ile Ile Pro Phe Phe Gly Thr Ala
1               5

<210> SEQ ID NO 287
<211> LENGTH: 60
<212> TYPE: DNA
<213> ORGANISM: Artificial Sequence
<220> FEATURE:
<223> OTHER INFORMATION: synthetic

<400> SEQUENCE: 287
gcgagagata atccggaact aactaaggag gggtactacc actactacgc tatggacgtc    60

<210> SEQ ID NO 288
<211> LENGTH: 20
<212> TYPE: PRT
<213> ORGANISM: Artificial Sequence
<220> FEATURE:
<223> OTHER INFORMATION: synthetic

<400> SEQUENCE: 288

Ala Arg Asp Asn Pro Glu Leu Thr Lys Glu Gly Tyr Tyr His Tyr Tyr
1               5                   10                  15

Ala Met Asp Val
            20

<210> SEQ ID NO 289
<211> LENGTH: 324
<212> TYPE: DNA
<213> ORGANISM: Artificial Sequence
<220> FEATURE:
<223> OTHER INFORMATION: synthetic

<400> SEQUENCE: 289
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacagta cccctccgat caccttcggc   300
caagggacac gactggagat taaa                                          324

<210> SEQ ID NO 290
<211> LENGTH: 108
<212> TYPE: PRT
<213> ORGANISM: Artificial Sequence
<220> FEATURE:
<223> OTHER INFORMATION: synthetic

<400> SEQUENCE: 290

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro

```
                65                  70                  75                  80
Glu Asp Phe Ala Thr Tyr Tyr Cys Gln Gln Ser Tyr Ser Thr Pro Pro
                    85                  90                  95
Ile Thr Phe Gly Gln Gly Thr Arg Leu Glu Ile Lys
                100                 105
```

<210> SEQ ID NO 291
<211> LENGTH: 18
<212> TYPE: DNA
<213> ORGANISM: Artificial Sequence
<220> FEATURE:
<223> OTHER INFORMATION: synthetic

<400> SEQUENCE: 291
cagagcatta gcagctat                                                 18

<210> SEQ ID NO 292
<211> LENGTH: 6
<212> TYPE: PRT
<213> ORGANISM: Artificial Sequence
<220> FEATURE:
<223> OTHER INFORMATION: synthetic

<400> SEQUENCE: 292

```
Gln Ser Ile Ser Ser Tyr
1               5
```

<210> SEQ ID NO 293
<211> LENGTH: 9
<212> TYPE: DNA
<213> ORGANISM: Artificial Sequence
<220> FEATURE:
<223> OTHER INFORMATION: synthetic

<400> SEQUENCE: 293 gctgcatcc                                                            9

<210> SEQ ID NO 294
<211> LENGTH: 3
<212> TYPE: PRT
<213> ORGANISM: Artificial Sequence
<220> FEATURE:
<223> OTHER INFORMATION: synthetic

<400> SEQUENCE: 294

```
Ala Ala Ser
1
```

<210> SEQ ID NO 295
<211> LENGTH: 30
<212> TYPE: DNA
<213> ORGANISM: Artificial Sequence
<220> FEATURE:
<223> OTHER INFORMATION: synthetic

<400> SEQUENCE: 295
caacagagtt acagtacccc tccgatcacc                                    30

<210> SEQ ID NO 296
<211> LENGTH: 10
<212> TYPE: PRT
<213> ORGANISM: Artificial Sequence
<220> FEATURE:
<223> OTHER INFORMATION: synthetic

<400> SEQUENCE: 296

Gln Gln Ser Tyr Ser Thr Pro Pro Ile Thr
1               5                   10

<210> SEQ ID NO 297
<211> LENGTH: 354
<212> TYPE: DNA
<213> ORGANISM: Artificial Sequence
<220> FEATURE:
<223> OTHER INFORMATION: synthetic

<400> SEQUENCE: 297
gaggtgcagc tgttggagtc tgggggagtc ttggtacagc cggggggtc cctgagactc      60 tcctgtgcag cctctggatt cacctttagc agctttgcca tgagctgggt ccgccaggct    120
ccagggaagg gctggagtg gtctcagct attagtggta gaggtggtac tacatactac      180
gcagactccg tgatgggccg gttcaccatc tccagagaca attccaagaa cacgctgtat    240
gtgcaaatga acagcctgag agccgaggac acggccgtat attactgtgc gaaagatagg    300
gggttcgggg tctttgacta ctggggccag ggaaccctgg tcaccgtctc ctca          354

<210> SEQ ID NO 298
<211> LENGTH: 118
<212> TYPE: PRT
<213> ORGANISM: Artificial Sequence
<220> FEATURE:
<223> OTHER INFORMATION: synthetic

<400> SEQUENCE: 298

Glu Val Gln Leu Leu Glu Ser Gly Gly Val Leu Val Gln Pro Gly Gly
1               5                   10                  15

Ser Leu Arg Leu Ser Cys Ala Ala Ser Gly Phe Thr Phe Ser Ser Phe
            20                  25                  30

Ala Met Ser Trp Val Arg Gln Ala Pro Gly Lys Gly Leu Glu Trp Val
        35                  40                  45

Ser Ala Ile Ser Gly Arg Gly Gly Thr Thr Tyr Tyr Ala Asp Ser Val
    50                  55                  60

Met Gly Arg Phe Thr Ile Ser Arg Asp Asn Ser Lys Asn Thr Leu Tyr
65                  70                  75                  80

Val Gln Met Asn Ser Leu Arg Ala Glu Asp Thr Ala Val Tyr Tyr Cys
                85                  90                  95

Ala Lys Asp Arg Gly Phe Gly Val Phe Asp Tyr Trp Gly Gln Gly Thr
            100                 105                 110

Leu Val Thr Val Ser Ser
        115

<210> SEQ ID NO 299
<211> LENGTH: 24
<212> TYPE: DNA
<213> ORGANISM: Artificial Sequence
<220> FEATURE:
<223> OTHER INFORMATION: synthetic

<400> SEQUENCE: 299
ggattcacct ttagcagctt tgcc                                             24

<210> SEQ ID NO 300
<211> LENGTH: 8
<212> TYPE: PRT
<213> ORGANISM: Artificial Sequence
<220> FEATURE:
<223> OTHER INFORMATION: synthetic

<400> SEQUENCE: 300

Gly Phe Thr Phe Ser Ser Phe Ala
1               5

<210> SEQ ID NO 301
<211> LENGTH: 24
<212> TYPE: DNA
<213> ORGANISM: Artificial Sequence
<220> FEATURE:
<223> OTHER INFORMATION: synthetic

<400> SEQUENCE: 301
attagtggta gaggtggtac taca                                         24

<210> SEQ ID NO 302
<211> LENGTH: 8
<212> TYPE: PRT
<213> ORGANISM: Artificial Sequence
<220> FEATURE:
<223> OTHER INFORMATION: synthetic

<400> SEQUENCE: 302

Ile Ser Gly Arg Gly Gly Thr Thr
1               5

<210> SEQ ID NO 303
<211> LENGTH: 33
<212> TYPE: DNA
<213> ORGANISM: Artificial Sequence
<220> FEATURE:
<223> OTHER INFORMATION: synthetic

<400> SEQUENCE: 303
gcgaaagata gggggttcgg ggtctttgac tac                               33

<210> SEQ ID NO 304
<211> LENGTH: 11
<212> TYPE: PRT
<213> ORGANISM: Artificial Sequence
<220> FEATURE:
<223> OTHER INFORMATION: synthetic

<400> SEQUENCE: 304

Ala Lys Asp Arg Gly Phe Gly Val Phe Asp Tyr
1               5                   10

<210> SEQ ID NO 305
<211> LENGTH: 315
<212> TYPE: DNA
<213> ORGANISM: Artificial Sequence
<220> FEATURE:
<223> OTHER INFORMATION: synthetic

<400> SEQUENCE: 305
gacatccaga tgacccagtc tccatcctcc ctgtctgcat ctgtaggaga cagggtcacc    60
atcacttgcc aggcgagtca ggtcattaac aattatttaa attcgtatca gcagaaacca   120
gggaaagccc ctaaggtcct gatctgcgat gcatccaatg tggaaacagg gtcccgtca    180 aggttcagtg gaagtggatc tgggacagat tttactttca ccatcagcag cctgcagact   240
gaagatattg caacatatta ctgtcaacag tatgataatc tcactttcgg cggagggacc   300
aaggtggagg tcaaa                                                    315

<210> SEQ ID NO 306
<211> LENGTH: 105
<212> TYPE: PRT
<213> ORGANISM: Artificial Sequence
<220> FEATURE:
<223> OTHER INFORMATION: synthetic

<400> SEQUENCE: 306

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Val Ile Asn Asn Tyr
            20                  25                  30

Leu Asn Ser Tyr Gln Gln Lys Pro Gly Lys Ala Pro Lys Val Leu Ile
        35                  40                  45

Cys Asp Ala Ser Asn Val Glu Thr Gly Val Pro Ser Arg Phe Ser Gly
    50                  55                  60

Ser Gly Ser Gly Thr Asp Phe Thr Phe Thr Ile Ser Ser Leu Gln Thr
65                  70                  75                  80

Glu Asp Ile Ala Thr Tyr Tyr Cys Gln Gln Tyr Asp Asn Leu Thr Phe
                85                  90                  95

Gly Gly Gly Thr Lys Val Glu Val Lys
            100                 105
```

<210> SEQ ID NO 307
<211> LENGTH: 18
<212> TYPE: DNA
<213> ORGANISM: Artificial Sequence
<220> FEATURE:
<223> OTHER INFORMATION: synthetic

<400> SEQUENCE: 307
caggtcatta acaattat                                                 18

<210> SEQ ID NO 308
<211> LENGTH: 6
<212> TYPE: PRT
<213> ORGANISM: Artificial Sequence
<220> FEATURE:
<223> OTHER INFORMATION: synthetic

<400> SEQUENCE: 308

```
Gln Val Ile Asn Asn Tyr
1               5
```

<210> SEQ ID NO 309
<211> LENGTH: 9
<212> TYPE: DNA
<213> ORGANISM: Artificial Sequence
<220> FEATURE:
<223> OTHER INFORMATION: synthetic

<400> SEQUENCE: 309 gatgcatcc                                                            9

<210> SEQ ID NO 310
<211> LENGTH: 3
<212> TYPE: PRT
<213> ORGANISM: Artificial Sequence
<220> FEATURE:
<223> OTHER INFORMATION: synthetic

<400> SEQUENCE: 310

```
Asp Ala Ser
1
```

<210> SEQ ID NO 311
<211> LENGTH: 21
<212> TYPE: DNA
<213> ORGANISM: Artificial Sequence
<220> FEATURE:
<223> OTHER INFORMATION: synthetic

<400> SEQUENCE: 311
caacagtatg ataatctcac t                                           21

<210> SEQ ID NO 312
<211> LENGTH: 7
<212> TYPE: PRT
<213> ORGANISM: Artificial Sequence
<220> FEATURE:
<223> OTHER INFORMATION: synthetic

<400> SEQUENCE: 312

Gln Gln Tyr Asp Asn Leu Thr
 1               5

<210> SEQ ID NO 313
<211> LENGTH: 381
<212> TYPE: DNA
<213> ORGANISM: Artificial Sequence
<220> FEATURE:
<223> OTHER INFORMATION: synthetic

<400> SEQUENCE: 313
gaggtgcagc tgttggagtc tgggggaggc ttggaacagc ctggggggtc cctgagactc    60
tcctgtgcag cctctggatt caccttttagc agctatgcca tgatctgggt ccgccaggct   120
ccagggaagg gactggagtg gtctcaact attagtggga gtggtgttaa cacatactac    180
gcagactccg tgaagggccg gttcaccatc tccagagaca attccaagaa cacgctgcat   240
ctacaaatga acagcctgag agccgaggac acggccgttt atcactgtgc gaaagaggga   300
ttggattgtg ctaatggtgt atgctataac tactacggta tggacgtctg gggccaaggg   360
accacggtca ccgtctcctc a                                            381

<210> SEQ ID NO 314
<211> LENGTH: 127
<212> TYPE: PRT
<213> ORGANISM: Artificial Sequence
<220> FEATURE:
<223> OTHER INFORMATION: synthetic

<400> SEQUENCE: 314

Glu Val Gln Leu Leu Glu Ser Gly Gly Gly Leu Glu Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ile Trp Val Arg Gln Ala Pro Gly Lys Gly Leu Glu Trp Val
        35                  40                  45

Ser Thr Ile Ser Gly Ser Gly Val Asn Thr Tyr Tyr Ala Asp Ser Val
    50                  55                  60

Lys Gly Arg Phe Thr Ile Ser Arg Asp Asn Ser Lys Asn Thr Leu His
65                  70                  75                  80

Leu Gln Met Asn Ser Leu Arg Ala Glu Asp Thr Ala Val Tyr His Cys
                85                  90                  95

Ala Lys Glu Gly Leu Asp Cys Ala Asn Gly Val Cys Tyr Asn Tyr Tyr

```
                    100                 105                 110
Gly Met Asp Val Trp Gly Gln Gly Thr Thr Val Thr Val Ser Ser
            115                 120                 125
```

<210> SEQ ID NO 315
<211> LENGTH: 24
<212> TYPE: DNA
<213> ORGANISM: Artificial Sequence
<220> FEATURE:
<223> OTHER INFORMATION: synthetic

<400> SEQUENCE: 315
ggattcacct ttagcagcta tgcc                                          24

<210> SEQ ID NO 316
<211> LENGTH: 8
<212> TYPE: PRT
<213> ORGANISM: Artificial Sequence
<220> FEATURE:
<223> OTHER INFORMATION: synthetic

<400> SEQUENCE: 316

```
Gly Phe Thr Phe Ser Ser Tyr Ala
1               5
```

<210> SEQ ID NO 317
<211> LENGTH: 24
<212> TYPE: DNA
<213> ORGANISM: Artificial Sequence
<220> FEATURE:
<223> OTHER INFORMATION: synthetic

<400> SEQUENCE: 317
attagtggga gtggtgttaa caca                                          24

<210> SEQ ID NO 318
<211> LENGTH: 8
<212> TYPE: PRT
<213> ORGANISM: Artificial Sequence
<220> FEATURE:
<223> OTHER INFORMATION: synthetic

<400> SEQUENCE: 318

```
Ile Ser Gly Ser Gly Val Asn Thr
1               5
```

<210> SEQ ID NO 319
<211> LENGTH: 60
<212> TYPE: DNA
<213> ORGANISM: Artificial Sequence
<220> FEATURE:
<223> OTHER INFORMATION: synthetic

<400> SEQUENCE: 319
gcgaaagagg gattggattg tgctaatggt gtatgctata actactacgg tatggacgtc    60

<210> SEQ ID NO 320
<211> LENGTH: 20
<212> TYPE: PRT
<213> ORGANISM: Artificial Sequence
<220> FEATURE:
<223> OTHER INFORMATION: synthetic

<400> SEQUENCE: 320

```
Ala Lys Glu Gly Leu Asp Cys Ala Asn Gly Val Cys Tyr Asn Tyr Tyr
1               5                   10                  15
```

Gly Met Asp Val
        20

<210> SEQ ID NO 321
<211> LENGTH: 321
<212> TYPE: DNA
<213> ORGANISM: Artificial Sequence
<220> FEATURE:
<223> OTHER INFORMATION: synthetic

<400> SEQUENCE: 321
gacatccaga tgacccagtc tccatcctcc ctgtctgcat ctgtaggaga cagagtcacc      60
atcacttgcc gggcaagtca gagcattaac agcttttaa attggtatca tcagaaacca     120
gggaaagccc ctaaattcct gatctatagt gcatccaatt tgcaaagtgg ggtcccgtca     180
aggttcagtg gcagtggatc tgggacagat ttcactctca ccattagcag tctgcaacct     240
gaagattttt caacttacta ctgtcaacag agttacagta tcccgctcac tttcggcgga     300
gggaccaagg tggagatcaa a                                                321

<210> SEQ ID NO 322
<211> LENGTH: 107
<212> TYPE: PRT
<213> ORGANISM: Artificial Sequence
<220> FEATURE:
<223> OTHER INFORMATION: synthetic

<400> SEQUENCE: 322

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Ser Phe
            20                  25                  30

Leu Asn Trp Tyr His Gln Lys Pro Gly Lys Ala Pro Lys Phe Leu Ile
        35                  40                  45

Tyr Ser Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ser Thr Tyr Tyr Cys Gln Gln Ser Tyr Ser Ile Pro Leu
                85                  90                  95

Thr Phe Gly Gly Gly Thr Lys Val Glu Ile Lys
            100                 105

<210> SEQ ID NO 323
<211> LENGTH: 18
<212> TYPE: DNA
<213> ORGANISM: Artificial Sequence
<220> FEATURE:
<223> OTHER INFORMATION: synthetic

<400> SEQUENCE: 323
cagagcatta acagcttt                                                    18

<210> SEQ ID NO 324
<211> LENGTH: 6
<212> TYPE: PRT
<213> ORGANISM: Artificial Sequence
<220> FEATURE:
<223> OTHER INFORMATION: synthetic

<400> SEQUENCE: 324

Gln Ser Ile Asn Ser Phe
1               5

<210> SEQ ID NO 325
<211> LENGTH: 9
<212> TYPE: DNA
<213> ORGANISM: Artificial Sequence
<220> FEATURE:
<223> OTHER INFORMATION: synthetic

<400> SEQUENCE: 325 agtgcatcc                                                                 9

<210> SEQ ID NO 326
<211> LENGTH: 3
<212> TYPE: PRT
<213> ORGANISM: Artificial Sequence
<220> FEATURE:
<223> OTHER INFORMATION: synthetic

<400> SEQUENCE: 326

Ser Ala Ser
1

<210> SEQ ID NO 327
<211> LENGTH: 27
<212> TYPE: DNA
<213> ORGANISM: Artificial Sequence
<220> FEATURE:
<223> OTHER INFORMATION: synthetic

<400> SEQUENCE: 327
caacagagtt acagtatccc gctcact                                             27

<210> SEQ ID NO 328
<211> LENGTH: 9
<212> TYPE: PRT
<213> ORGANISM: Artificial Sequence
<220> FEATURE:
<223> OTHER INFORMATION: synthetic

<400> SEQUENCE: 328

Gln Gln Ser Tyr Ser Ile Pro Leu Thr
1               5

<210> SEQ ID NO 329
<211> LENGTH: 378
<212> TYPE: DNA
<213> ORGANISM: Artificial Sequence
<220> FEATURE:
<223> OTHER INFORMATION: synthetic

<400> SEQUENCE: 329
gaggtgcagc tggtggagtc tgggggagcc ttggtacagc ctggagggtc cctgagactc      60
tcctgtgcag cctctggatt catcttcggt agttatgaga tgaactgggt ccgccaggct     120
ccagggaagg ggctggagtg gctttcatac attagtagta gtggtagtac catatactac     180
gcagactctg tgaagggccg attcaccatc tccagacaca cgccaagaa ctcactgtat      240 ctgcaaatga acagcctgag agccgaggac acggctgttt attactgtgc gagagaacgg     300
gggcagctcg gccggggagg gtattactac tacggtatgg acgtctgggg ccaagggacc     360
acggtcaccg tctcctca                                                    378

<210> SEQ ID NO 330

```
<211> LENGTH: 126
<212> TYPE: PRT
<213> ORGANISM: Artificial Sequence
<220> FEATURE:
<223> OTHER INFORMATION: synthetic

<400> SEQUENCE: 330
```

Glu Val Gln Leu Val Glu Ser Gly Gly Ala Leu Val Gln Pro Gly Gly
1               5                   10                  15

Ser Leu Arg Leu Ser Cys Ala Ala Ser Gly Phe Ile Phe Gly Ser Tyr
            20                  25                  30

Glu Met Asn Trp Val Arg Gln Ala Pro Gly Lys Gly Leu Glu Trp Leu
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Gly Gln Leu Gly Arg Gly Tyr Tyr Tyr Tyr Gly
            100                 105                 110

Met Asp Val Trp Gly Gln Gly Thr Thr Val Thr Val Ser Ser
        115                 120                 125

```
<210> SEQ ID NO 331
<211> LENGTH: 24
<212> TYPE: DNA
<213> ORGANISM: Artificial Sequence
<220> FEATURE:
<223> OTHER INFORMATION: synthetic

<400> SEQUENCE: 331
ggattcatct tcggtagtta tgag                                    24

<210> SEQ ID NO 332
<211> LENGTH: 8
<212> TYPE: PRT
<213> ORGANISM: Artificial Sequence
<220> FEATURE:
<223> OTHER INFORMATION: synthetic

<400> SEQUENCE: 332
```

Gly Phe Ile Phe Gly Ser Tyr Glu
1               5

```
<210> SEQ ID NO 333
<211> LENGTH: 24
<212> TYPE: DNA
<213> ORGANISM: Artificial Sequence
<220> FEATURE:
<223> OTHER INFORMATION: synthetic

<400> SEQUENCE: 333
attagtagta gtggtagtac cata                                    24

<210> SEQ ID NO 334
<211> LENGTH: 8
<212> TYPE: PRT
<213> ORGANISM: Artificial Sequence
<220> FEATURE:
<223> OTHER INFORMATION: synthetic

<400> SEQUENCE: 334
```

Ile Ser Ser Ser Gly Ser Thr Ile
1               5

<210> SEQ ID NO 335
<211> LENGTH: 57
<212> TYPE: DNA
<213> ORGANISM: Artificial Sequence
<220> FEATURE:
<223> OTHER INFORMATION: synthetic

<400> SEQUENCE: 335
gcgagagaac gggggcagct cggccgggga gggtattact actacggtat ggacgtc     57

<210> SEQ ID NO 336
<211> LENGTH: 19
<212> TYPE: PRT
<213> ORGANISM: Artificial Sequence
<220> FEATURE:
<223> OTHER INFORMATION: synthetic

<400> SEQUENCE: 336

Ala Arg Glu Arg Gly Gln Leu Gly Arg Gly Gly Tyr Tyr Tyr Tyr Gly
1               5                   10                  15

Met Asp Val

<210> SEQ ID NO 337
<211> LENGTH: 327
<212> TYPE: DNA
<213> ORGANISM: Artificial Sequence
<220> FEATURE:
<223> OTHER INFORMATION: synthetic

<400> SEQUENCE: 337
gaaattgtgt tgacgcggtc tccaggcacc ctgtctttgt ctccagggga aagagccacc     60
ctctcctgca gggccagtca gagtgttagc agcagctact tagcctggta ccatcagaaa    120
cctggccagg ctcccaggct cctcatgtat ggtacatcca tcagggccac tggcatccca    180
gacaggttca gtggcagtgg gtctgggaca gacttcactc tcaccatcag cagactggag    240
cctgaagatt ttgcagtgta ttactgtcag cagtatggta gctcacctcc gtggacgttc    300
ggccaaggga ccaaggtgga aatcaaa                                       327

<210> SEQ ID NO 338
<211> LENGTH: 109
<212> TYPE: PRT
<213> ORGANISM: Artificial Sequence
<220> FEATURE:
<223> OTHER INFORMATION: synthetic

<400> SEQUENCE: 338

Glu Ile Val Leu Thr Arg Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr His Gln Lys Pro Gly Gln Ala Pro Arg Leu Leu
            35                  40                  45

Met Tyr Gly Thr Ser Ile Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Pro Trp Thr Phe Gly Gln Gly Thr Lys Val Glu Ile Lys
            100                 105

<210> SEQ ID NO 339
<211> LENGTH: 21
<212> TYPE: DNA
<213> ORGANISM: Artificial Sequence
<220> FEATURE:
<223> OTHER INFORMATION: synthetic

<400> SEQUENCE: 339
cagagtgtta gcagcagcta c                                             21

<210> SEQ ID NO 340
<211> LENGTH: 7
<212> TYPE: PRT
<213> ORGANISM: Artificial Sequence
<220> FEATURE:
<223> OTHER INFORMATION: synthetic

<400> SEQUENCE: 340

Gln Ser Val Ser Ser Ser Tyr
1               5

<210> SEQ ID NO 341
<211> LENGTH: 9
<212> TYPE: DNA
<213> ORGANISM: Artificial Sequence
<220> FEATURE:
<223> OTHER INFORMATION: synthetic

<400> SEQUENCE: 341 ggtacatcc                                                            9

<210> SEQ ID NO 342
<211> LENGTH: 3
<212> TYPE: PRT
<213> ORGANISM: Artificial Sequence
<220> FEATURE:
<223> OTHER INFORMATION: synthetic

<400> SEQUENCE: 342

Gly Thr Ser
1

<210> SEQ ID NO 343
<211> LENGTH: 30
<212> TYPE: DNA
<213> ORGANISM: Artificial Sequence
<220> FEATURE:
<223> OTHER INFORMATION: synthetic

<400> SEQUENCE: 343
cagcagtatg gtagctcacc tccgtggacg                                    30

<210> SEQ ID NO 344
<211> LENGTH: 10
<212> TYPE: PRT
<213> ORGANISM: Artificial Sequence
<220> FEATURE:
<223> OTHER INFORMATION: synthetic

<400> SEQUENCE: 344

Gln Gln Tyr Gly Ser Ser Pro Pro Trp Thr
1               5                   10

<210> SEQ ID NO 345
<211> LENGTH: 384
<212> TYPE: DNA
<213> ORGANISM: Artificial Sequence
<220> FEATURE:
<223> OTHER INFORMATION: synthetic

<400> SEQUENCE: 345

```
caggtccggc tggtgcagtc tggggctgag gtgaagaagc ctgggtcctc ggtgaaggtc    60
tcctgcaagg cttctggaga caccttcagc agctatgcta tcagctgggt gcgacaggcc   120
cctggacaag gcttgagtg gatgggaggg atcatccctt tctttgttac aactacctac   180
gcacagaatt tccagggcag agtcacgatt accacggacg aatccacgcg cacagcctac   240
atggagctga gcagtctgag atctgaggac tcggccgtgt attactgtgc gagagatcgg   300
ccgtgtatca gctcggctgg tacacgctac cactactgcg ttatggacgt ctggggccaa   360
gggacaacgg tcaccgtctc ctca                                          384
```

<210> SEQ ID NO 346
<211> LENGTH: 128
<212> TYPE: PRT
<213> ORGANISM: Artificial Sequence
<220> FEATURE:
<223> OTHER INFORMATION: synthetic

<400> SEQUENCE: 346

```
Gln Val Arg Leu Val Gln Ser Gly Ala Glu Val Lys Lys Pro Gly Ser
1               5                   10                  15
Ser Val Lys Val Ser Cys Lys Ala Ser Gly Asp Thr Phe Ser Ser Tyr
            20                  25                  30
Ala Ile Ser Trp Val Arg Gln Ala Pro Gly Gln Gly Leu Glu Trp Met
        35                  40                  45
Gly Gly Ile Ile Pro Phe Phe Val Thr Thr Thr Tyr Ala Gln Asn Phe
    50                  55                  60
Gln Gly Arg Val Thr Ile Thr Thr Asp Glu Ser Thr Arg Thr Ala Tyr
65                  70                  75                  80
Met Glu Leu Ser Ser Leu Arg Ser Glu Asp Ser Ala Val Tyr Tyr Cys
                85                  90                  95
Ala Arg Asp Arg Pro Cys Ile Ser Ser Ala Gly Thr Arg Tyr His Tyr
            100                 105                 110
Cys Val Met Asp Val Trp Gly Gln Gly Thr Thr Val Thr Val Ser Ser
        115                 120                 125
```

<210> SEQ ID NO 347
<211> LENGTH: 24
<212> TYPE: DNA
<213> ORGANISM: Artificial Sequence
<220> FEATURE:
<223> OTHER INFORMATION: synthetic

<400> SEQUENCE: 347

```
ggagacacct tcagcagcta tgct                                           24
```

<210> SEQ ID NO 348
<211> LENGTH: 8
<212> TYPE: PRT
<213> ORGANISM: Artificial Sequence
<220> FEATURE:
<223> OTHER INFORMATION: synthetic

<400> SEQUENCE: 348

Gly Asp Thr Phe Ser Ser Tyr Ala
1               5

<210> SEQ ID NO 349
<211> LENGTH: 24
<212> TYPE: DNA
<213> ORGANISM: Artificial Sequence
<220> FEATURE:
<223> OTHER INFORMATION: synthetic

<400> SEQUENCE: 349
atcatccctt tctttgttac aact                                      24

<210> SEQ ID NO 350
<211> LENGTH: 8
<212> TYPE: PRT
<213> ORGANISM: Artificial Sequence
<220> FEATURE:
<223> OTHER INFORMATION: synthetic

<400> SEQUENCE: 350

Ile Ile Pro Phe Phe Val Thr Thr
1               5

<210> SEQ ID NO 351
<211> LENGTH: 63
<212> TYPE: DNA
<213> ORGANISM: Artificial Sequence
<220> FEATURE:
<223> OTHER INFORMATION: synthetic

<400> SEQUENCE: 351
gcgagagatc ggccgtgtat cagctcggct ggtacacgct accactactg cgttatggac   60
gtc                                                                63

<210> SEQ ID NO 352
<211> LENGTH: 21
<212> TYPE: PRT
<213> ORGANISM: Artificial Sequence
<220> FEATURE:
<223> OTHER INFORMATION: synthetic

<400> SEQUENCE: 352

Ala Arg Asp Arg Pro Cys Ile Ser Ser Ala Gly Thr Arg Tyr His Tyr
1               5                   10                  15

Cys Val Met Asp Val
            20

<210> SEQ ID NO 353
<211> LENGTH: 324
<212> TYPE: DNA
<213> ORGANISM: Artificial Sequence
<220> FEATURE:
<223> OTHER INFORMATION: synthetic

<400> SEQUENCE: 353
gacatccaga tgacccagtc tccatcctcc ctgtctgcat ctgtaggaga cagagtcacc   60
atcacttgcc gggcaagtca gagcattagc agttatttaa attggtatca gcagaaacca  120
gggaaagccc ctaagctcct gatctatgct gcatccagtt tgcaaagtgg ggtcccatca  180
aggttcagtg gcagtggatc tgggacagat ttcactctca ccatcagcag tctgcaacct  240
gaagattttg caacttacta ctgtcaacag agttacagta cccctccgat caccttcggc  300
caagggacac gactggagat taaa                                                     324

<210> SEQ ID NO 354
<211> LENGTH: 108
<212> TYPE: PRT
<213> ORGANISM: Artificial Sequence
<220> FEATURE:
<223> OTHER INFORMATION: synthetic

<400> SEQUENCE: 354

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 355
<211> LENGTH: 18
<212> TYPE: DNA
<213> ORGANISM: Artificial Sequence
<220> FEATURE:
<223> OTHER INFORMATION: synthetic

<400> SEQUENCE: 355
cagagcatta gcagttat                                                            18

<210> SEQ ID NO 356
<211> LENGTH: 6
<212> TYPE: PRT
<213> ORGANISM: Artificial Sequence
<220> FEATURE:
<223> OTHER INFORMATION: synthetic

<400> SEQUENCE: 356

Gln Ser Ile Ser Ser Tyr
1               5

<210> SEQ ID NO 357
<211> LENGTH: 9
<212> TYPE: DNA
<213> ORGANISM: Artificial Sequence
<220> FEATURE:
<223> OTHER INFORMATION: synthetic

<400> SEQUENCE: 357 gctgcatcc                                                                      9

<210> SEQ ID NO 358
<211> LENGTH: 3
<212> TYPE: PRT
<213> ORGANISM: Artificial Sequence
<220> FEATURE:
<223> OTHER INFORMATION: synthetic

<400> SEQUENCE: 358

Ala Ala Ser
1

<210> SEQ ID NO 359
<211> LENGTH: 30
<212> TYPE: DNA
<213> ORGANISM: Artificial Sequence
<220> FEATURE:
<223> OTHER INFORMATION: synthetic

<400> SEQUENCE: 359
caacagagtt acagtacccc tccgatcacc                                      30

<210> SEQ ID NO 360
<211> LENGTH: 10
<212> TYPE: PRT
<213> ORGANISM: Artificial Sequence
<220> FEATURE:
<223> OTHER INFORMATION: synthetic

<400> SEQUENCE: 360

Gln Gln Ser Tyr Ser Thr Pro Pro Ile Thr
1               5                   10

<210> SEQ ID NO 361
<211> LENGTH: 357
<212> TYPE: DNA
<213> ORGANISM: Artificial Sequence
<220> FEATURE:
<223> OTHER INFORMATION: synthetic

<400> SEQUENCE: 361
caggttcaac tggtgcagtc tggagctgag gtgaagaagc ctggggcctc agtgaaggtc     60
tcctgcaagg cttctggtta ccctttacc agccatggta tcagctgggt gcgacaggcc    120
cctggacagg ggtttgagtg gatgggatgg atcggcactt acaatagtaa cacagactat    180
gcacagaact tccagggcag agtcaccatg accacagaca catccacgag cacggcctac    240
atggagctga ggaacctgag atctgacgac acggccgtat attattgtgc gagagaaagg    300
ggtccctatt acggtatgga cgtctggggc caagggacca cggtcaccgt ctcctca      357

<210> SEQ ID NO 362
<211> LENGTH: 119
<212> TYPE: PRT
<213> ORGANISM: Artificial Sequence
<220> FEATURE:
<223> OTHER INFORMATION: synthetic

<400> SEQUENCE: 362

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
                20                  25                  30

Gly Ile Ser Trp Val Arg Gln Ala Pro Gly Gln Gly Phe Glu Trp Met
            35                  40                  45

Gly Trp Ile Gly Thr Tyr Asn Ser Asn Thr Asp Tyr Ala Gln Asn Phe
        50                  55                  60

Gln Gly Arg Val Thr Met Thr Thr Asp Thr Ser Thr Ser Thr Ala Tyr
65                  70                  75                  80

Met Glu Leu Arg Asn Leu Arg Ser Asp Asp Thr Ala Val Tyr Tyr Cys
                85                  90                  95

Ala Arg Glu Arg Gly Pro Tyr Tyr Gly Met Asp Val Trp Gly Gln Gly
            100                 105                 110

Thr Thr Val Thr Val Ser Ser
        115

<210> SEQ ID NO 363
<211> LENGTH: 24
<212> TYPE: DNA
<213> ORGANISM: Artificial Sequence
<220> FEATURE:
<223> OTHER INFORMATION: synthetic

<400> SEQUENCE: 363
ggttacacct ttaccagcca tggt                                          24

<210> SEQ ID NO 364
<211> LENGTH: 8
<212> TYPE: PRT
<213> ORGANISM: Artificial Sequence
<220> FEATURE:
<223> OTHER INFORMATION: synthetic

<400> SEQUENCE: 364

Gly Tyr Thr Phe Thr Ser His Gly
1               5

<210> SEQ ID NO 365
<211> LENGTH: 24
<212> TYPE: DNA
<213> ORGANISM: Artificial Sequence
<220> FEATURE:
<223> OTHER INFORMATION: synthetic

<400> SEQUENCE: 365
atcggcactt acaatagtaa caca                                          24

<210> SEQ ID NO 366
<211> LENGTH: 8
<212> TYPE: PRT
<213> ORGANISM: Artificial Sequence
<220> FEATURE:
<223> OTHER INFORMATION: synthetic

<400> SEQUENCE: 366

Ile Gly Thr Tyr Asn Ser Asn Thr
1               5

<210> SEQ ID NO 367
<211> LENGTH: 36
<212> TYPE: DNA
<213> ORGANISM: Artificial Sequence
<220> FEATURE:
<223> OTHER INFORMATION: synthetic

<400> SEQUENCE: 367
gcgagagaaa ggggtcccta ttacggtatg gacgtc                             36

<210> SEQ ID NO 368
<211> LENGTH: 12
<212> TYPE: PRT
<213> ORGANISM: Artificial Sequence
<220> FEATURE:
<223> OTHER INFORMATION: synthetic

<400> SEQUENCE: 368

Ala Arg Glu Arg Gly Pro Tyr Tyr Gly Met Asp Val

<210> SEQ ID NO 369
<211> LENGTH: 321
<212> TYPE: DNA
<213> ORGANISM: Artificial Sequence
<220> FEATURE:
<223> OTHER INFORMATION: synthetic

<400> SEQUENCE: 369

```
gaaattgtgt tggcgcagtc tccaggcacc ctgtctttgt ctccagggga aagagccacc    60
ctctcctgca gggccagtca gagtgttaac agcaactact tagcctggta tcagcagaaa   120
cctggccagg ctcccaggct cctcatctat ggtgcatcca gtagggccac tggcatccca   180
gacaggttca gtggcagtgg gtctgggaca gacttcactc tcaccatcag cagactggag   240
cctgaagatt ttgcagtgta ttactgtcaa cagtatggta actcactcac tttcggccct   300
gggaccaaag tggatttcaa a                                             321
```

<210> SEQ ID NO 370
<211> LENGTH: 107
<212> TYPE: PRT
<213> ORGANISM: Artificial Sequence
<220> FEATURE:
<223> OTHER INFORMATION: synthetic

<400> SEQUENCE: 370

Glu Ile Val Leu Ala Gln Ser Pro Gly Thr Leu Ser Leu Ser Pro Gly
1               5                   10                  15
Glu Arg Ala Thr Leu Ser Cys Arg Ala Ser Gln Ser Val Asn Ser Asn
            20                  25                  30
Tyr Leu Ala Trp Tyr Gln Gln Lys Pro Gly Gln Ala Pro Arg Leu Leu
        35                  40                  45
Ile Tyr Gly Ala Ser Ser Arg Ala Thr Gly Ile Pro Asp Arg Phe Ser
    50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Tyr Gly Asn Ser Leu
                85                  90                  95
Thr Phe Gly Pro Gly Thr Lys Val Asp Phe Lys
            100                 105

<210> SEQ ID NO 371
<211> LENGTH: 21
<212> TYPE: DNA
<213> ORGANISM: Artificial Sequence
<220> FEATURE:
<223> OTHER INFORMATION: synthetic

<400> SEQUENCE: 371

```
cagagtgtta acagcaacta c                                              21
```

<210> SEQ ID NO 372
<211> LENGTH: 7
<212> TYPE: PRT
<213> ORGANISM: Artificial Sequence
<220> FEATURE:
<223> OTHER INFORMATION: synthetic

<400> SEQUENCE: 372

Gln Ser Val Asn Ser Asn Tyr
1               5

<210> SEQ ID NO 373
<211> LENGTH: 9
<212> TYPE: DNA
<213> ORGANISM: Artificial Sequence
<220> FEATURE:
<223> OTHER INFORMATION: synthetic

<400> SEQUENCE: 373 ggtgcatcc                                                                 9

<210> SEQ ID NO 374
<211> LENGTH: 3
<212> TYPE: PRT
<213> ORGANISM: Artificial Sequence
<220> FEATURE:
<223> OTHER INFORMATION: synthetic

<400> SEQUENCE: 374

Gly Ala Ser
1

<210> SEQ ID NO 375
<211> LENGTH: 24
<212> TYPE: DNA
<213> ORGANISM: Artificial Sequence
<220> FEATURE:
<223> OTHER INFORMATION: synthetic

<400> SEQUENCE: 375
caacagtatg gtaactcact cact                                               24

<210> SEQ ID NO 376
<211> LENGTH: 8
<212> TYPE: PRT
<213> ORGANISM: Artificial Sequence
<220> FEATURE:
<223> OTHER INFORMATION: synthetic

<400> SEQUENCE: 376

Gln Gln Tyr Gly Asn Ser Leu Thr
1               5

<210> SEQ ID NO 377
<211> LENGTH: 354
<212> TYPE: DNA
<213> ORGANISM: Artificial Sequence
<220> FEATURE:
<223> OTHER INFORMATION: synthetic

<400> SEQUENCE: 377
gaggtgcagc tgtttggagtc tgggggaggc ttggtacaga ctggggggtc cctgagactc        60
tcctgtgcag cctctggatt cacctttagc aattatgcca tgagctgggt ccgccaggct       120
ccagggaagg ggctggagtg gtctcagct attagtgata gaggtggtag tatatactac        180
gcagactccg tgaagggccg gttcaccatc tccagagaca attccaagaa cacgaagtat       240
ctgcaaatgg acagcctgag agccgaggac acggccgtat attactgtgc gcaagatagg       300
gggttcgggg tctttgacta ctggggccag ggaaccctgg tcaccgtctc ctca             354

<210> SEQ ID NO 378
<211> LENGTH: 118
<212> TYPE: PRT
<213> ORGANISM: Artificial Sequence
<220> FEATURE:

<223> OTHER INFORMATION: synthetic

<400> SEQUENCE: 378

```
Glu Val Gln Leu Leu Glu Ser Gly Gly Gly Leu Val Gln Thr Gly
1               5                   10                  15
Ser Leu Arg Leu Ser Cys Ala Ala Ser Gly Phe Thr Phe Ser Asn Tyr
            20                  25                  30
Ala Met Ser Trp Val Arg Gln Ala Pro Gly Lys Gly Leu Glu Trp Val
        35                  40                  45
Ser Ala Ile Ser Asp Arg Gly Gly Ser Ile Tyr Tyr Ala Asp Ser Val
    50                  55                  60
Lys Gly Arg Phe Thr Ile Ser Arg Asp Asn Ser Lys Asn Thr Lys Tyr
65                  70                  75                  80
Leu Gln Met Asp Ser Leu Arg Ala Glu Asp Thr Ala Val Tyr Tyr Cys
                85                  90                  95
Ala Gln Asp Arg Gly Phe Gly Val Phe Asp Tyr Trp Gly Gln Gly Thr
            100                 105                 110
Leu Val Thr Val Ser Ser
        115
```

<210> SEQ ID NO 379
<211> LENGTH: 24
<212> TYPE: DNA
<213> ORGANISM: Artificial Sequence
<220> FEATURE:
<223> OTHER INFORMATION: synthetic

<400> SEQUENCE: 379
ggattcacct ttagcaatta tgcc          24

<210> SEQ ID NO 380
<211> LENGTH: 8
<212> TYPE: PRT
<213> ORGANISM: Artificial Sequence
<220> FEATURE:
<223> OTHER INFORMATION: synthetic

<400> SEQUENCE: 380

```
Gly Phe Thr Phe Ser Asn Tyr Ala
1               5
```

<210> SEQ ID NO 381
<211> LENGTH: 24
<212> TYPE: DNA
<213> ORGANISM: Artificial Sequence
<220> FEATURE:
<223> OTHER INFORMATION: synthetic

<400> SEQUENCE: 381
attagtgata gaggtggtag tata          24

<210> SEQ ID NO 382
<211> LENGTH: 8
<212> TYPE: PRT
<213> ORGANISM: Artificial Sequence
<220> FEATURE:
<223> OTHER INFORMATION: synthetic

<400> SEQUENCE: 382

```
Ile Ser Asp Arg Gly Gly Ser Ile
1               5
```

<210> SEQ ID NO 383
<211> LENGTH: 33
<212> TYPE: DNA
<213> ORGANISM: Artificial Sequence
<220> FEATURE:
<223> OTHER INFORMATION: synthetic

<400> SEQUENCE: 383
gcgcaagata gggggttcgg ggtctttgac tac                          33

<210> SEQ ID NO 384
<211> LENGTH: 11
<212> TYPE: PRT
<213> ORGANISM: Artificial Sequence
<220> FEATURE:
<223> OTHER INFORMATION: synthetic

<400> SEQUENCE: 384

Ala Gln Asp Arg Gly Phe Gly Val Phe Asp Tyr
1               5                   10

<210> SEQ ID NO 385
<211> LENGTH: 321
<212> TYPE: DNA
<213> ORGANISM: Artificial Sequence
<220> FEATURE:
<223> OTHER INFORMATION: synthetic

<400> SEQUENCE: 385
gacatccaga tgacccagtc tccatcctcc ctgtctgcat ctgtaggaga cagagtcacc    60
atcacttgcc aggcgagtca ggacattggc aactatttaa attggtttca gcagagacca   120
gggaaagccc ctaatctcct gatctacggt gcatccaatt tggaaacagg ggtcccatca   180
aggttcagtg gaggtggatc tgggacagat tttactttca ccatcagcag cctgcagcct   240
gaagatattg caacatattt ctgtcaacag tatgataatc tcccttttac tttcggccct   300
gggaccaaag tggaaatcaa a                                             321

<210> SEQ ID NO 386
<211> LENGTH: 107
<212> TYPE: PRT
<213> ORGANISM: Artificial Sequence
<220> FEATURE:
<223> OTHER INFORMATION: synthetic

<400> SEQUENCE: 386

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Gly Asn Tyr
            20                  25                  30

Leu Asn Trp Phe Gln Gln Arg Pro Gly Lys Ala Pro Asn Leu Leu Ile
        35                  40                  45

Tyr Gly Ala Ser Asn Leu Glu Thr Gly Val Pro Ser Arg Phe Ser Gly
    50                  55                  60

Gly Gly Ser Gly Thr Asp Phe Thr Phe Thr Ile Ser Ser Leu Gln Pro
65                  70                  75                  80

Glu Asp Ile Ala Thr Tyr Phe Cys Gln Gln Tyr Asp Asn Leu Pro Phe
                85                  90                  95

Thr Phe Gly Pro Gly Thr Lys Val Glu Ile Lys
            100                 105

<210> SEQ ID NO 387

```
<211> LENGTH: 18
<212> TYPE: DNA
<213> ORGANISM: Artificial Sequence
<220> FEATURE:
<223> OTHER INFORMATION: synthetic

<400> SEQUENCE: 387
caggacattg gcaactat                                                       18

<210> SEQ ID NO 388
<211> LENGTH: 6
<212> TYPE: PRT
<213> ORGANISM: Artificial Sequence
<220> FEATURE:
<223> OTHER INFORMATION: synthetic

<400> SEQUENCE: 388

Gln Asp Ile Gly Asn Tyr
1               5

<210> SEQ ID NO 389
<211> LENGTH: 9
<212> TYPE: DNA
<213> ORGANISM: Artificial Sequence
<220> FEATURE:
<223> OTHER INFORMATION: synthetic

<400> SEQUENCE: 389 ggtgcatcc                                                                  9

<210> SEQ ID NO 390
<211> LENGTH: 3
<212> TYPE: PRT
<213> ORGANISM: Artificial Sequence
<220> FEATURE:
<223> OTHER INFORMATION: synthetic

<400> SEQUENCE: 390

Gly Ala Ser
1

<210> SEQ ID NO 391
<211> LENGTH: 27
<212> TYPE: DNA
<213> ORGANISM: Artificial Sequence
<220> FEATURE:
<223> OTHER INFORMATION: synthetic

<400> SEQUENCE: 391
caacagtatg ataatctccc tttcact                                             27

<210> SEQ ID NO 392
<211> LENGTH: 9
<212> TYPE: PRT
<213> ORGANISM: Artificial Sequence
<220> FEATURE:
<223> OTHER INFORMATION: synthetic

<400> SEQUENCE: 392

Gln Gln Tyr Asp Asn Leu Pro Phe Thr
1               5

<210> SEQ ID NO 393
<211> LENGTH: 384
<212> TYPE: DNA
<213> ORGANISM: Artificial Sequence
<220> FEATURE:
```

<223> OTHER INFORMATION: synthetic

<400> SEQUENCE: 393

```
caggtccagc tggtgcagtc tggggctgag gtgaagaagc ctgggtcctc ggtgaaggtc    60
tcctgcaagg cttctaaaga caccttcagc agctatgcta tcagctgggt gcgacaggcc   120
cctggacaag ggcttgagtg gatgggaggg atcatccctt tctttggtac aactacctac   180
gaacagaagt tccagggcag agtcacgatt accacgacg aatccacgcg cacagcctac    240
atggagctga gcagcctgag atctgaggac tcggccgtgt attactgtgc gagagatcgg   300
ccgtgtatca gctcggctgg tacacgctac cactactgcg ttatggacgt ctggggccaa   360
gggacaacgg tcaccgtctc ctca                                          384
```

<210> SEQ ID NO 394
<211> LENGTH: 128
<212> TYPE: PRT
<213> ORGANISM: Artificial Sequence
<220> FEATURE:
<223> OTHER INFORMATION: synthetic

<400> SEQUENCE: 394

```
Gln Val Gln Leu Val Gln Ser Gly Ala Glu Val Lys Lys Pro Gly Ser
1               5                   10                  15
Ser Val Lys Val Ser Cys Lys Ala Ser Lys Asp Thr Phe Ser Ser Tyr
            20                  25                  30
Ala Ile Ser Trp Val Arg Gln Ala Pro Gly Gln Gly Leu Glu Trp Met
        35                  40                  45
Gly Gly Ile Ile Pro Phe Phe Gly Thr Thr Thr Tyr Glu Gln Lys Phe
    50                  55                  60
Gln Gly Arg Val Thr Ile Thr Thr Asp Glu Ser Thr Arg Thr Ala Tyr
65                  70                  75                  80
Met Glu Leu Ser Ser Leu Arg Ser Glu Asp Ser Ala Val Tyr Tyr Cys
                85                  90                  95
Ala Arg Asp Arg Pro Cys Ile Ser Ser Ala Gly Thr Arg Tyr His Tyr
            100                 105                 110
Cys Val Met Asp Val Trp Gly Gln Gly Thr Thr Val Thr Val Ser Ser
        115                 120                 125
```

<210> SEQ ID NO 395
<211> LENGTH: 24
<212> TYPE: DNA
<213> ORGANISM: Artificial Sequence
<220> FEATURE:
<223> OTHER INFORMATION: synthetic

<400> SEQUENCE: 395

```
aaagacacct tcagcagcta tgct                                          24
```

<210> SEQ ID NO 396
<211> LENGTH: 8
<212> TYPE: PRT
<213> ORGANISM: Artificial Sequence
<220> FEATURE:
<223> OTHER INFORMATION: synthetic

<400> SEQUENCE: 396

```
Lys Asp Thr Phe Ser Ser Tyr Ala
1               5
```

<210> SEQ ID NO 397

<211> LENGTH: 24
<212> TYPE: DNA
<213> ORGANISM: Artificial Sequence
<220> FEATURE:
<223> OTHER INFORMATION: synthetic

<400> SEQUENCE: 397
atcatccctt tctttggtac aact                                          24

<210> SEQ ID NO 398
<211> LENGTH: 8
<212> TYPE: PRT
<213> ORGANISM: Artificial Sequence
<220> FEATURE:
<223> OTHER INFORMATION: synthetic

<400> SEQUENCE: 398

Ile Ile Pro Phe Phe Gly Thr Thr
1               5

<210> SEQ ID NO 399
<211> LENGTH: 63
<212> TYPE: DNA
<213> ORGANISM: Artificial Sequence
<220> FEATURE:
<223> OTHER INFORMATION: synthetic

<400> SEQUENCE: 399
gcgagagatc ggccgtgtat cagctcggct ggtacacgct accactactg cgttatggac    60
gtc                                                                 63

<210> SEQ ID NO 400
<211> LENGTH: 21
<212> TYPE: PRT
<213> ORGANISM: Artificial Sequence
<220> FEATURE:
<223> OTHER INFORMATION: synthetic

<400> SEQUENCE: 400

Ala Arg Asp Arg Pro Cys Ile Ser Ser Ala Gly Thr Arg Tyr His Tyr
1               5                   10                  15

Cys Val Met Asp Val
            20

<210> SEQ ID NO 401
<211> LENGTH: 324
<212> TYPE: DNA
<213> ORGANISM: Artificial Sequence
<220> FEATURE:
<223> OTHER INFORMATION: synthetic

<400> SEQUENCE: 401
gacatccaga tgacccagtc tccatcctcc ctgtctgcat ctgtaggaga cagagtcacc    60
atcacttgcc gggcaagtca gagtattagc agttatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacagta cccctccgat caccttcggc   300
caagggacac gactggagat taaa                                         324

<210> SEQ ID NO 402
<211> LENGTH: 108
<212> TYPE: PRT

<213> ORGANISM: Artificial Sequence
<220> FEATURE:
<223> OTHER INFORMATION: synthetic

<400> SEQUENCE: 402

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Ser Ser Tyr
            20                  25                  30
Leu Asn Trp Tyr Gln Gln Lys Pro Gly Lys Ala Pro Lys Leu Leu Ile
        35                  40                  45
Tyr Ala Ala Ser Ser Leu Gln Ser Gly Val Pro Ser Arg Phe Ser Gly
50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ser Tyr Ser Thr Pro Pro
                85                  90                  95
Ile Thr Phe Gly Gln Gly Thr Arg Leu Glu Ile Lys
            100                 105

<210> SEQ ID NO 403
<211> LENGTH: 18
<212> TYPE: DNA
<213> ORGANISM: Artificial Sequence
<220> FEATURE:
<223> OTHER INFORMATION: synthetic

<400> SEQUENCE: 403
cagagtatta gcagttat                                            18

<210> SEQ ID NO 404
<211> LENGTH: 6
<212> TYPE: PRT
<213> ORGANISM: Artificial Sequence
<220> FEATURE:
<223> OTHER INFORMATION: synthetic

<400> SEQUENCE: 404

Gln Ser Ile Ser Ser Tyr
1               5

<210> SEQ ID NO 405
<211> LENGTH: 9
<212> TYPE: DNA
<213> ORGANISM: Artificial Sequence
<220> FEATURE:
<223> OTHER INFORMATION: synthetic

<400> SEQUENCE: 405 gctgcatcc                                                       9

<210> SEQ ID NO 406
<211> LENGTH: 3
<212> TYPE: PRT
<213> ORGANISM: Artificial Sequence
<220> FEATURE:
<223> OTHER INFORMATION: synthetic

<400> SEQUENCE: 406

Ala Ala Ser
1

<210> SEQ ID NO 407

<210> SEQ ID NO 407
<211> LENGTH: 30
<212> TYPE: DNA
<213> ORGANISM: Artificial Sequence
<220> FEATURE:
<223> OTHER INFORMATION: synthetic

<400> SEQUENCE: 407
caacagagtt acagtacccc tccgatcacc                                          30

<210> SEQ ID NO 408
<211> LENGTH: 10
<212> TYPE: PRT
<213> ORGANISM: Artificial Sequence
<220> FEATURE:
<223> OTHER INFORMATION: synthetic

<400> SEQUENCE: 408

Gln Gln Ser Tyr Ser Thr Pro Pro Ile Thr
1               5                   10

<210> SEQ ID NO 409
<211> LENGTH: 357
<212> TYPE: DNA
<213> ORGANISM: Artificial Sequence
<220> FEATURE:
<223> OTHER INFORMATION: synthetic

<400> SEQUENCE: 409
cagctgcagc tgcaggagtc gggcccagga ctggtgaagc cttcggagac cctgtccctc          60
acctgcactg tctctggtgg ctccatcagc agtggtaatt actactgggg ctggatccgc         120 cagcccccg  ggaaggggct ggagtggttt gggactatct attatagtgg gagcacctac         180
tacaacccgt ccctcaagag tcgagtcacc atatccgtag acacgtccaa gaaccagttc         240
tccctgaagc tgagctctgt gaccgccgca gacacggctg tgtattactg tgcgagacgg         300
gcagcagttg gtcactttga ctactggggc cagggaaccc tggtcaccgt ctcctca           357

<210> SEQ ID NO 410
<211> LENGTH: 119
<212> TYPE: PRT
<213> ORGANISM: Artificial Sequence
<220> FEATURE:
<223> OTHER INFORMATION: synthetic

<400> SEQUENCE: 410

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
            20                  25                  30

Asn Tyr Tyr Trp Gly Trp Ile Arg Gln Pro Pro Gly Lys Gly Leu Glu
        35                  40                  45

Trp Phe Gly Thr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Arg Ala Ala Val Gly His Phe Asp Tyr Trp Gly Gln Gly
            100                 105                 110

Thr Leu Val Thr Val Ser Ser
        115

<210> SEQ ID NO 411
<211> LENGTH: 30
<212> TYPE: DNA
<213> ORGANISM: Artificial Sequence
<220> FEATURE:
<223> OTHER INFORMATION: synthetic

<400> SEQUENCE: 411
ggtggctcca tcagcagtgg taattactac                                    30

<210> SEQ ID NO 412
<211> LENGTH: 10
<212> TYPE: PRT
<213> ORGANISM: Artificial Sequence
<220> FEATURE:
<223> OTHER INFORMATION: synthetic

<400> SEQUENCE: 412

Gly Gly Ser Ile Ser Ser Gly Asn Tyr Tyr
1               5                   10

<210> SEQ ID NO 413
<211> LENGTH: 21
<212> TYPE: DNA
<213> ORGANISM: Artificial Sequence
<220> FEATURE:
<223> OTHER INFORMATION: synthetic

<400> SEQUENCE: 413
atctattata gtgggagcac c                                             21

<210> SEQ ID NO 414
<211> LENGTH: 7
<212> TYPE: PRT
<213> ORGANISM: Artificial Sequence
<220> FEATURE:
<223> OTHER INFORMATION: synthetic

<400> SEQUENCE: 414

Ile Tyr Tyr Ser Gly Ser Thr
1               5

<210> SEQ ID NO 415
<211> LENGTH: 33
<212> TYPE: DNA
<213> ORGANISM: Artificial Sequence
<220> FEATURE:
<223> OTHER INFORMATION: synthetic

<400> SEQUENCE: 415
gcgagacggg cagcagttgg tcactttgac tac                                33

<210> SEQ ID NO 416
<211> LENGTH: 11
<212> TYPE: PRT
<213> ORGANISM: Artificial Sequence
<220> FEATURE:
<223> OTHER INFORMATION: synthetic

<400> SEQUENCE: 416

Ala Arg Arg Ala Ala Val Gly His Phe Asp Tyr
1               5                   10

<210> SEQ ID NO 417
<211> LENGTH: 318
<212> TYPE: DNA

<213> ORGANISM: Artificial Sequence
<220> FEATURE:
<223> OTHER INFORMATION: synthetic

<400> SEQUENCE: 417

```
gacatccaga tgacccagtc tccttccacc ctgtctgcat ctgtaggaga cagagtcacc    60
atcacttgcc gggccagtca gagtattagt acctggttgg cctggtatca gcagaaacca   120
gggaaagccc ctaagctcct gatctatgag gcgtctagtt tagaaagtgg ggtcccatca   180
aggttcagcg gcagtggatt tgggacagaa ttcactctca ccatcagccg cctgcagcct   240
gatgattttg caacttattt ctgccaacag tataatactt attggacgtt cggccaaggg   300
accaaggtgg aaatcaaa                                                 318
```

<210> SEQ ID NO 418
<211> LENGTH: 106
<212> TYPE: PRT
<213> ORGANISM: Artificial Sequence
<220> FEATURE:
<223> OTHER INFORMATION: synthetic

<400> SEQUENCE: 418

```
Asp Ile Gln Met Thr Gln Ser Pro Ser Thr Leu Ser Ala Ser Val Gly
1               5                  10                  15

Asp Arg Val Thr Ile Thr Cys Arg Ala Ser Gln Ser Ile Ser Thr Trp
            20                  25                  30

Leu Ala Trp Tyr Gln Gln Lys Pro Gly Lys Ala Pro Lys Leu Leu Ile
        35                  40                  45

Tyr Glu Ala Ser Ser Leu Glu Ser Gly Val Pro Ser Arg Phe Ser Gly
    50                  55                  60

Ser Gly Phe Gly Thr Glu Phe Thr Leu Thr Ile Ser Arg Leu Gln Pro
65                  70                  75                  80

Asp Asp Phe Ala Thr Tyr Phe Cys Gln Gln Tyr Asn Thr Tyr Trp Thr
                85                  90                  95

Phe Gly Gln Gly Thr Lys Val Glu Ile Lys
            100                 105
```

<210> SEQ ID NO 419
<211> LENGTH: 18
<212> TYPE: DNA
<213> ORGANISM: Artificial Sequence
<220> FEATURE:
<223> OTHER INFORMATION: synthetic

<400> SEQUENCE: 419

```
cagagtatta gtacctgg                                                  18
```

<210> SEQ ID NO 420
<211> LENGTH: 6
<212> TYPE: PRT
<213> ORGANISM: Artificial Sequence
<220> FEATURE:
<223> OTHER INFORMATION: synthetic

<400> SEQUENCE: 420

```
Gln Ser Ile Ser Thr Trp
1               5
```

<210> SEQ ID NO 421
<211> LENGTH: 9
<212> TYPE: DNA
<213> ORGANISM: Artificial Sequence
<220> FEATURE:
<223> OTHER INFORMATION: synthetic

<400> SEQUENCE: 421 gaggcgtct                                                                9

<210> SEQ ID NO 422
<211> LENGTH: 3
<212> TYPE: PRT
<213> ORGANISM: Artificial Sequence
<220> FEATURE:
<223> OTHER INFORMATION: synthetic

<400> SEQUENCE: 422

Glu Ala Ser
1

<210> SEQ ID NO 423
<211> LENGTH: 24
<212> TYPE: DNA
<213> ORGANISM: Artificial Sequence
<220> FEATURE:
<223> OTHER INFORMATION: synthetic

<400> SEQUENCE: 423
caacagtata atacttattg gacg                                              24

<210> SEQ ID NO 424
<211> LENGTH: 8
<212> TYPE: PRT
<213> ORGANISM: Artificial Sequence
<220> FEATURE:
<223> OTHER INFORMATION: synthetic

<400> SEQUENCE: 424

Gln Gln Tyr Asn Thr Tyr Trp Thr
1               5

<210> SEQ ID NO 425
<211> LENGTH: 381
<212> TYPE: DNA
<213> ORGANISM: Artificial Sequence
<220> FEATURE:
<223> OTHER INFORMATION: synthetic

<400> SEQUENCE: 425
caggtccagc tggtgcagtc tggggctgag gtgaagaagc ctgggtcctc ggtgaaggtc        60
tcctgcaagg cttctggaga caccttcagc acctatgctg tcagctgggt acgtcaggcc      120
cctggacaag gcttgagtg gatgggaggg atcatccctt tctttggtac atcaaactac       180
gcacagaagt tccagggcag agtcacgatt accacgacg aatccacgac cacagcctac       240
atggaactga acagcctgag atctgaggac acggccgtat attactgtgc gagagaaatt      300
actatggttc ggggacttac caactaccac ttctacggta tggacgtctg gggccaaggg      360
accacggtca ccgtctcctc a                                                381

<210> SEQ ID NO 426
<211> LENGTH: 127
<212> TYPE: PRT
<213> ORGANISM: Artificial Sequence
<220> FEATURE:
<223> OTHER INFORMATION: synthetic

<400> SEQUENCE: 426

```
Gln Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Ser Thr Tyr
            20                  25                  30

Ala Val Ser Trp Val Arg Gln Ala Pro Gly Gln Gly Leu Glu Trp Met
        35                  40                  45

Gly Gly Ile Ile Pro Phe Phe Gly Thr Ser Asn Tyr Ala Gln Lys Phe
    50                  55                  60

Gln Gly Arg Val Thr Ile Thr Thr Asp Glu Ser Thr Thr Thr Ala Tyr
65                  70                  75                  80

Met Glu Leu Asn Ser Leu Arg Ser Glu Asp Thr Ala Val Tyr Tyr Cys
                85                  90                  95

Ala Arg Glu Ile Thr Met Val Arg Gly Leu Thr Asn Tyr His Phe Tyr
            100                 105                 110

Gly Met Asp Val Trp Gly Gln Gly Thr Thr Val Thr Val Ser Ser
                115                 120                 125
```

<210> SEQ ID NO 427
<211> LENGTH: 24
<212> TYPE: DNA
<213> ORGANISM: Artificial Sequence
<220> FEATURE:
<223> OTHER INFORMATION: synthetic

<400> SEQUENCE: 427
ggagacacct tcagcaccta tgct                                              24

<210> SEQ ID NO 428
<211> LENGTH: 8
<212> TYPE: PRT
<213> ORGANISM: Artificial Sequence
<220> FEATURE:
<223> OTHER INFORMATION: synthetic

<400> SEQUENCE: 428

Gly Asp Thr Phe Ser Thr Tyr Ala
1               5

<210> SEQ ID NO 429
<211> LENGTH: 24
<212> TYPE: DNA
<213> ORGANISM: Artificial Sequence
<220> FEATURE:
<223> OTHER INFORMATION: synthetic

<400> SEQUENCE: 429
atcatcccct tctttggtac atca                                              24

<210> SEQ ID NO 430
<211> LENGTH: 8
<212> TYPE: PRT
<213> ORGANISM: Artificial Sequence
<220> FEATURE:
<223> OTHER INFORMATION: synthetic

<400> SEQUENCE: 430

Ile Ile Pro Phe Phe Gly Thr Ser
1               5

<210> SEQ ID NO 431
<211> LENGTH: 60
<212> TYPE: DNA
<213> ORGANISM: Artificial Sequence

```
<220> FEATURE:
<223> OTHER INFORMATION: synthetic

<400> SEQUENCE: 431
gcgagagaaa ttactatggt tcggggactt accaactacc acttctacgg tatggacgtc    60

<210> SEQ ID NO 432
<211> LENGTH: 20
<212> TYPE: PRT
<213> ORGANISM: Artificial Sequence
<220> FEATURE:
<223> OTHER INFORMATION: synthetic

<400> SEQUENCE: 432

Ala Arg Glu Ile Thr Met Val Arg Gly Leu Thr Asn Tyr His Phe Tyr
1               5                   10                  15

Gly Met Asp Val
            20

<210> SEQ ID NO 433
<211> LENGTH: 324
<212> TYPE: DNA
<213> ORGANISM: Artificial Sequence
<220> FEATURE:
<223> OTHER INFORMATION: synthetic

<400> SEQUENCE: 433
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacagta tttccccgat caccttcggc   300
caggggacac gactggagat taaa                                          324

<210> SEQ ID NO 434
<211> LENGTH: 108
<212> TYPE: PRT
<213> ORGANISM: Artificial Sequence
<220> FEATURE:
<223> OTHER INFORMATION: synthetic

<400> SEQUENCE: 434

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ile Ser Pro
                85                  90                  95

Ile Thr Phe Gly Gln Gly Thr Arg Leu Glu Ile Lys
            100                 105

<210> SEQ ID NO 435
<211> LENGTH: 18
```

```
<212> TYPE: DNA
<213> ORGANISM: Artificial Sequence
<220> FEATURE:
<223> OTHER INFORMATION: synthetic

<400> SEQUENCE: 435
cagagcatta gcagctat                                                    18

<210> SEQ ID NO 436
<211> LENGTH: 6
<212> TYPE: PRT
<213> ORGANISM: Artificial Sequence
<220> FEATURE:
<223> OTHER INFORMATION: synthetic

<400> SEQUENCE: 436

Gln Ser Ile Ser Ser Tyr
1               5

<210> SEQ ID NO 437
<211> LENGTH: 9
<212> TYPE: DNA
<213> ORGANISM: Artificial Sequence
<220> FEATURE:
<223> OTHER INFORMATION: synthetic

<400> SEQUENCE: 437 gctgcatcc                                                               9

<210> SEQ ID NO 438
<211> LENGTH: 3
<212> TYPE: PRT
<213> ORGANISM: Artificial Sequence
<220> FEATURE:
<223> OTHER INFORMATION: synthetic

<400> SEQUENCE: 438

Ala Ala Ser
1

<210> SEQ ID NO 439
<211> LENGTH: 30
<212> TYPE: DNA
<213> ORGANISM: Artificial Sequence
<220> FEATURE:
<223> OTHER INFORMATION: synthetic

<400> SEQUENCE: 439
caacagagtt acagtatttc cccgatcacc                                       30

<210> SEQ ID NO 440
<211> LENGTH: 10
<212> TYPE: PRT
<213> ORGANISM: Artificial Sequence
<220> FEATURE:
<223> OTHER INFORMATION: synthetic

<400> SEQUENCE: 440

Gln Gln Ser Tyr Ser Ile Ser Pro Ile Thr
1               5                   10

<210> SEQ ID NO 441
<211> LENGTH: 381
<212> TYPE: DNA
<213> ORGANISM: Artificial Sequence
<220> FEATURE:
<223> OTHER INFORMATION: synthetic
```

<400> SEQUENCE: 441

```
caggtccagc tggttcagtc tggggctgag gtgaagaagc ctggttcctc ggtgaaggtc      60
tcctgcaagg cttctggggg caccttcaac aactatgcta tcagctgggt gcgacaggcc     120
cctggacaag gcttgaatg gatgggaggg atcatccctt tctttggtac aacaaactac     180
gcacagaagt tccaggacag agtcacgatt acctcggacg actcaacgat aacagcctac     240
atggaactga gtcgcctgag atctgaggac acggccgtgt attactgtgc gagagatgaa     300
ccccgtagag atggctacaa ttactaccac tactactata tggacgtctg gggccaaggg     360
accacggtca ccgtctcctc a                                                381
```

<210> SEQ ID NO 442
<211> LENGTH: 127
<212> TYPE: PRT
<213> ORGANISM: Artificial Sequence
<220> FEATURE:
<223> OTHER INFORMATION: synthetic

<400> SEQUENCE: 442

```
Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Asn Asn Tyr
            20                  25                  30
Ala Ile Ser Trp Val Arg Gln Ala Pro Gly Gln Gly Leu Glu Trp Met
        35                  40                  45
Gly Gly Ile Ile Pro Phe Phe Gly Thr Thr Asn Tyr Ala Gln Lys Phe
    50                  55                  60
Gln Asp Arg Val Thr Ile Thr Ser Asp Asp Ser Thr Ile Thr Ala Tyr
65                  70                  75                  80
Met Glu Leu Ser Arg Leu Arg Ser Glu Asp Thr Ala Val Tyr Tyr Cys
                85                  90                  95
Ala Arg Asp Glu Pro Arg Arg Asp Gly Tyr Asn Tyr Tyr His Tyr Tyr
            100                 105                 110
Tyr Met Asp Val Trp Gly Gln Gly Thr Thr Val Thr Val Ser Ser
        115                 120                 125
```

<210> SEQ ID NO 443
<211> LENGTH: 24
<212> TYPE: DNA
<213> ORGANISM: Artificial Sequence
<220> FEATURE:
<223> OTHER INFORMATION: synthetic

<400> SEQUENCE: 443

```
gggggcacct tcaacaacta tgct                                              24
```

<210> SEQ ID NO 444
<211> LENGTH: 8
<212> TYPE: PRT
<213> ORGANISM: Artificial Sequence
<220> FEATURE:
<223> OTHER INFORMATION: synthetic

<400> SEQUENCE: 444

```
Gly Gly Thr Phe Asn Asn Tyr Ala
1               5
```

<210> SEQ ID NO 445
<211> LENGTH: 24

<212> TYPE: DNA
<213> ORGANISM: Artificial Sequence
<220> FEATURE:
<223> OTHER INFORMATION: synthetic

<400> SEQUENCE: 445
atcatccctt tctttggtac aaca                                         24

<210> SEQ ID NO 446
<211> LENGTH: 8
<212> TYPE: PRT
<213> ORGANISM: Artificial Sequence
<220> FEATURE:
<223> OTHER INFORMATION: synthetic

<400> SEQUENCE: 446

Ile Ile Pro Phe Phe Gly Thr Thr
1               5

<210> SEQ ID NO 447
<211> LENGTH: 60
<212> TYPE: DNA
<213> ORGANISM: Artificial Sequence
<220> FEATURE:
<223> OTHER INFORMATION: synthetic

<400> SEQUENCE: 447
gcgagagatg aacccgtag agatggctac aattactacc actactacta tatggacgtc   60

<210> SEQ ID NO 448
<211> LENGTH: 20
<212> TYPE: PRT
<213> ORGANISM: Artificial Sequence
<220> FEATURE:
<223> OTHER INFORMATION: synthetic

<400> SEQUENCE: 448

Ala Arg Asp Glu Pro Arg Arg Asp Gly Tyr Asn Tyr Tyr His Tyr Tyr
1               5                   10                  15

Tyr Met Asp Val
            20

<210> SEQ ID NO 449
<211> LENGTH: 324
<212> TYPE: DNA
<213> ORGANISM: Artificial Sequence
<220> FEATURE:
<223> OTHER INFORMATION: synthetic

<400> SEQUENCE: 449
gacatccaga tgacccagtc tccatcctcc ctgtctgcat ctgtaggaga cagagtcacc   60
atcacttgcc gggcaagtca gagcattaac agctatttaa attggtatca gcagaaacca  120
gggaaagccc ctaacctcct gatctatgct gcatccagtt tgcaaagtgg ggtcccatca  180
aggttcagtg gcagtggatc tgggacagat ttcactctca ccatcagcag tctgcatcct  240
gaagattttg caacttacta ctgtcaacag agttacagta cccctccgat caccttcggc  300
caagggacac gactggagat taaa                                         324

<210> SEQ ID NO 450
<211> LENGTH: 108
<212> TYPE: PRT
<213> ORGANISM: Artificial Sequence
<220> FEATURE:
<223> OTHER INFORMATION: synthetic

<400> SEQUENCE: 450

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Ser Tyr
            20                  25                  30

Leu Asn Trp Tyr Gln Gln Lys Pro Gly Lys Ala Pro Asn Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu His Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
                100                 105

<210> SEQ ID NO 451
<211> LENGTH: 18
<212> TYPE: DNA
<213> ORGANISM: Artificial Sequence
<220> FEATURE:
<223> OTHER INFORMATION: synthetic

<400> SEQUENCE: 451
cagagcatta acagctat                                                 18

<210> SEQ ID NO 452
<211> LENGTH: 6
<212> TYPE: PRT
<213> ORGANISM: Artificial Sequence
<220> FEATURE:
<223> OTHER INFORMATION: synthetic

<400> SEQUENCE: 452

Gln Ser Ile Asn Ser Tyr
1               5

<210> SEQ ID NO 453
<211> LENGTH: 9
<212> TYPE: DNA
<213> ORGANISM: Artificial Sequence
<220> FEATURE:
<223> OTHER INFORMATION: synthetic

<400> SEQUENCE: 453 gctgcatcc                                                            9

<210> SEQ ID NO 454
<211> LENGTH: 3
<212> TYPE: PRT
<213> ORGANISM: Artificial Sequence
<220> FEATURE:
<223> OTHER INFORMATION: synthetic

<400> SEQUENCE: 454

Ala Ala Ser
1

<210> SEQ ID NO 455
<211> LENGTH: 30
<212> TYPE: DNA
<213> ORGANISM: Artificial Sequence
<220> FEATURE:
<223> OTHER INFORMATION: synthetic

<400> SEQUENCE: 455
caacagagtt acagtacccc tccgatcacc 30

<210> SEQ ID NO 456
<211> LENGTH: 10
<212> TYPE: PRT
<213> ORGANISM: Artificial Sequence
<220> FEATURE:
<223> OTHER INFORMATION: synthetic

<400> SEQUENCE: 456

Gln Gln Ser Tyr Ser Thr Pro Pro Ile Thr
1 5 10

<210> SEQ ID NO 457
<211> LENGTH: 1353
<212> TYPE: PRT
<213> ORGANISM: Artificial Sequence
<220> FEATURE:
<223> OTHER INFORMATION: MERS-CoV-S
aa 367-606: RBD

<400> SEQUENCE: 457

Met Ile His Ser Val Phe Leu Leu Met Phe Leu Leu Thr Pro Thr Glu
1 5 10 15

Ser Tyr Val Asp Val Gly Pro Asp Ser Val Lys Ser Ala Cys Ile Glu
20 25 30

Val Asp Ile Gln Gln Thr Phe Phe Asp Lys Thr Trp Pro Arg Pro Ile
35 40 45

Asp Val Ser Lys Ala Asp Gly Ile Ile Tyr Pro Gln Gly Arg Thr Tyr
50 55 60

Ser Asn Ile Thr Ile Thr Tyr Gln Gly Leu Phe Pro Tyr Gln Gly Asp
65 70 75 80

His Gly Asp Met Tyr Val Tyr Ser Ala Gly His Ala Thr Gly Thr Thr
85 90 95

Pro Gln Lys Leu Phe Val Ala Asn Tyr Ser Gln Asp Val Lys Gln Phe
100 105 110

Ala Asn Gly Phe Val Val Arg Ile Gly Ala Ala Ala Asn Ser Thr Gly
115 120 125

Thr Val Ile Ile Ser Pro Ser Thr Ser Ala Thr Ile Arg Lys Ile Tyr
130 135 140

Pro Ala Phe Met Leu Gly Ser Ser Val Gly Asn Phe Ser Asp Gly Lys
145 150 155 160

Met Gly Arg Phe Phe Asn His Thr Leu Val Leu Leu Pro Asp Gly Cys
165 170 175

Gly Thr Leu Leu Arg Ala Phe Tyr Cys Ile Leu Glu Pro Arg Ser Gly
180 185 190

Asn His Cys Pro Ala Gly Asn Ser Tyr Thr Ser Phe Ala Thr Tyr His
195 200 205

Thr Pro Ala Thr Asp Cys Ser Asp Gly Asn Tyr Asn Arg Asn Ala Ser
210 215 220

Leu Asn Ser Phe Lys Glu Tyr Phe Asn Leu Arg Asn Cys Thr Phe Met
225 230 235 240

Tyr Thr Tyr Asn Ile Thr Glu Asp Glu Ile Leu Glu Trp Phe Gly Ile
245 250 255

```
Thr Gln Thr Ala Gln Gly Val His Leu Phe Ser Ser Arg Tyr Val Asp
            260                 265                 270

Leu Tyr Gly Gly Asn Met Phe Gln Phe Ala Thr Leu Pro Val Tyr Asp
        275                 280                 285

Thr Ile Lys Tyr Tyr Ser Ile Ile Pro His Ser Ile Arg Ser Ile Gln
    290                 295                 300

Ser Asp Arg Lys Ala Trp Ala Ala Phe Tyr Val Tyr Lys Leu Gln Pro
305                 310                 315                 320

Leu Thr Phe Leu Leu Asp Phe Ser Val Asp Gly Tyr Ile Arg Arg Ala
                325                 330                 335

Ile Asp Cys Gly Phe Asn Asp Leu Ser Gln Leu His Cys Ser Tyr Glu
            340                 345                 350

Ser Phe Asp Val Glu Ser Gly Val Tyr Ser Val Ser Ser Phe Glu Ala
        355                 360                 365

Lys Pro Ser Gly Ser Val Val Glu Gln Ala Glu Gly Val Glu Cys Asp
    370                 375                 380

Phe Ser Pro Leu Leu Ser Gly Thr Pro Gln Val Tyr Asn Phe Lys
385                 390                 395                 400

Arg Leu Val Phe Thr Asn Cys Asn Tyr Asn Leu Thr Lys Leu Leu Ser
                405                 410                 415

Leu Phe Ser Val Asn Asp Phe Thr Cys Ser Gln Ile Ser Pro Ala Ala
            420                 425                 430

Ile Ala Ser Asn Cys Tyr Ser Ser Leu Ile Leu Asp Tyr Phe Ser Tyr
        435                 440                 445

Pro Leu Ser Met Lys Ser Asp Leu Ser Val Ser Ser Ala Gly Pro Ile
    450                 455                 460

Ser Gln Phe Asn Tyr Lys Gln Ser Phe Ser Asn Pro Thr Cys Leu Ile
465                 470                 475                 480

Leu Ala Thr Val Pro His Asn Leu Thr Thr Ile Thr Lys Pro Leu Lys
                485                 490                 495

Tyr Ser Tyr Ile Asn Lys Cys Ser Arg Leu Leu Ser Asp Asp Arg Thr
            500                 505                 510

Glu Val Pro Gln Leu Val Asn Ala Asn Gln Tyr Ser Pro Cys Val Ser
        515                 520                 525

Ile Val Pro Ser Thr Val Trp Glu Asp Gly Asp Tyr Tyr Arg Lys Gln
    530                 535                 540

Leu Ser Pro Leu Glu Gly Gly Gly Trp Leu Val Ala Ser Gly Ser Thr
545                 550                 555                 560

Val Ala Met Thr Glu Gln Leu Gln Met Gly Phe Gly Ile Thr Val Gln
                565                 570                 575

Tyr Gly Thr Asp Thr Asn Ser Val Cys Pro Lys Leu Glu Phe Ala Asn
            580                 585                 590

Asp Thr Lys Ile Ala Ser Gln Leu Gly Asn Cys Val Glu Tyr Ser Leu
        595                 600                 605

Tyr Gly Val Ser Gly Arg Gly Val Phe Gln Asn Cys Thr Ala Val Gly
    610                 615                 620

Val Arg Gln Gln Arg Phe Val Tyr Asp Ala Tyr Gln Asn Leu Val Gly
625                 630                 635                 640

Tyr Tyr Ser Asp Asp Gly Asn Tyr Tyr Cys Leu Arg Ala Cys Val Ser
                645                 650                 655

Val Pro Val Ser Val Ile Tyr Asp Lys Glu Thr Lys Thr His Ala Thr
            660                 665                 670

Leu Phe Gly Ser Val Ala Cys Glu His Ile Ser Ser Thr Met Ser Gln
```

-continued

```
            675                 680                 685
Tyr Ser Arg Ser Thr Arg Ser Met Leu Lys Arg Arg Asp Ser Thr Tyr
690                 695                 700
Gly Pro Leu Gln Thr Pro Val Gly Cys Val Leu Gly Leu Val Asn Ser
705                 710                 715                 720
Ser Leu Phe Val Glu Asp Cys Lys Leu Pro Leu Gly Gln Ser Leu Cys
                725                 730                 735
Ala Leu Pro Asp Thr Pro Ser Thr Leu Thr Pro Arg Ser Val Arg Ser
                740                 745                 750
Val Pro Gly Glu Met Arg Leu Ala Ser Ile Ala Phe Asn His Pro Ile
                755                 760                 765
Gln Val Asp Gln Leu Asn Ser Ser Tyr Phe Lys Leu Ser Ile Pro Thr
770                 775                 780
Asn Phe Ser Phe Gly Val Thr Gln Glu Tyr Ile Gln Thr Thr Ile Gln
785                 790                 795                 800
Lys Val Thr Val Asp Cys Lys Gln Tyr Val Cys Asn Gly Phe Gln Lys
                805                 810                 815
Cys Glu Gln Leu Leu Arg Glu Tyr Gly Gln Phe Cys Ser Lys Ile Asn
                820                 825                 830
Gln Ala Leu His Gly Ala Asn Leu Arg Gln Asp Asp Ser Val Arg Asn
                835                 840                 845
Leu Phe Ala Ser Val Lys Ser Ser Gln Ser Ser Pro Ile Ile Pro Gly
                850                 855                 860
Phe Gly Gly Asp Phe Asn Leu Thr Leu Leu Glu Pro Val Ser Ile Ser
865                 870                 875                 880
Thr Gly Ser Arg Ser Ala Arg Ser Ala Ile Glu Asp Leu Leu Phe Asp
                885                 890                 895
Lys Val Thr Ile Ala Asp Pro Gly Tyr Met Gln Gly Tyr Asp Asp Cys
                900                 905                 910
Met Gln Gln Gly Pro Ala Ser Ala Arg Asp Leu Ile Cys Ala Gln Tyr
                915                 920                 925
Val Ala Gly Tyr Lys Val Leu Pro Pro Leu Met Asp Val Asn Met Glu
                930                 935                 940
Ala Ala Tyr Thr Ser Ser Leu Leu Gly Ser Ile Ala Gly Val Gly Trp
945                 950                 955                 960
Thr Ala Gly Leu Ser Ser Phe Ala Ala Ile Pro Phe Ala Gln Ser Ile
                965                 970                 975
Phe Tyr Arg Leu Asn Gly Val Gly Ile Thr Gln Gln Val Leu Ser Glu
                980                 985                 990
Asn Gln Lys Leu Ile Ala Asn Lys Phe Asn Gln Ala Leu Gly Ala Met
                995                 1000                1005
Gln Thr Gly Phe Thr Thr Thr Asn Glu Ala Phe Gln Lys Val Gln Asp
                1010                1015                1020
Ala Val Asn Asn Asn Ala Gln Ala Leu Ser Lys Leu Ala Ser Glu Leu
1025                1030                1035                1040
Ser Asn Thr Phe Gly Ala Ile Ser Ala Ser Ile Gly Asp Ile Ile Gln
                1045                1050                1055
Arg Leu Asp Val Leu Glu Gln Asp Ala Gln Ile Asp Arg Leu Ile Asn
                1060                1065                1070
Gly Arg Leu Thr Thr Leu Asn Ala Phe Val Ala Gln Gln Leu Val Arg
                1075                1080                1085
Ser Glu Ser Ala Ala Leu Ser Ala Gln Leu Ala Lys Asp Lys Val Asn
                1090                1095                1100
```

Glu Cys Val Lys Ala Gln Ser Lys Arg Ser Gly Phe Cys Gly Gln Gly
1105 1110 1115 1120

Thr His Ile Val Ser Phe Val Val Asn Ala Pro Asn Gly Leu Tyr Phe
1125 1130 1135

Met His Val Gly Tyr Tyr Pro Ser Asn His Ile Glu Val Val Ser Ala
1140 1145 1150

Tyr Gly Leu Cys Asp Ala Ala Asn Pro Thr Asn Cys Ile Ala Pro Val
1155 1160 1165

Asn Gly Tyr Phe Ile Lys Thr Asn Asn Thr Arg Ile Val Asp Glu Trp
1170 1175 1180

Ser Tyr Thr Gly Ser Ser Phe Tyr Ala Pro Glu Pro Ile Thr Ser Leu
1185 1190 1195 1200

Asn Thr Lys Tyr Val Ala Pro Gln Val Thr Tyr Gln Asn Ile Ser Thr
1205 1210 1215

Asn Leu Pro Pro Pro Leu Leu Gly Asn Ser Thr Gly Ile Asp Phe Gln
1220 1225 1230

Asp Glu Leu Asp Glu Phe Phe Lys Asn Val Ser Thr Ser Ile Pro Asn
1235 1240 1245

Phe Gly Ser Leu Thr Gln Ile Asn Thr Thr Leu Leu Asp Leu Thr Tyr
1250 1255 1260

Glu Met Leu Ser Leu Gln Gln Val Val Lys Ala Leu Asn Glu Ser Tyr
1265 1270 1275 1280

Ile Asp Leu Lys Glu Leu Gly Asn Tyr Thr Tyr Tyr Asn Lys Trp Pro
1285 1290 1295

Trp Tyr Ile Trp Leu Gly Phe Ile Ala Gly Leu Val Ala Leu Ala Leu
1300 1305 1310

Cys Val Phe Phe Ile Leu Cys Cys Thr Gly Cys Gly Thr Asn Cys Met
1315 1320 1325

Gly Lys Leu Lys Cys Asn Arg Cys Cys Asp Arg Tyr Glu Glu Tyr Asp
1330 1335 1340

Leu Glu Pro His Lys Val His Val His
1345 1350

<210> SEQ ID NO 458
<211> LENGTH: 467
<212> TYPE: PRT
<213> ORGANISM: Artificial Sequence
<220> FEATURE:
<223> OTHER INFORMATION: MERS RBD-hFc
aa1-240: MERS RBD
aa241-467: hFc

<400> SEQUENCE: 458

Glu Ala Lys Pro Ser Gly Ser Val Val Glu Gln Ala Glu Gly Val Glu
1 5 10 15

Cys Asp Phe Ser Pro Leu Leu Ser Gly Thr Pro Pro Gln Val Tyr Asn
20 25 30

Phe Lys Arg Leu Val Phe Thr Asn Cys Asn Tyr Asn Leu Thr Lys Leu
35 40 45

Leu Ser Leu Phe Ser Val Asn Asp Phe Thr Cys Ser Gln Ile Ser Pro
50 55 60

Ala Ala Ile Ala Ser Asn Cys Tyr Ser Ser Leu Ile Leu Asp Tyr Phe
65 70 75 80

Ser Tyr Pro Leu Ser Met Lys Ser Asp Leu Ser Val Ser Ser Ala Gly
85 90 95

```
Pro Ile Ser Gln Phe Asn Tyr Lys Gln Ser Phe Ser Asn Pro Thr Cys
            100                 105                 110

Leu Ile Leu Ala Thr Val Pro His Asn Leu Thr Thr Ile Thr Lys Pro
            115                 120                 125

Leu Lys Tyr Ser Tyr Ile Asn Lys Cys Ser Arg Leu Leu Ser Asp Asp
            130                 135                 140

Arg Thr Glu Val Pro Gln Leu Val Asn Ala Asn Gln Tyr Ser Pro Cys
145                 150                 155                 160

Val Ser Ile Val Pro Ser Thr Val Trp Glu Asp Gly Asp Tyr Tyr Arg
                165                 170                 175

Lys Gln Leu Ser Pro Leu Glu Gly Gly Gly Trp Leu Val Ala Ser Gly
            180                 185                 190

Ser Thr Val Ala Met Thr Glu Gln Leu Gln Met Gly Phe Gly Ile Thr
        195                 200                 205

Val Gln Tyr Gly Thr Asp Thr Asn Ser Val Cys Pro Lys Leu Glu Phe
        210                 215                 220

Ala Asn Asp Thr Lys Ile Ala Ser Gln Leu Gly Asn Cys Val Glu Tyr
225                 230                 235                 240

Asp Lys Thr His Thr Cys Pro Pro Cys Pro Ala Pro Glu Leu Leu Gly
            245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
        450                 455                 460

Pro Gly Lys
465
```

HUMAN ANTIBODIES TO MIDDLE EAST RESPIRATORY SYNDROME—CORONAVIRUS SPIKE PROTEIN

CROSS-REFERENCE TO RELATED APPLICATIONS

This application is a continuation of U.S. application Ser. No. 14/717,760, filed May 20, 2015, which claims the benefit under 35 U.S.C. § 119(e) of U.S. provisional application Nos. 62/002,233, filed on May 23, 2014; 62/004,971, filed on May 30, 2014; 62/051,717, filed on Sep. 17, 2014; and 62/072,716, filed on Oct. 30, 2014, the disclosures of each herein incorporated by reference in their entireties.

SEQUENCE STATEMENT

The instant application contains a Sequence Listing, which has been submitted electronically in ASCII format and is hereby incorporated by reference in its entirety. Said ASCII copy, created on Jun. 23, 2017, is named SquenceList.TXT and is 165,296 bytes in size.

FIELD OF THE INVENTION

The present invention is related to human antibodies and antigen-binding fragments of human antibodies that specifically bind to the spike protein of the Middle East Respiratory Syndrome-coronavirus (MERS-CoV), and therapeutic and diagnostic methods of using those antibodies.

STATEMENT OF RELATED ART

Middle East Respiratory Syndrome-Coronavirus (MERS-CoV) is a newly-emergent betacoronavirus which causes severe acute respiratory disease. It was first isolated in Saudi Arabia in 2012 (Zaki et al 2012, NEJM 367: 1814-1820) and since then has spread to about 18 countries with most of the cases in Saudi Arabia and United Arab Emirates. As of May 15, 2014, the World Health Organization reported 571 cases of MERS, including 171 deaths. Two cases of MERS infection have recently been discovered in the US. Clinical features of MERS-CoV infection in humans range from an asymptomatic infection to very severe pneumonia, with potential development of acute respiratory distress syndrome, septic shock and multi-organ failure resulting in death.

MERS-CoV shares similarity with bat coronaviruses HKU4 and HKU5. The virus uses its spike protein for interaction with a cellular receptor for entry into a target cell. Raj et al showed that the virus binds via the receptor binding domain of its spike protein to dipeptidyl peptidase 4 (DPP4) on human epithelial and endothelial cells (Raj et al 2013, Nature 495: 251-256). Lu et al 2013 have shown that MERS-CoV receptor binding domain consists of a core and a receptor binding subdomain that interacts with DPP4 (Lu et al 2013, Nature 500: 227-231).

WO2014/045254 describes the isolation and characterization of MERS-CoV, spike protein and polyclonal antibodies against the receptor binding domain of the spike protein. Neutralizing monoclonal antibodies to the receptor binding domain of the spike protein have been disclosed by, e.g., Du et al (2014, J. Virol.), Ying et al (2014, J. Virol.), Tang, et al., (2014, PNAS) and Jiang et al (2014, Sci. Transl. Med. Vol. 6, 234ra59).

Thus far, there has been no vaccine or therapeutic agent to prevent or treat MERS infection. In view of the continuing threat to human health and high fatality rate (over 30%), there is an urgent need for preventive and therapeutic antiviral therapies for MERS control. Fully human antibodies that specifically bind to MERS-CoV spike protein with high affinity and inhibit virus infectivity could be important in the prevention and treatment of MERS infection.

BRIEF SUMMARY OF THE INVENTION

The present invention provides antibodies and antigen-binding fragments thereof that bind MERS-CoV spike protein. The antibodies of the present invention are useful, inter alia, for inhibiting or neutralizing the activity of MERS-CoV spike protein. In some embodiments, the antibodies are useful for blocking binding of the virus to its host cell receptor dipeptidyl peptidase 4 (DPP4) and for preventing the entry of MERS-Corona virus into host cells. In some embodiments, the antibodies function by inhibiting the cell-to-cell transmission of the virus. In certain embodiments, the antibodies are useful in preventing, treating or ameliorating at least one symptom of MERS-CoV infection in a subject. In certain embodiments, the antibodies may be administered prophylactically or therapeutically to a subject having or at risk of having MERS-CoV infection.

The antibodies of the invention can be full-length (for example, an IgG1 or IgG4 antibody) or may comprise only an antigen-binding portion (for example, a Fab, F(ab')$_2$ or scFv fragment), and may be modified to affect functionality, e.g., to increase persistence in the host or to eliminate residual effector functions (Reddy et al., 2000, J. Immunol. 164:1925-1933). In certain embodiments, the antibodies may be bispecific.

In a first aspect, the present invention provides isolated recombinant monoclonal antibodies or antigen-binding fragments thereof that bind specifically to the MERS-CoV spike protein. In some embodiments, the antibodies are fully human monoclonal antibodies. The antibodies and antigen-binding fragments thereof of the invention bind to an epitope within the receptor binding domain (RBD) of the spike protein of MERS-CoV. In some embodiments, the present invention provides antibodies and antigen-binding fragments thereof that bind to an amino acid selected from the amino acids 367 to 606 of GenBank Accession No. AFS88936.1 (SEQ ID NO: 457). In one embodiment, the antibodies of the present invention bind to the spike protein of MERS-CoV isolate EMC/2012. In certain embodiments, the antibodies bind to spike protein of different MERS-CoV isolates.

Exemplary anti-MERS-CoV-S antibodies of the present invention are listed in Tables 2 and 3 herein. Table 2 sets forth the amino acid sequence identifiers of the heavy chain variable regions (HCVRs), light chain variable regions (LCVRs), heavy chain complementarity determining regions (HCDR1, HCDR2 and HCDR3), and light chain complementarity determining regions (LCDR1, LCDR2 and LCDR3) of exemplary anti-MERS-CoV-S antibodies. Table 3 sets forth the nucleic acid sequence identifiers of the HCVRs, LCVRs, HCDR1, HCDR2 HCDR3, LCDR1, LCDR2 and LCDR3 of the exemplary anti-MERS-CoV-S antibodies.

The present invention provides antibodies, or antigen-binding fragments thereof, comprising an HCVR comprising an amino acid sequence selected from any of the HCVR amino acid sequences listed in Table 2, or a substantially similar sequence thereof having at least 90%, at least 95%, at least 98% or at least 99% sequence identity thereto.

The present invention also provides antibodies, or antigen-binding fragments thereof, comprising an LCVR comprising an amino acid sequence selected from any of the LCVR amino acid sequences listed in Table 2, or a substantially similar sequence thereof having at least 90%, at least 95%, at least 98% or at least 99% sequence identity thereto.

The present invention also provides antibodies, or antigen-binding fragments thereof, comprising an HCVR and an LCVR amino acid sequence pair (HCVR/LCVR) comprising any of the HCVR amino acid sequences listed in Table 2 paired with any of the LCVR amino acid sequences listed in Table 2. According to certain embodiments, the present invention provides antibodies, or antigen-binding fragments thereof, comprising an HCVR/LCVR amino acid sequence pair contained within any of the exemplary anti-MERS-CoV-S antibodies listed in Table 2. In certain embodiments, the HCVR/LCVR amino acid sequence pair is selected from the group consisting of SEQ ID NOs: 2/10, 18/26, 34/42, 50/58, 66/74, 82/90, 98/106, 114/106, 122/106, 130/106, 138/106, 146/106, 154/162, 170/162, 178/162, 186/194, 202/210, 218/226, 234/242, 250/258, 266/274, 282/290, 298/306, 314/322, 330/338, 346/354, 362/370, 378/386, 394/402, 410/418, 426/434, and 442/450. In certain embodiments, the HCVR/LCVR amino acid sequence pair is selected from one of SEQ ID NOs: 2/10 (e.g., H1H15177P), 18/26 (e.g., H1H15188P), 66/74 (e.g., H1H15211P), 114/106 (e.g., H1H15231P2), 170/162 (e.g., H1H15260P2) or 218/226 (e.g., H1H15277N).

The present invention also provides antibodies, or antigen-binding fragments thereof, comprising a heavy chain CDR1 (HCDR1) comprising an amino acid sequence selected from any of the HCDR1 amino acid sequences listed in Table 2 or a substantially similar sequence thereof having at least 90%, at least 95%, at least 98% or at least 99% sequence identity.

The present invention also provides antibodies, or antigen-binding fragments thereof, comprising a heavy chain CDR2 (HCDR2) comprising an amino acid sequence selected from any of the HCDR2 amino acid sequences listed in Table 2 or a substantially similar sequence thereof having at least 90%, at least 95%, at least 98% or at least 99% sequence identity.

The present invention also provides antibodies, or antigen-binding fragments thereof, comprising a heavy chain CDR3 (HCDR3) comprising an amino acid sequence selected from any of the HCDR3 amino acid sequences listed in Table 2 or a substantially similar sequence thereof having at least 90%, at least 95%, at least 98% or at least 99% sequence identity.

The present invention also provides antibodies, or antigen-binding fragments thereof, comprising a light chain CDR1 (LCDR1) comprising an amino acid sequence selected from any of the LCDR1 amino acid sequences listed in Table 2 or a substantially similar sequence thereof having at least 90%, at least 95%, at least 98% or at least 99% sequence identity.

The present invention also provides antibodies, or antigen-binding fragments thereof, comprising a light chain CDR2 (LCDR2) comprising an amino acid sequence selected from any of the LCDR2 amino acid sequences listed in Table 2 or a substantially similar sequence thereof having at least 90%, at least 95%, at least 98% or at least 99% sequence identity.

The present invention also provides antibodies, or antigen-binding fragments thereof, comprising a light chain CDR3 (LCDR3) comprising an amino acid sequence selected from any of the LCDR3 amino acid sequences listed in Table 2 or a substantially similar sequence thereof having at least 90%, at least 95%, at least 98% or at least 99% sequence identity.

The present invention also provides antibodies, or antigen-binding fragments thereof, comprising an HCDR3 and an LCDR3 amino acid sequence pair (HCDR3/LCDR3) comprising any of the HCDR3 amino acid sequences listed in Table 2 paired with any of the LCDR3 amino acid sequences listed in Table 2. According to certain embodiments, the present invention provides antibodies, or antigen-binding fragments thereof, comprising an HCDR3/LCDR3 amino acid sequence pair contained within any of the exemplary anti-MERS-CoV-S antibodies listed in Table 2. In certain embodiments, the HCDR3/LCDR3 amino acid sequence pair is selected from the group consisting of SEQ ID NOs: 8/16 (e.g., H1H15177P), 24/32 (e.g., H1H15188P), 72/80 (e.g., H1H15211P), 120/112 (e.g., H1H15231P2), 176/168 (e.g., H1H15260P2) and 224/232 (e.g., H1H15277N).

The present invention also provides antibodies, or antigen-binding fragments thereof, comprising a set of six CDRs (i.e., HCDR1-HCDR2-HCDR3-LCDR1-LCDR2-LCDR3) contained within any of the exemplary anti-MERS-CoV-S antibodies listed in Table 2. In certain embodiments, the HCDR1-HCDR2-HCDR3-LCDR1-LCDR2-LCDR3 amino acid sequence set is selected from the group consisting of SEQ ID NOs: 4-6-8-12-14-16 (e.g., H1H15177P), 20-22-24-28-30-32 (e.g., H1H15188P); 68-70-72-76-78-80 (e.g., H1H15211P); 116-118-120-108-110-112 (e.g., H1H15231P2); 172-174-176-164-166-168 (e.g., H1H15260P2) and 220-222-224-228-230-232 (e.g., H1H15277N).

In a related embodiment, the present invention provides antibodies, or antigen-binding fragments thereof, comprising a set of six CDRs (i.e., HCDR1-HCDR2-HCDR3-LCDR1-LCDR2-LCDR3) contained within an HCVR/LCVR amino acid sequence pair as defined by any of the exemplary anti-MERS-CoV-S antibodies listed in Table 2. For example, the present invention includes antibodies, or antigen-binding fragments thereof, comprising the HCDR1-HCDR2-HCDR3-LCDR1-LCDR2-LCDR3 amino acid sequences set contained within an HCVR/LCVR amino acid sequence pair selected from the group consisting of SEQ ID NOs: 2/10 (e.g., H1H15177P), 18/26 (e.g., H1H15188P); 66/74 (e.g., H1H15211P); 114/106 (e.g., H1H15231P2); 170/162 (e.g., H1H15260P2) and 218/226 (e.g., H1H15277N). Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

The present invention includes anti-MERS-CoV-S antibodies having a modified glycosylation pattern. In some embodiments, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277:26733). In other applications, modification of galactosylation can be made in order to modify complement dependent cytotoxicity (CDC).

The present invention also provides for antibodies and antigen-binding fragments thereof that compete for specific binding to MERS-CoV-S with an antibody or antigen-binding fragment thereof comprising the CDRs of a HCVR and the CDRs of a LCVR, wherein the HCVR and LCVR each has an amino acid sequence selected from the HCVR and LCVR sequences listed in Table 2.

The present invention also provides antibodies and antigen-binding fragments thereof that cross-compete for binding to MERS-CoV-S with a reference antibody or antigen-binding fragment thereof comprising the CDRs of a HCVR and the CDRs of a LCVR, wherein the HCVR and LCVR each has an amino acid sequence selected from the HCVR and LCVR sequences listed in Table 2.

In some embodiments, the antibody or antigen binding fragment thereof may bind specifically to MERS-CoV-S in an agonist manner, i.e., it may enhance or stimulate MERS-CoV-S binding and/or activity; in other embodiments, the antibody may bind specifically to MERS-CoV-S in an antagonist manner, i.e., it may block MERS-CoV-S from binding to its receptor (DPP4).

The present invention also provides isolated antibodies and antigen-binding fragments thereof that block MERS-CoV spike protein binding to DPP4. In some embodiments, the antibody or antigen-binding fragment thereof that blocks MERS-CoV spike protein binding to DPP4 may bind to the same epitope on MERS-CoV spike protein as DPP4 or may bind to a different epitope on MERS-CoV spike protein as DPP4. In some embodiments, the present invention provides antibodies or antigen-binding fragments thereof that block the binding of MERS-CoV-S to human, camel or bat DPP4.

In certain embodiments, the antibodies or antigen-binding fragments of the present invention are bispecific comprising a first binding specificity to a first epitope in the receptor binding domain of MERS-CoV spike protein and a second binding specificity to a second epitope in the receptor binding domain of MERS-CoV spike protein wherein the first and second epitopes are distinct and non-overlapping.

In one embodiment, the invention provides an isolated antibody or antigen-binding fragment that has one or more of the following characteristics: (a) is a fully human monoclonal antibody; (b) is isolated from a hybridoma cell line selected from the group consisting of HBVX06H05, HBVX11H04, HBVX11D02, HBVZ10E10, HBVY09F08, HBVZ05G02, HBVZ09B06, HBVY01F08, HBVY10G02, HBVY04B06, HBVY07D10, HBVZ08A09, HBVZ05G04, HBVY06C07, HBVY03H06, HBVZ10G06, HBVZ04F10, HBVX11E09, HBVY06H09, HBVZ05B11, HBVY02E05 and HBVZ04C07; (c) interacts with one or more amino acid residues in the receptor binding domain of MERS-CoV spike protein selected from amino acid residues 367 to 606 of SEQ ID NO: 457; (d) binds to MERS-CoV spike protein with a dissociation constant ($K_D$) of less than $10^{-9}$M, as measured in a surface plasmon resonance assay; (e) blocks binding of MERS-CoV spike protein to dipeptidyl peptidase 4 (DPP4) by more than 90%, as measured in a blocking ELISA assay; (f) neutralizes MERS-CoV infectivity of human host cells by more than 90% and with an $IC_{50}$ less than 4 nM, as measured in a virus-like particle (VLP) neutralization assay; (g) neutralizes MERS-CoV infectivity wherein the MERS-CoV comprises an isolate of the virus selected from the group consisting of EMC/2012, Jordan-N3/2012, England-Qatar/2012, Al-Hasa_1_2013, Al-Hasa_2_2013, Al-Hasa_3_2013, Al-Hasa_4_2013, Al-Hasa_12, Al-Hasa_15, Al-Hasa_16, Al-Hasa_17, Al-Hasa_18, Al-Hasa_19, Al-Hasa_21, Al-hasa_25, Bisha_1, Buraidah_1, England 1, Hafr-Al-batin_1, Hafr-Al-Batin_2, Hafr-Al-Batin_6, Jeddah_1, KFU-HKU 1, KFU-HKU 13, Munich, Qatar3, Qatar4, Riyadh_1, Riyadh_2, Riyadh_3, Riyadh_3, Riyadh_4, Riyadh_5, Riyadh_9, Riyadh_14, Taif_1, UAE, and Wadi-Ad-Dawasir; and (h) is a bi-specific antibody comprising a first binding specificity to a first epitope in the receptor binding domain of MERS-CoV spike protein and a second binding specificity to a second epitope in the receptor binding domain of MERS-CoV spike protein wherein the first and second epitopes are distinct and non-overlapping.

In a second aspect, the present invention provides nucleic acid molecules encoding anti-MERS-CoV-S antibodies or portions thereof. For example, the present invention provides nucleic acid molecules encoding any of the HCVR amino acid sequences listed in Table 2; in certain embodiments the nucleic acid molecule comprises a polynucleotide sequence selected from any of the HCVR nucleic acid sequences listed in Table 3, or a substantially similar sequence thereof having at least 90%, at least 95%, at least 98% or at least 99% sequence identity thereto.

The present invention also provides nucleic acid molecules encoding any of the LCVR amino acid sequences listed in Table 2; in certain embodiments the nucleic acid molecule comprises a polynucleotide sequence selected from any of the LCVR nucleic acid sequences listed in Table 3, or a substantially similar sequence thereof having at least 90%, at least 95%, at least 98% or at least 99% sequence identity thereto.

The present invention also provides nucleic acid molecules encoding any of the HCDR1 amino acid sequences listed in Table 2; in certain embodiments the nucleic acid molecule comprises a polynucleotide sequence selected from any of the HCDR1 nucleic acid sequences listed in Table 3, or a substantially similar sequence thereof having at least 90%, at least 95%, at least 98% or at least 99% sequence identity thereto.

The present invention also provides nucleic acid molecules encoding any of the HCDR2 amino acid sequences listed in Table 2; in certain embodiments the nucleic acid molecule comprises a polynucleotide sequence selected from any of the HCDR2 nucleic acid sequences listed in Table 3, or a substantially similar sequence thereof having at least 90%, at least 95%, at least 98% or at least 99% sequence identity thereto.

The present invention also provides nucleic acid molecules encoding any of the HCDR3 amino acid sequences listed in Table 2; in certain embodiments the nucleic acid molecule comprises a polynucleotide sequence selected from any of the HCDR3 nucleic acid sequences listed in Table 3, or a substantially similar sequence thereof having at least 90%, at least 95%, at least 98% or at least 99% sequence identity thereto.

The present invention also provides nucleic acid molecules encoding any of the LCDR1 amino acid sequences listed in Table 2; in certain embodiments the nucleic acid molecule comprises a polynucleotide sequence selected from any of the LCDR1 nucleic acid sequences listed in Table 3, or a substantially similar sequence thereof having at least 90%, at least 95%, at least 98% or at least 99% sequence identity thereto.

The present invention also provides nucleic acid molecules encoding any of the LCDR2 amino acid sequences listed in Table 2; in certain embodiments the nucleic acid molecule comprises a polynucleotide sequence selected from any of the LCDR2 nucleic acid sequences listed in Table 3, or a substantially similar sequence thereof having at least 90%, at least 95%, at least 98% or at least 99% sequence identity thereto.

The present invention also provides nucleic acid molecules encoding any of the LCDR3 amino acid sequences listed in Table 2; in certain embodiments the nucleic acid molecule comprises a polynucleotide sequence selected from any of the LCDR3 nucleic acid sequences listed in Table 3, or a substantially similar sequence thereof having at least 90%, at least 95%, at least 98% or at least 99% sequence identity thereto.

The present invention also provides nucleic acid molecules encoding an HCVR, wherein the HCVR comprises a set of three CDRs (i.e., HCDR1-HCDR2-HCDR3), wherein the HCDR1-HCDR2-HCDR3 amino acid sequence set is as defined by any of the exemplary anti-MERS-CoV-S antibodies listed in Table 2.

The present invention also provides nucleic acid molecules encoding an LCVR, wherein the LCVR comprises a set of three CDRs (i.e., LCDR1-LCDR2-LCDR3), wherein the LCDR1-LCDR2-LCDR3 amino acid sequence set is as defined by any of the exemplary anti-MERS-CoV-S antibodies listed in Table 2.

The present invention also provides nucleic acid molecules encoding both an HCVR and an LCVR, wherein the HCVR comprises an amino acid sequence of any of the HCVR amino acid sequences listed in Table 2, and wherein the LCVR comprises an amino acid sequence of any of the LCVR amino acid sequences listed in Table 2. In certain embodiments, the nucleic acid molecule comprises a polynucleotide sequence selected from any of the HCVR nucleic acid sequences listed in Table 3, or a substantially similar sequence thereof having at least 90%, at least 95%, at least 98% or at least 99% sequence identity thereto, and a polynucleotide sequence selected from any of the LCVR nucleic acid sequences listed in Table 2, or a substantially similar sequence thereof having at least 90%, at least 95%, at least 98% or at least 99% sequence identity thereto. In certain embodiments according to this aspect of the invention, the nucleic acid molecule encodes an HCVR and LCVR, wherein the HCVR and LCVR are both derived from the same anti-MERS-CoV-S antibody listed in Table 2.

The present invention provides nucleic acid molecules encoding any of the heavy chain amino acid sequences listed in Table 2. The present invention also provides nucleic acid molecules encoding any of the light chain amino acid sequences listed in Table 2.

In a related aspect, the present invention provides recombinant expression vectors capable of expressing a polypeptide comprising a heavy or light chain variable region of an anti-MERS-CoV-S antibody. For example, the present invention includes recombinant expression vectors comprising any of the nucleic acid molecules mentioned above, i.e., nucleic acid molecules encoding any of the HCVR, LCVR, and/or CDR sequences as set forth in Table 3. Also included within the scope of the present invention are host cells into which such vectors have been introduced, as well as methods of producing the antibodies or portions thereof by culturing the host cells under conditions permitting production of the antibodies or antibody fragments, and recovering the antibodies and antibody fragments so produced.

In a third aspect, the invention provides a pharmaceutical composition comprising a therapeutically effective amount of at least one recombinant monoclonal antibody or antigen-binding fragment thereof which specifically binds MERS-CoV spike protein and a pharmaceutically acceptable carrier. In a related aspect, the invention features a composition which is a combination of an anti-MERS-CoV-S antibody and a second therapeutic agent. In one embodiment, the second therapeutic agent is any agent that is advantageously combined with an anti-MERS-Co-V-S antibody. Exemplary agents that may be advantageously combined with an anti-MERS-CoV-S antibody include, without limitation, other agents that bind and/or inhibit MERS-CoV activity (including other antibodies or antigen-binding fragments thereof, etc.) and/or agents which do not directly bind MERS-CoV-S but nonetheless inhibit viral activity including infectivity of host cells. In certain embodiments, the invention provides for a pharmaceutical composition comprising: (a) a first anti-MERS-CoV-S antibody or antigen-binding fragment thereof; (b) a second anti-MERS-CoV-S antibody or antigen-binding fragment thereof, wherein the first antibody binds to a first epitope on MERS-CoV spike protein and the second antibody binds to a second epitope on MERS-CoV spike protein wherein the first and second epitopes are distinct and non-overlapping; and (c) a pharmaceutically acceptable carrier or diluent. In certain embodiments, the invention provides for a pharmaceutical composition comprising: (a) a first anti-MERS-CoV-S antibody or antigen-binding fragment thereof; (b) a second anti-MERS-CoV-S antibody or antigen-binding fragment thereof, wherein the first antibody does not cross-compete with the second antibody for binding to MERS-CoV spike protein; and (c) a pharmaceutically acceptable carrier or diluent. Additional combination therapies and co-formulations involving the anti-MERS-CoV-S antibodies of the present invention are disclosed elsewhere herein.

In a fourth aspect, the invention provides therapeutic methods for treating a disease or disorder associated with MERS-CoV such as viral infection in a subject using an anti-MERS-CoV-S antibody or antigen-binding portion of an antibody of the invention, wherein the therapeutic methods comprise administering a therapeutically effective amount of a pharmaceutical composition comprising an antibody or antigen-binding fragment of an antibody of the invention to the subject in need thereof. The disorder treated is any disease or condition which is improved, ameliorated, inhibited or prevented by inhibition of MERS-CoV activity. In certain embodiments, the invention provides methods to prevent, treat or ameliorate at least one symptom of MERS-CoV infection, the method comprising administering a therapeutically effective amount of an anti-MERS-CoV-S antibody or antigen-binding fragment thereof of the invention to a subject in need thereof. In some embodiments, the present invention provides methods to ameliorate or reduce the severity of at least one symptom or indication of MERS infection in a subject by administering an anti-MERS-CoV-S antibody of the invention, wherein the at least one symptom or indication is selected from the group consisting of inflammation in the lung, alveolar damage, fever, cough, shortness of breath, diarrhea, organ failure, pneumonia, septic shock and death. In certain embodiments, the invention provides methods to decrease viral load in a subject, the methods comprising administering to the subject an effective amount of an antibody or fragment thereof of the invention that binds MERS-CoV-S and blocks MERS-CoV-S binding to host cell receptor DPP4. In some embodiments, the antibody or antigen-binding fragment thereof may be administered prophylactically or therapeutically to a subject having or at risk of having MERS infection. The subjects at risk include, but are not limited to, an immunocompromised person, an elderly adult (more than 65 years of age), children younger than 2 years of age, travelers to countries in the Middle East (such as Saudi Arabia, United Arab Emirates, Qatar, etc.), healthcare workers, adults or children in close contact with a person(s) with confirmed or suspected MERS infection, and people with underlying medical conditions such as pulmonary infection, heart disease or diabetes. In certain embodiments, the antibody or antigen-binding fragment thereof the invention is administered in combination with a second therapeutic agent to the subject in need thereof. The second therapeutic agent may be selected from the group consisting of an anti-inflammatory drug (such as corticosteroids, and non-steroidal anti-inflammatory drugs), an anti-infective drug, a different antibody to MERS-CoV spike protein, an anti-viral drug, a vaccine for MERS-CoV, a dietary supplement such as anti-oxidants and any other drug or therapy known in the art. In certain embodiments, the second therapeutic agent may be an agent that helps to counteract or reduce any possible side effect(s) associated with an antibody or antigen-binding fragment thereof of the invention, if such side effect(s) should occur. The antibody or fragment thereof may be administered subcutaneously, intravenously, intradermally, intraperitoneally, orally, intramuscularly, or intracranially. In one embodiment, the antibody may be administered as a single intravenous infusion for maximum concentration of the antibody in the serum of the subject. The antibody or fragment thereof may be administered at a dose of about 0.1 mg/kg of body weight to about 100 mg/kg of body weight of the subject. In certain embodiments, an antibody of the present invention may be administered at one or more doses comprising between 50 mg to 600 mg.

The present invention also includes use of an anti-MERS-CoV-S antibody or antigen-binding fragment thereof of the invention in the manufacture of a medicament for the treatment of a disease or disorder that would benefit from the blockade of MERS-CoV binding and/or activity.

Other embodiments will become apparent from a review of the ensuing detailed description.

BRIEF DESCRIPTION OF THE FIGURES

FIG. 1 is a table listing antibody hybridoma supernatants (listed in column 1 by their Sample ID) and their properties in binding, blocking and neutralization assays, as described elsewhere herein.

FIG. 2 is a matrix showing the results of an antibody cross-competition assay in which a first anti-MERS-CoV-S antibody (mAb-1) was applied to a MERS RBD-coated sensor tip, followed by treatment with a second anti-MERS-CoV-S antibody (mAb-2). Binding responses (numerical values −0.05 to 0.64) for each antibody combination tested are depicted. Light grey boxes with black font represent binding response for self-competition. Antibodies competing in both directions, independent of the order of antigen binding, are highlighted in black boxes with white font. No competition, suggesting distinct binding regions, is represented as white boxes with black font. Antibodies that show more than 0.18 nm shift in binding do not cross-compete with one another.

FIG. 3 is a matrix showing the results of an antibody cross-competition assay in which a first anti-MERS-CoV-S antibody (mAb-1) was applied to a MERS RBD-coated sensor tip, followed by treatment with a second anti-MERS-CoV-S antibody (mAb-2). Binding responses (numerical values −0.01 to 0.55) for each antibody combination tested are depicted. Light grey boxes with black font represent binding response for self-competition. Antibodies competing in both directions, independent of the order of antigen binding, are highlighted in black boxes with white font. No competition, suggesting distinct binding regions, is represented as white boxes with black font. Antibodies that show more than 0.14 nm shift in binding do not cross-compete with one another.

DETAILED DESCRIPTION

Figure 4:
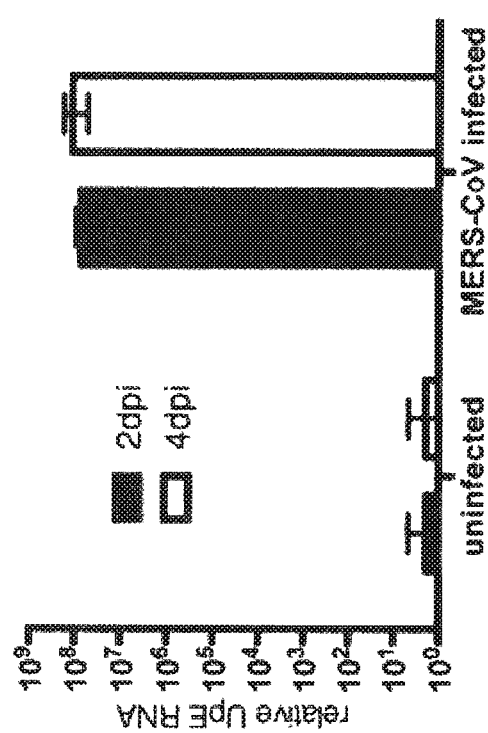
FIG. 4 shows quantitative PCR of MERS-CoV transcript (transcribed mRNA of the genome upstream of the envelope gene—UpE) in humanized DPP4 mice at days 2 and 4 post infection.

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, preferred methods and materials are now described. All publications mentioned herein are incorporated herein by reference in their entirety.

Definitions

The term "MERS-CoV", also called as "MERS coronavirus", refers to the newly-emerged Middle East Respiratory Syndrome-Corona Virus which was first isolated in the Arabian peninsula in 2012 (Zaki et al 2012, NEJM 367: 1814-1820) and identified as the cause for the outbreak of severe acute respiratory disease. It was initially called human coronavirus-EMC (Erasmus Medical Centre; hCoV-EMC). It belongs to the betacoronavirus lineage 2c and causes severe respiratory disease, similar to the Severe Acute Respiratory Syndrome coronavirus (SARS-CoV) that emerged in China in 2002. The MERS coronavirus has been found to be closely related to coronaviruses found in bats and camels. It binds via the viral spike protein to human host cell receptor dipeptidyl peptidase 4 (DPP4). MERS-CoV spike protein has been found to bind to DPP4 of other species, especially bats and camels (Raj et al 2013, Nature 495: 251-254).

The term "MERS-CoV-S", also called "S protein" refers to the spike protein of the MERS coronavirus. The MERS-CoV spike protein is a 1353 amino acid type I membrane glycoprotein which assembles into trimers that constitute the spikes or peplomers on the surface of the enveloped MERS coronavirus particle. The protein has two essential functions, host receptor binding and membrane fusion, which are attributed to the N-terminal (S1, amino acid residues 1-751) and C-terminal (S2, amino acid residues 752-1353) halves of the S protein. MERS-CoV-S binds to its cognate receptor, dipeptidyl peptidase 4 (DPP4) via about 230-amino acid long receptor binding domain (RBD) present in the S1 subunit. Mou et al (2013) have shown in J. Virology (vol 87, pages 9379-9383) that the MERS-CoV RBD is located within the residues 358-588 of the spike protein. The amino acid sequence of full-length MERS-CoV spike protein is exemplified by the amino acid sequence of spike protein of MERS-CoV isolate EMC/2012 provided in GenBank as accession number AFS88936.1 (SEQ ID NO: 457). The term "MERS-CoV-S" also includes protein variants of MERS-CoV spike protein isolated from different MERS-CoV isolates, e.g., Jordan-N3/2012, England-Qatar/2012, Al-Hasa_1_2013, Al-Hasa_2_2013, Al-Hasa_3_2013, Al-Hasa_4_2013, Al-Hasa_12, Al-Hasa_15, Al-Hasa_16, Al-Hasa_17, Al-Hasa_18, Al-Hasa_19, Al-Hasa_21, Al-Hasa_25, Bisha_1, Buraidah_1, England 1, Hafr-Al-Batin_1, Hafr-Al-Batin_2, Hafr-Al-Batin_6, Jeddah_1, KFU-HKU 1, KFU-HKU 13, Munich, Qatar3, Qatar4, Riyadh_1, Riyadh_2, Riyadh_3, Riyadh_3, Riyadh_4, Riyadh_5, Riyadh_9, Riyadh_14, Taif_1, UAE, and Wadi-Ad-Dawasir. The term "MERS-CoV-S" includes recombinant MERS-CoV spike protein or a fragment thereof. The term also encompasses MERS-CoV spike protein or a fragment thereof coupled to, for example, histidine tag, mouse or human Fc, or a signal sequence such as ROR1. For example, the term includes sequences exemplified by the sequence shown in SEQ ID NO: 458, comprising a mouse Fc (mIgG2a) or human Fc (hIgG1) at the C-terminal, coupled to amino acid residues 367-606 of full-length MERS-CoV spike protein. The term also includes protein variants that comprise a histidine tag at the C-terminal, coupled to amino acid residues 367-606 of full-length MERS-CoV spike protein.

The term "DPP4" refers to dipeptidyl peptidase 4, a receptor for MERS-CoV. DPP4 is a 766-amino acid type II transmembrane glycoprotein present in a dimeric form on the cell surface. It is an exopeptidase that cleaves dipeptides from hormones and chemokines after a proline amino acid residue, thereby regulating their bioactivity. In humans, DPP4 is primarily expressed on the epithelial cells in kidney, small intestine, liver and prostate, on ciliated and non-ciliated cells in the upper and lower respiratory tract, and on immune cells (i.e., CD4+, CD8+, dendritic cells and macrophages). Unless specified as being from a non-human species, the term "DPP4", as used herein, means human DPP4.

The term "MERS infection" or "MERS-CoV infection", as used herein, also characterized as Middle East Respiratory Syndrome refers to the severe acute respiratory illness caused by MERS coronavirus and first reported in Saudi Arabia in 2012. The term includes respiratory tract infection, often in the lower respiratory tract. The symptoms include high fever, cough, shortness of breath pneumonia, gastrointestinal symptoms such as diarrhea, organ failure (kidney failure and renal dysfunction), septic shock and death in severe cases.

The term "antibody", as used herein, is intended to refer to immunoglobulin molecules comprised of four polypeptide chains, two heavy (H) chains and two light (L) chains inter-connected by disulfide bonds (i.e., "full antibody molecules"), as well as multimers thereof (e.g. IgM) or antigen-binding fragments thereof. Each heavy chain is comprised of a heavy chain variable region ("HCVR" or "$V_H$") and a heavy chain constant region (comprised of domains $C_H1$, $C_H2$ and $C_H3$). Each light chain is comprised of a light chain variable region ("LCVR or "$V_L$") and a light chain constant region ($C_L$). The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In certain embodiments of the invention, the FRs of the antibody (or antigen binding fragment thereof) may be identical to the human germline sequences, or may be naturally or artificially modified. An amino acid consensus sequence may be defined based on a side-by-side analysis of two or more CDRs.

Substitution of one or more CDR residues or omission of one or more CDRs is also possible. Antibodies have been described in the scientific literature in which one or two CDRs can be dispensed with for binding. Padlan et al. (1995 FASEB J. 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos et al. 2002 J Mol Biol 320:415-428).

CDR residues not contacting antigen can be identified based on previous studies (for example residues H60-H65 in CDRH2 are often not required), from regions of Kabat CDRs lying outside Chothia CDRs, by molecular modeling and/or empirically. If a CDR or residue(s) thereof is omitted, it is usually substituted with an amino acid occupying the corresponding position in another human antibody sequence or a consensus of such sequences. Positions for substitution within CDRs and amino acids to substitute can also be selected empirically. Empirical substitutions can be conservative or non-conservative substitutions.

The fully human anti-MERS-CoV-S monoclonal antibodies disclosed herein may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes fully human anti-MERS-CoV-S monoclonal antibodies comprising variants of any of the HCVR, LCVR, and/or CDR amino acid sequences disclosed herein having one or more conservative substitutions. For example, the present invention includes anti-MERS-CoV antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "human antibody", as used herein, is intended to include antibodies having variable and constant regions derived from human germline immunoglobulin sequences. The human mAbs of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse), have been grafted onto human FR sequences. The term includes antibodies recombinantly produced in a non-human mammal, or in cells of a non-human mammal. The term is not intended to include antibodies isolated from or generated in a human subject.

The term "recombinant", as used herein, refers to antibodies or antigen-binding fragments thereof of the invention created, expressed, isolated or obtained by technologies or methods known in the art as recombinant DNA technology which include, e.g., DNA splicing and transgenic expression. The term refers to antibodies expressed in a non-human mammal (including transgenic non-human mammals, e.g., transgenic mice), or a cell (e.g., CHO cells) expression system or isolated from a recombinant combinatorial human antibody library.

The term "specifically binds," or "binds specifically to", or the like, means that an antibody or antigen-binding fragment thereof forms a complex with an antigen that is relatively stable under physiologic conditions. Specific binding can be characterized by an equilibrium dissociation constant of at least about $1\times10^{-8}$ M or less (e.g., a smaller $K_D$ denotes a tighter binding). Methods for determining whether two molecules specifically bind are well known in the art and include, for example, equilibrium dialysis, surface plasmon resonance, and the like. As described herein, antibodies have been identified by surface plasmon resonance, e.g., BIACORE™, which bind specifically to MERS-CoV-S. Moreover, multi-specific antibodies that bind to one domain in MERS-CoV-S and one or more additional antigens or a bi-specific that binds to two different regions of MERS-CoV-S are nonetheless considered antibodies that "specifically bind", as used herein.

The term "high affinity" antibody refers to those mAbs having a binding affinity to MERS-CoV-S, expressed as $K_D$, of at least $10^{-8}$ M; preferably $10^{-9}$ M; more preferably $10^{-10}$M, even more preferably $10^{-11}$ M, even more preferably $10^{-12}$ M, as measured by surface plasmon resonance, e.g., BIACORE™ or solution-affinity ELISA.

By the term "slow off rate", "Koff" or "kd" is meant an antibody that dissociates from MERS-CoV, with a rate constant of $1 \times 10^{-3}$ $s^{-1}$ or less, preferably $1 \times 10^{-4}$ $s^{-1}$ or less, as determined by surface plasmon resonance, e.g., BIA-CORE™.

The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to bind to MERS-CoV spike protein.

In specific embodiments, antibody or antibody fragments of the invention may be conjugated to a moiety such a ligand or a therapeutic moiety ("immunoconjugate"), such as an anti-viral drug, a second anti-MERS-CoV-S antibody, or any other therapeutic moiety useful for treating an infection caused by MERS-CoV.

An "isolated antibody", as used herein, is intended to refer to an antibody that is substantially free of other antibodies (Abs) having different antigenic specificities (e.g., an isolated antibody that specifically binds MERS-CoV-S, or a fragment thereof, is substantially free of Abs that specifically bind antigens other than MERS-CoV-S.

A "blocking antibody" or a "neutralizing antibody", as used herein (or an "antibody that neutralizes MERS-CoV-S activity" or "antagonist antibody"), is intended to refer to an antibody whose binding to MERS-CoV-S results in inhibition of at least one biological activity of MERS-CoV. For example, an antibody of the invention may prevent or block MERS-CoV binding to DPP4.

The term "surface plasmon resonance", as used herein, refers to an optical phenomenon that allows for the analysis of real-time biomolecular interactions by detection of alterations in protein concentrations within a biosensor matrix, for example using the BIACORE™ system (Pharmacia Biosensor AB, Uppsala, Sweden and Piscataway, N.J.).

The term "$K_D$", as used herein, is intended to refer to the equilibrium dissociation constant of a particular antibody-antigen interaction.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. The term "epitope" also refers to a site on an antigen to which B and/or T cells respond. It also refers to a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

The term "cross-competes", as used herein, means an antibody or antigen-binding fragment thereof binds to an antigen and inhibits or blocks the binding of another antibody or antigen-binding fragment thereof. The term also includes competition between two antibodies in both orientations, i.e., a first antibody that binds and blocks binding of second antibody and vice-versa. In certain embodiments, the first antibody and second antibody may bind to the same epitope. Alternatively, the first and second antibodies may bind to different, but overlapping epitopes such that binding of one inhibits or blocks the binding of the second antibody, e.g., via steric hindrance. Cross-competition between antibodies may be measured by methods known in the art, for example, by a real-time, label-free bio-layer interferometry assay. Cross-competition between two antibodies may be expressed as the binding of the second antibody that is less than the background signal due to self-self binding (wherein first and second antibodies is the same antibody). Cross-competition between 2 antibodies may be expressed, for example, as % binding of the second antibody that is less than the baseline self-self background binding (wherein first and second antibodies is the same antibody).

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% of the nucleotide bases, as measured by any well-known algorithm of sequence identity, such as FASTA, BLAST or GAP, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 90% sequence identity, even more preferably at least 95%, 98% or 99% sequence identity. Preferably, residue positions, which are not identical, differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) Methods Mol. Biol. 24: 307-331, which is herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443 45, herein incorporated by reference. A "moderately conservative"

replacement is any change having a nonnegative value in the PAM250 log-likelihood matrix.

Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215: 403-410 and (1997) Nucleic Acids Res. 25:3389-3402, each of which is herein incorporated by reference.

By the phrase "therapeutically effective amount" is meant an amount that produces the desired effect for which it is administered. The exact amount will depend on the purpose of the treatment, and will be ascertainable by one skilled in the art using known techniques (see, for example, Lloyd (1999) The Art, Science and Technology of Pharmaceutical Compounding).

As used herein, the term "subject" refers to an animal, preferably a mammal, more preferably a human, in need of amelioration, prevention and/or treatment of a disease or disorder such as viral infection. The term includes human subjects who have or are at risk of having MERS infection.

As used herein, the terms "treat", "treating", or "treatment" refer to the reduction or amelioration of the severity of at least one symptom or indication of MERS infection due to the administration of a therapeutic agent such as an antibody of the present invention to a subject in need thereof. The terms include inhibition of progression of disease or of worsening of infection. The terms also include positive prognosis of disease, i.e., the subject may be free of infection or may have reduced or no viral titers upon administration of a therapeutic agent such as an antibody of the present invention. The therapeutic agent may be administered at a therapeutic dose to the subject.

The terms "prevent", "preventing" or "prevention" refer to inhibition of manifestation of MERS infection or any symptoms or indications of MERS infection upon administration of an antibody of the present invention. The term includes prevention of spread of infection in a subject exposed to the virus or at risk of having MERS infection.

As used herein, the term "anti-viral drug" refers to any anti-infective drug or therapy used to treat, prevent, or ameliorate a viral infection in a subject. The term "anti-viral drug" includes, but is not limited to ribavirin, oseltamivir, zanamivir, interferon-alpha2b, analgesics and corticosteroids. In the context of the present invention, the viral infections include infection caused by human coronaviruses, including but not limited to, MERS-CoV, HCoV_229E, HCoV_NL63, HCoV-OC43, HCoV_HKU1, and SARS-CoV.

General Description

Passive immunotherapy for prophylaxis or treatment of infectious diseases has been used for more than a century, usually in the form of convalescent human sera that contains high titers of neutralizing antibodies (Good et al 1991; Cancer 68: 1415-1421). Today, multiple purified monoclonal antibodies are currently in preclinical and clinical development for use as anti-microbials (Marasco et al 2007; Nature Biotechnology 25: 1421-1434).

The inventors have described herein fully human antibodies and antigen-binding fragments thereof that specifically bind to MERS-CoV-S and modulate the interaction of MERS-CoV-S with DPP4. The anti-MERS-CoV-S antibodies may bind to MERS-CoV-S with high affinity. In certain embodiments, the antibodies of the present invention are blocking antibodies wherein the antibodies may bind to MERS-CoV-S and block the interaction of MERS-CoV-S with DPP4. In some embodiments, the blocking antibodies of the invention may block the binding of MERS-CoV-S to DPP4 and/or inhibit or neutralize viral infectivity of host cells. In some embodiments, the blocking antibodies may be useful for treating a subject suffering from MERS infection. In certain embodiments, selected antibodies that do not cross-compete for binding to the spike protein are used in combination as a cocktail to reduce the ability of the virus to escape via mutation in response to the selective pressure from either component. The antibodies when administered to a subject in need thereof may reduce the infection by a virus such as MERS-CoV in the subject. They may be used to decrease viral loads in a subject. They may be used alone or as adjunct therapy with other therapeutic moieties or modalities known in the art for treating viral infection. It is also shown herein that these antibodies bind to epitopes on the S protein that have been conserved during the natural evolution of the virus during the past two years. Further, a novel transgenic mouse model was used to demonstrate that the identified antibodies can prophylactically protect mice from infection as well as ameliorate a previously established infection in a post-inoculation treatment paradigm. In Example 7, it is shown that administration of an anti-MERS-Cov-S antibody at 1 day before infection is able to reduce MERS-CoV replication to near the level of detection in the live virus assays and by 3 logs in the viral RNA assays. This antibody demonstrated dose-dependent protection, as lower doses of the antibody given 24 hours pre-infection were able to block MERS-CoV to a lesser degree. Additionally, histological analysis of lung tissue demonstrated that mice pre-treated with the antibody displayed reduced MERS-CoV induced peri-bronchiolar cuffing, alveolar wall thickening, and overall inflammatory foci.

The full-length amino acid sequence of full length MERS-CoV spike protein is shown in SEQ ID NO: 457. In certain embodiments, the antibodies of the invention are obtained from mice immunized with a primary immunogen, such as a full length MERS-CoV spike protein (SEQ ID NO: 457) or with a recombinant form of MERS-CoV-S or modified MERS-CoV-S fragments (e.g., SEQ ID NO: 458), followed by immunization with a secondary immunogen, or with an immunogenically active fragment of MERS-CoV-S.

The immunogen may be a biologically active and/or immunogenic fragment of MERS-CoV-S or DNA encoding the active fragment thereof. The fragment may be derived from the N-terminal or C-terminal domain of MERS-CoV-S. In certain embodiments of the invention, the immunogen is a fragment of MERS-CoV-S that ranges from amino acid residues 367-606 of SEQ ID NO: 457.

The peptides may be modified to include addition or substitution of certain residues for tagging or for purposes of conjugation to carrier molecules, such as, KLH. For example, a cysteine may be added at either the N terminal or C terminal end of a peptide, or a linker sequence may be added to prepare the peptide for conjugation to, for example, KLH for immunization.

Certain anti-MERS-CoV-S antibodies of the present invention are able to bind to and neutralize the activity of MERS-CoV-S, as determined by in vitro or in vivo assays. The ability of the antibodies of the invention to bind to and neutralize the activity of MERS-CoV-S may be measured using any standard method known to those skilled in the art, including binding assays, or activity assays, as described herein.

Non-limiting, exemplary in vitro assays for measuring binding and blocking activity are illustrated in Examples 4-5, herein. In Example 4, the binding affinity and dissociation constants of anti-MERS-CoV-S antibodies for MERS-CoV-S were determined by surface plasmon resonance assay. In Example 5, neutralization assays were used to determine infectivity of MERS-CoV spike protein-containing virus-like particles.

The antibodies specific for MERS-CoV-S may contain no additional labels or moieties, or they may contain an N-terminal or C-terminal label or moiety. In one embodiment, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface. In one embodiment, the label may be a radionuclide, a fluorescent dye or a MRI-detectable label. In certain embodiments, such labeled antibodies may be used in diagnostic assays including imaging assays.

Antigen-Binding Fragments of Antibodies

Unless specifically indicated otherwise, the term "antibody," as used herein, shall be understood to encompass antibody molecules comprising two immunoglobulin heavy chains and two immunoglobulin light chains (i.e., "full antibody molecules") as well as antigen-binding fragments thereof. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to specifically bind to MERS-CoV spike protein. An antibody fragment may include a Fab fragment, a F(ab')$_2$ fragment, a Fv fragment, a dAb fragment, a fragment containing a CDR, or an isolated CDR. In certain embodiments, the term "antigen-binding fragment" refers to a polypeptide fragment of a multi-specific antigen-binding molecule. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and (optionally) constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-VH, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H$1; (ii) $V_H$-$C_H$2; (iii) $V_H$-$C_H$3; (iv) $V_H$-$C_H$1-$C_H$2; (v) $V_H$-$C_H$1-$C_H$2-$C_H$3; (vi) $V_H$-$C_H$2-$C_H$3; (vii) $V_H$-$C_L$; (viii) $V_L$-$C_H$1; (ix) $V_L$-$C_H$2; (x) $V_L$-$C_H$3; (xi) $V_L$-$C_H$1-$C_H$2; (xii) $V_L$-$C_H$1-$C_H$2-$C_H$3; (xiii) $V_L$-$C_H$2-$C_H$3; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be mono-specific or multi-specific (e.g., bi-specific). A multi-specific antigen-binding fragment of an antibody will typically comprise at least two different variable domains, wherein each variable domain is capable of specifically binding to a separate antigen or to a different epitope on the same antigen. Any multi-specific antibody format, including the exemplary bi-specific antibody formats disclosed herein, may be adapted for use in the context of an antigen-binding fragment of an antibody of the present invention using routine techniques available in the art.

Preparation of Human Antibodies

Methods for generating human antibodies in transgenic mice are known in the art. Any such known methods can be used in the context of the present invention to make human antibodies that specifically bind to MERS-CoV spike protein.

An immunogen comprising any one of the following can be used to generate antibodies to MERS-CoV spike protein. In certain embodiments, the antibodies of the invention are obtained from mice immunized with a full length, native MERS-CoV spike protein (See, for example, GenBank accession number AFS88936.1) (SEQ ID NO: 457), or with DNA encoding the protein or fragment thereof. Alternatively, the spike protein or a fragment thereof may be produced using standard biochemical techniques and modified and used as immunogen. In one embodiment, the immunogen is the receptor binding domain (S1) of MERS-CoV spike protein. In certain embodiments of the invention, the immunogen is a fragment of MERS-CoV spike protein that ranges from about amino acid residues 367-606 of SEQ ID NO: 457.

In some embodiments, the immunogen may be a recombinant MERS-CoV spike protein receptor binding domain peptide expressed in E. coli or in any other eukaryotic or mammalian cells such as Chinese hamster ovary (CHO) cells.

Using VELOCIMMUNE® technology (see, for example, U.S. Pat. No. 6,596,541, Regeneron Pharmaceuticals, VELOCIMMUNE®) or any other known method for generating monoclonal antibodies, high affinity chimeric antibodies to MERS-CoV-S are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

Initially, high affinity chimeric antibodies are isolated having a human variable region and a mouse constant region. As in the experimental section below, the antibodies are characterized and selected for desirable characteristics, including affinity, selectivity, epitope, etc. The mouse constant regions are replaced with a desired human constant region to generate the fully human antibody of the invention, for example wild-type or modified IgG1 or IgG4. While the constant region selected may vary according to specific use, high affinity antigen-binding and target specificity characteristics reside in the variable region.

Bioequivalents

The anti-MERS-CoV-S antibodies and antibody fragments of the present invention encompass proteins having amino acid sequences that vary from those of the described antibodies, but that retain the ability to bind MERS-CoV spike protein. Such variant antibodies and antibody fragments comprise one or more additions, deletions, or substitutions of amino acids when compared to parent sequence, but exhibit biological activity that is essentially equivalent to that of the described antibodies. Likewise, the antibody-encoding DNA sequences of the present invention encompass sequences that comprise one or more additions, deletions, or substitutions of nucleotides when compared to the disclosed sequence, but that encode an antibody or antibody fragment that is essentially bioequivalent to an antibody or antibody fragment of the invention.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single dose or multiple doses. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, or potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and/or in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of the antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include antibody variants comprising amino acid changes, which modify the glycosylation characteristics of the antibodies, e.g., mutations that eliminate or remove glycosylation.

Anti-MERS-CoV-S Antibodies Comprising Fc Variants

According to certain embodiments of the present invention, anti-MERS-CoV-S antibodies are provided comprising an Fc domain comprising one or more mutations which enhance or diminish antibody binding to the FcRn receptor, e.g., at acidic pH as compared to neutral pH. For example, the present invention includes anti-MERS-CoV-S antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., A, W, H, F or Y [N434A, N434W, N434H, N434F or N434Y]); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P). In yet another embodiment, the modification comprises a 265A (e.g., D265A) and/or a 297A (e.g., N297A) modification.

For example, the present invention includes anti-MERS-CoV-S antibodies comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); 257I and 311I (e.g., P257I and Q311I); 257I and 434H (e.g., P257I and N434H); 376V and 434H (e.g., D376V and N434H); 307A, 380A and 434A (e.g., T307A, E380A and N434A); and 433K and 434F (e.g., H433K and N434F). All possible combinations of the foregoing Fc domain mutations and other mutations within the antibody variable domains disclosed herein, are contemplated within the scope of the present invention.

The present invention also includes anti-MERS-CoV-S antibodies comprising a chimeric heavy chain constant ($C_H$) region, wherein the chimeric $C_H$ region comprises segments derived from the $C_H$ regions of more than one immunoglobulin isotype. For example, the antibodies of the invention may comprise a chimeric $C_H$ region comprising part or all of a $C_H2$ domain derived from a human IgG1, human IgG2 or human IgG4 molecule, combined with part or all of a $C_H3$ domain derived from a human IgG1, human IgG2 or human IgG4 molecule. According to certain embodiments, the antibodies of the invention comprise a chimeric $C_H$ region having a chimeric hinge region. For example, a chimeric hinge may comprise an "upper hinge" amino acid sequence (amino acid residues from positions 216 to 227 according to EU numbering) derived from a human IgG1, a human IgG2 or a human IgG4 hinge region, combined with a "lower hinge" sequence (amino acid residues from positions 228 to 236 according to EU numbering) derived from a human IgG1, a human IgG2 or a human IgG4 hinge region. According to certain embodiments, the chimeric hinge region comprises amino acid residues derived from a human IgG1 or a human IgG4 upper hinge and amino acid residues derived from a human IgG2 lower hinge. An antibody comprising a chimeric $C_H$ region as described herein may, in certain embodiments, exhibit modified Fc effector functions without adversely affecting the therapeutic or pharmacokinetic properties of the antibody. (See, e.g., U.S. Provisional Appl. No. 61/759,578, filed Feb. 1, 2013, the disclosure of which is hereby incorporated by reference in its entirety).

Biological Characteristics of the Antibodies

In general, the antibodies of the present invention function by binding to MERS-CoV spike protein. In certain embodiments, the antibodies of the present invention bind with high affinity to one or more amino acids in the receptor binding domain (RBD) of the spike protein of MERS-CoV. For example, the present invention includes antibodies and antigen-binding fragments of antibodies that bind dimeric MERS-CoV spike protein RBD (e.g., at 25° C. or at 37° C.) with a $K_D$ of less than 20 nM as measured by surface plasmon resonance, e.g., using the assay format as defined in Example 4 herein. In certain embodiments, the antibodies or antigen-binding fragments thereof bind dimeric MERS-CoV-S with a $K_D$ of less than about 20 nM, less than about 10 nM, less than about 5 nM, less than about 2 nM, less than about 1 nM, less than about 500 pM, less than 250 pM, or less than 100 pM, as measured by surface plasmon resonance, e.g., using the assay format as defined in Example 4 herein, or a substantially similar assay.

The present invention also includes antibodies and antigen-binding fragments thereof that bind MERS-CoV spike protein with a dissociative half-life (t½) of greater than about 2.1 minutes as measured by surface plasmon resonance at 25° C., e.g., using an assay format as defined in Example 4 herein, or a substantially similar assay. In certain embodiments, the antibodies or antigen-binding fragments of the present invention bind MERS-CoV spike protein with a t½ of greater than about 5 minutes, greater than about 10 minutes, greater than about 30 minutes, greater than about 50 minutes, greater than about 100 minutes, greater than about 150 minutes, greater than about 200 minutes, or greater than about 250 minutes, as measured by surface plasmon resonance at 25° C., e.g., using an assay format as defined in Example 4 herein (e.g., mAb-capture or antigen-capture format), or a substantially similar assay.

The present invention also includes antibodies and antigen-binding fragments thereof that bind MERS-CoV spike protein with a dissociative half-life (t½) of greater than about 1.5 minutes as measured by surface plasmon resonance at 37° C., e.g., using an assay format as defined in Example 4 herein, or a substantially similar assay. In certain embodiments, the antibodies or antigen-binding fragments of the present invention bind MERS-CoV spike protein with a t½ of greater than about 2 minutes, greater than about 5 minutes, greater than about 10 minutes, greater than about 25 minutes, greater than about 50 minutes, greater than about 100 minutes, greater than about 150 minutes, or greater than about 200 minutes, as measured by surface plasmon resonance at 37° C., e.g., using an assay format as defined in Example 4 herein (e.g., mAb-capture or antigen-capture format), or a substantially similar assay.

The present invention also includes antibodies or antigen-binding fragments thereof that block more than 90% MERS-CoV-S binding to DPP4 as determined using a ELISA-based immunoassay assay, e.g., as shown in Example 2, or a substantially similar assay.

The present invention also includes antibodies or antigen-binding fragments thereof that neutralize or inhibit the infectivity of MERS-CoV for its host cells. In certain embodiments, the antibodies neutralize the infectivity of MERS-CoV-like pseudoparticles (MERSpp). In some embodiments, the antibodies inhibited more than 90% binding of MERS-CoV on human host cells in an optimized virus-like pseudo-particle (VLP) neutralization assay, e.g., as shown in Example 5, or a substantially similar assay. The antibodies neutralized the MERSpp infectivity with IC50 ranging from 58.9 pM to 2.93 nM.

In some embodiments, the antibodies of the present invention bind to the receptor binding domain of MERS-CoV spike protein or to a fragment of the domain. In some embodiments, the antibodies of the present invention may bind to more than one domain (cross-reactive antibodies). In certain embodiments, the antibodies of the present invention may bind to an epitope located in the receptor binding domain comprising amino acid residues 367-606 of MERS-CoV-S. In one embodiment, the antibodies may bind to an epitope comprising one or more amino acids selected from the group consisting of amino acid residues 367-606 of the sequence set forth in SEQ ID NO: 457.

In certain embodiments, the antibodies of the present invention may function by blocking or inhibiting the DPP4-binding activity associated with MERS-CoV spike protein by binding to any other region or fragment of the full length protein, the amino acid sequence of which is set forth in SEQ ID NO: 457.

In certain embodiments, the antibodies of the present invention may be bi-specific antibodies. The bi-specific antibodies of the invention may bind one epitope in one domain and may also bind a second epitope in the same or a different domain of MERS-CoV spike protein. In certain embodiments, the bi-specific antibodies of the invention may bind two different epitopes in the same domain.

In one embodiment, the invention provides an isolated recombinant antibody or antigen-binding fragment thereof that binds specifically to MERS-CoV spike protein, wherein the antibody or fragment thereof exhibits one or more of the following characteristics: (a) is a fully human monoclonal antibody; (b) interacts with one or more amino acid residues in the receptor binding domain of the spike protein selected from amino acid residues 367 to 606 of the sequence shown in SEQ ID NO: 457; (c) binds to MERS-CoV spike protein with a dissociation constant ($K_D$) of less than 18.5 nM, as measured in a surface plasmon resonance assay; (d) blocks binding of MERS-CoV spike protein to dipeptidyl peptidase 4 by more than 90%, as measured in a blocking ELISA assay; (e) neutralizes MERS-CoV infectivity of human host cells by more than 90% and with an $IC_{50}$ less than 4 nM, as measured in a VLP neutralization assay; (f) neutralizes MERS-CoV infectivity wherein the MERS-CoV comprises an isolate of the virus selected from the group consisting of EMC/2012, Jordan-N3/2012, England-Qatar/2012, Al-Hasa_1_2013, Al-Hasa_2_2013, Al-Hasa_3_2013, Al-Hasa_4_2013, Al-Hasa_12, Al-Hasa_15, Al-Hasa_16, Al-Hasa_17, Al-Hasa_18, Al-Hasa_19, Al-Hasa_21, Al-hasa_25, Bisha_1, Buraidah_1, England 1, Hafr-Al-batin_1, Hafr-Al-Batin_2, Hafr-Al-Batin_6, Jeddah_1, KFU-HKU 1, KFU-HKU 13, Munich, Qatar3, Qatar4, Riyadh_1, Riyadh_2, Riyadh_3, Riyadh_3, Riyadh_4, Riyadh_5, Riyadh_9, Riyadh_14, Taif_1, UAE, and Wadi-Ad-Dawasir; (g) blocks MERS-CoV replication in vivo in a subject infected with MERS-CoV; and (h) is a bi-specific antibody comprising a first binding specificity to a first epitope in the receptor binding domain of MERS-CoV spike protein and a second binding specificity to a second epitope in the receptor binding domain of MERS-CoV spike protein wherein the first and second epitopes are distinct and non-overlapping.

The antibodies of the present invention may possess one or more of the aforementioned biological characteristics, or any combinations thereof. Other biological characteristics of the antibodies of the present invention will be evident to a person of ordinary skill in the art from a review of the present disclosure including the working Examples herein.

Epitope Mapping and Related Technologies

The present invention includes anti-MERS-CoV-S antibodies which interact with one or more amino acids found within one or more domains of the MERS-CoV spike protein molecule including, the N-terminal S1 domain (amino acid residues 1-751) and C-terminal S2 domain (amino acid residues 752-1353). The epitope to which the antibodies bind may consist of a single contiguous sequence of 3 or more (e.g., 3, 4, 5, 6, 7, 8, 9, 10, 11, 12, 13, 14, 15, 16, 17, 18, 19, 20 or more) amino acids located within any of the aforementioned domains of the MERS-CoV spike protein molecule (e.g. a linear epitope in a domain). Alternatively, the epitope may consist of a plurality of non-contiguous amino acids (or amino acid sequences) located within either or both of the aforementioned domains of the spike protein molecule (e.g. a conformational epitope).

Various techniques known to persons of ordinary skill in the art can be used to determine whether an antibody "interacts with one or more amino acids" within a polypeptide or protein. Exemplary techniques include, for example, routine cross-blocking assays, such as that described in Antibodies, Harlow and Lane (Cold Spring Harbor Press, Cold Spring Harbor, N.Y.). Other methods include alanine scanning mutational analysis, peptide blot analysis (Reineke (2004) Methods Mol. Biol. 248: 443-63), peptide cleavage analysis crystallographic studies and NMR analysis. In addition, methods such as epitope excision, epitope extraction and chemical modification of antigens can be employed (Tomer (2000) Prot. Sci. 9: 487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antibody interface may retain deuterium and therefore exhibit relatively higher mass compared to amino acids not included in the interface. After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) Analytical Biochemistry 267: 252-259; Engen and Smith (2001) Anal. Chem. 73: 256A-265A.

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (see US 2004/0101920, herein specifically incorporated by reference in its entirety). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce mAbs having the desired characteristics. MAP may be used to sort the antibodies of the invention into groups of antibodies binding different epitopes.

In certain embodiments, the anti-MERS-CoV-S antibodies or antigen-binding fragments thereof bind an epitope within any one or more of the regions exemplified in MERS-CoV spike protein, either in natural form, as exemplified in SEQ ID NO: 457, or recombinantly produced, as exemplified in SEQ ID NO: 458, or to a fragment thereof. In some embodiments, the antibodies of the invention bind to an extracellular region comprising one or more amino acids selected from the group consisting of amino acid residues 367-606 of MERS-CoV spike protein.

In certain embodiments, the antibodies of the invention, interact with at least one amino acid sequence selected from the group consisting of amino acid residues ranging from about position 358 to about position 450; or amino acid residues ranging from about position 451 to about position 606 of SEQ ID NO: 457.

The present invention includes anti-MERS-CoV-S antibodies that bind to the same epitope, or a portion of the epitope, as any of the specific exemplary antibodies obtained from the cell lines listed in FIG. 1. Likewise, the present invention also includes anti-MERS-CoV-S antibodies that compete for binding to MERS-CoV spike protein or a fragment thereof with any of the specific exemplary antibodies obtained from the hybridomas listed in FIG. 1. For example, the present invention includes anti-MERS-CoV-S antibodies that cross-compete for binding to MERS-CoV spike protein with one or more antibodies obtained from the hybridomas listed in FIG. 1.

One can easily determine whether an antibody binds to the same epitope as, or competes for binding with, a reference anti-MERS-CoV-S antibody by using routine methods known in the art. For example, to determine if a test antibody binds to the same epitope as a reference anti-MERS-CoV-S antibody of the invention, the reference antibody is allowed to bind to a MERS-CoV spike protein or peptide under saturating conditions. Next, the ability of a test antibody to bind to the MERS-CoV spike protein molecule is assessed. If the test antibody is able to bind to MERS-CoV-S following saturation binding with the reference anti-MERS-CoV-S antibody, it can be concluded that the test antibody binds to a different epitope than the reference anti-MERS-CoV-S antibody. On the other hand, if the test antibody is not able to bind to the MERS-CoV spike protein following saturation binding with the reference anti-MERS-CoV-S antibody, then the test antibody may bind to the same epitope as the epitope bound by the reference anti-MERS-CoV-S antibody of the invention.

To determine if an antibody competes for binding with a reference anti-MERS-CoV-S antibody, the above-described binding methodology is performed in two orientations: In a first orientation, the reference antibody is allowed to bind to a MERS-CoV spike protein under saturating conditions followed by assessment of binding of the test antibody to the MERS-CoV-S molecule. In a second orientation, the test antibody is allowed to bind to a MERS-CoV-S molecule under saturating conditions followed by assessment of binding of the reference antibody to the MERS-CoV-S molecule. If, in both orientations, only the first (saturating) antibody is capable of binding to the MERS-CoV-S molecule, then it is concluded that the test antibody and the reference antibody compete for binding to MERS-CoV-S. As will be appreciated by a person of ordinary skill in the art, an antibody that competes for binding with a reference antibody may not necessarily bind to the identical epitope as the reference antibody, but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art.

Immunoconjugates

The invention encompasses a human anti-MERS-CoV-S monoclonal antibody conjugated to a therapeutic moiety ("immunoconjugate"), such as a toxoid or an anti-viral drug to treat MERS infection. As used herein, the term "immunoconjugate" refers to an antibody which is chemically or biologically linked to a radioactive agent, a cytokine, an interferon, a target or reporter moiety, an enzyme, a peptide or protein or a therapeutic agent. The antibody may be linked to the radioactive agent, cytokine, interferon, target or reporter moiety, enzyme, peptide or therapeutic agent at any location along the molecule so long as it is able to bind its target. Examples of immunoconjugates include antibody drug conjugates and antibody-toxin fusion proteins. In one embodiment, the agent may be a second different antibody to MERS-CoV spike protein. In certain embodiments, the antibody may be conjugated to an agent specific for a virally infected cell. The type of therapeutic moiety that may be conjugated to the anti-MERS-CoV-S antibody and will take into account the condition to be treated and the desired therapeutic effect to be achieved. Examples of suitable agents for forming immunoconjugates are known in the art; see for example, WO 05/103081.

Multi-Specific Antibodies

The antibodies of the present invention may be mono-specific, bi-specific, or multi-specific. Multi-specific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244.

Any of the multi-specific antigen-binding molecules of the invention, or variants thereof, may be constructed using standard molecular biological techniques (e.g., recombinant DNA and protein expression technology), as will be known to a person of ordinary skill in the art.

In some embodiments, MERS-CoV-S-specific antibodies are generated in a bi-specific format (a "bi-specific") in which variable regions binding to distinct domains of MERS-CoV spike protein are linked together to confer dual-domain specificity within a single binding molecule. Appropriately designed bi-specifics may enhance overall MERS-CoV-spike-protein inhibitory efficacy through increasing both specificity and binding avidity. Variable regions with specificity for individual domains, (e.g., segments of the N-terminal domain), or that can bind to different regions within one domain, are paired on a structural scaffold that allows each region to bind simultaneously to the separate epitopes, or to different regions within one domain. In one example for a bi-specific, heavy chain variable regions ($V_H$) from a binder with specificity for one domain are recombined with light chain variable regions ($V_L$) from a series of binders with specificity for a second domain to identify non-cognate $V_L$ partners that can be paired with an original $V_H$ without disrupting the original specificity for that $V_H$. In this way, a single $V_L$ segment (e.g., $V_L1$) can be combined with two different $V_H$ domains (e.g., $V_H1$ and $V_H2$) to generate a bi-specific comprised of two binding "arms" ($V_H1$-$V_L1$ and $V_H2$-$V_L1$). Use of a single $V_L$ segment reduces the complexity of the system and thereby simplifies and increases efficiency in cloning, expression, and purification processes used to generate the bi-specific (See, for example, U.S. Ser. No. 13/022,759 and US2010/0331527).

Alternatively, antibodies that bind more than one domains and a second target, such as, but not limited to, for example, a second different anti-MERS-CoV-S antibody, may be prepared in a bi-specific format using techniques described herein, or other techniques known to those skilled in the art. Antibody variable regions binding to distinct regions may be linked together with variable regions that bind to relevant sites on, for example, the extracellular domain of MERS-CoV-S, to confer dual-antigen specificity within a single binding molecule. Appropriately designed bi-specifics of this nature serve a dual function. Variable regions with specificity for the extracellular domain are combined with a variable region with specificity for outside the extracellular domain and are paired on a structural scaffold that allows each variable region to bind to the separate antigens.

An exemplary bi-specific antibody format that can be used in the context of the present invention involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bi-specific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present invention.

Other exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mab$^2$ bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., *J. Am. Chem. Soc.* [*Epub*: Dec. 4, 2012]).

Therapeutic Administration and Formulations

The invention provides therapeutic compositions comprising the anti-MERS-CoV-S antibodies or antigen-binding fragments thereof of the present invention. Therapeutic compositions in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody may vary depending upon the age and the size of a subject to be administered, target disease, conditions, route of administration, and the like. When an antibody of the present invention is used for treating a disease or disorder in an adult patient, or for preventing such a disease, it is advantageous to administer the antibody of the present invention normally at a single dose of about 0.1 to about 60 mg/kg body weight, more preferably about 5 to about 60, about 10 to about 50, or about 20 to about 50 mg/kg body weight. Depending on the severity of the condition, the frequency and the duration of the treatment can be adjusted. In certain embodiments, the antibody or antigen-binding fragment thereof of the invention can be administered as an initial dose of at least about 0.1 mg to about 800 mg, about 1 to about 500 mg, about 5 to about 300 mg, or about 10 to about 200 mg, to about 100 mg, or to about 50 mg. In certain embodiments, the initial dose may be followed by administration of a second or a plurality of subsequent doses of the antibody or antigen-binding fragment thereof in an amount that can be approximately the same or less than that of the initial dose, wherein the subsequent doses are separated by at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al. (1987) J. Biol. Chem. 262:4429-4432). Methods of introduction include, but are not limited to, intradermal, transdermal, intramuscular, intraperitoneal, intravenous, subcutaneous, intranasal, epidural and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. The pharmaceutical composition can be also delivered in a vesicle, in particular a liposome (see, for example, Langer (1990) Science 249: 1527-1533).

The use of nanoparticles to deliver the antibodies of the present invention is also contemplated herein. Antibody-conjugated nanoparticles may be used both for therapeutic and diagnostic applications. Antibody-conjugated nanoparticles and methods of preparation and use are described in detail by Arruebo, M., et al. 2009 ("Antibody-conjugated nanoparticles for biomedical applications" in J. Nanomat. Volume 2009, Article ID 439389, 24 pages, doi: 10.1155/2009/439389), incorporated herein by reference. Nanoparticles may be developed and conjugated to antibodies contained in pharmaceutical compositions to target virally infected cells. Nanoparticles for drug delivery have also been described in, for example, U.S. Pat. Nos. 8,257,740, or 8,246,995, each incorporated herein in its entirety.

In certain situations, the pharmaceutical composition can be delivered in a controlled release system. In one embodiment, a pump may be used. In another embodiment, polymeric materials can be used. In yet another embodiment, a controlled release system can be placed in proximity of the composition's target, thus requiring only a fraction of the systemic dose.

The injectable preparations may include dosage forms for intravenous, subcutaneous, intracutaneous, intracranial, intraperitoneal and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (Sanofi-Aventis, Frankfurt, Germany), to name only a few. Examples of disposable pen delivery devices having applications in subcutaneous delivery of a pharmaceutical composition of the present invention include, but certainly are not limited to the SOLOSTAR™ pen (Sanofi-Aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L.P.) and the HUMIRA™ Pen (Abbott Labs, Abbott Park, Ill.), to name only a few.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the antibody contained is generally about 5 to about 500 mg per dosage form in a unit dose; especially in the form of injection, it is preferred that the antibody is contained in about 5 to about 100 mg and in about 10 to about 250 mg for the other dosage forms.

Therapeutic Uses of the Antibodies

The antibodies of the present invention are useful for the treatment, and/or prevention of a disease or disorder or condition associated with MERS-coronavirus such as MERS infection and/or for ameliorating at least one symptom associated with such disease, disorder or condition. In one embodiment, an antibody or antigen-binding fragment thereof the invention may be administered at a therapeutic dose to a patient with MERS infection.

In certain embodiments, the antibodies of the invention are useful to treat subjects suffering from the severe and acute respiratory infection caused by MERS-coronavirus. In some embodiments, the antibodies of the invention are useful in decreasing viral titer or reducing viral load in the host. In one embodiment, the antibodies of the present invention are useful in preventing or reducing inflammation in the lung of a subject with MERS. In one embodiment, the antibodies of the present invention are useful in preventing or reducing interstitial, peribronchiolar or perivascular inflammation, alveolar damage and pleural changes in a subject with MERS.

One or more antibodies of the present invention may be administered to relieve or prevent or decrease the severity of one or more of the symptoms or conditions of the disease or disorder. The antibodies may be used to ameliorate or reduce the severity of at least one symptom of MERS infection including, but not limited to consisting of fever, cough, shortness of breath, pneumonia, diarrhea, organ failure (e.g., kidney failure and renal dysfunction), septic shock and death.

It is also contemplated herein to use one or more antibodies of the present invention prophylactically to subjects at risk for developing MERS infection such as immunocompromised individuals, elderly adults (more than 65 years of age), children younger than 2 years of age, travelers to countries in the Middle East (e.g., Saudi Arabia, United Arab Emirates, and Qatar), healthcare workers, persons with occupational or recreational contact with camels or bats, family members in close proximity to a MERS patient, adults or children with contact with persons with confirmed or suspected MERS infection, and patients with a medical history (e.g., increased risk of pulmonary infection, heart disease or diabetes).

In a further embodiment of the invention the present antibodies are used for the preparation of a pharmaceutical composition or medicament for treating patients suffering from MERS infection. In another embodiment of the invention, the present antibodies are used as adjunct therapy with any other agent or any other therapy known to those skilled in the art useful for treating or ameliorating MERS infection.

Combination Therapies

Combination therapies may include an anti-MERS-CoV-S antibody of the invention and any additional therapeutic agent that may be advantageously combined with an antibody of the invention, or with a biologically active fragment of an antibody of the invention. The antibodies of the present invention may be combined synergistically with one or more drugs or therapy used to treat MERS. In some embodiments, the antibodies of the invention may be combined with a second therapeutic agent to reduce the viral load in a patient with MERS infection, or to ameliorate one or more symptoms of the infection.

The antibodies of the present invention may be used in combination with an anti-inflammatory drug (e.g., corticosteroids, and non-steroidal anti-inflammatory drugs), an anti-infective drug, a different antibody to MERS-CoV spike protein, an anti-viral drug, interferon-alpha-2b plus intramuscular ribavirin, convalescent plasma, an inhibitor of the main viral protease, and entry/fusion inhibitors targeting the MERS-CoV spike protein, a vaccine for MERS-CoV, antibiotics, a dietary supplement such as anti-oxidants or any other palliative therapy to treat MERS infection.

In certain embodiments, the second therapeutic agent is another antibody to MERS-CoV spike protein. It is contemplated herein to use a combination ("cocktail") of antibodies with broad neutralization or inhibitory activity against MERS-CoV. In some embodiments, non-competing antibodies may be combined and administered to a subject in need thereof, to reduce the ability of MERS virus to escape due to rapid mutation as a result of selection pressure. In some embodiments, the antibodies comprising the combination bind to distinct non-overlapping epitopes on the spike protein. The antibodies comprising the combination may block the MERS-CoV binding to DPP4 or may prevent/inhibit membrane fusion. The antibodies comprising the combination may inhibit MERS-CoV activity of one or more MERS-CoV isolates including, but not limited to, EMC/2012, Jordan-N3/2012, England-Qatar/2012, Al-Hasa_1_2013, Al-Hasa_2_2013, Al-Hasa_3_2013, Al-Hasa_4_2013, Al-Hasa_12, Al-Hasa_15, Al-Hasa_16, Al-Hasa_17, Al-Hasa_18, Al-Hasa_19, Al-Hasa_21, Al-hasa_25, Bisha_1, Buraidah_1, England 1, Hafr-Al-batin_1, Hafr-Al-Batin_2, Hafr-Al-Batin_6, Jeddah_1, KFU-HKU 1, KFU-HKU 13, Munich, Qatar3, Qatar4, Riyadh_1, Riyadh_2, Riyadh_3, Riyadh_3, Riyadh_4, Riyadh_5, Riyadh_9, Riyadh_14, Taif_1, UAE, and Wadi-Ad-Dawasir.

It is also contemplated herein to use a combination of anti-MERS-CoV-S antibodies of the present invention, wherein the combination comprises one or more antibodies that do not cross-compete; In some embodiments, the combination includes a first antibody with broad neutralization activity with a second antibody with activity against a narrow spectrum of isolates and that does not cross-compete with the first antibody.

As used herein, the term "in combination with" means that additional therapeutically active component(s) may be administered prior to, concurrent with, or after the administration of the anti-MERS-CoV-S antibody of the present invention. The term "in combination with" also includes sequential or concomitant administration of an anti-MERS-CoV-S antibody and a second therapeutic agent.

The additional therapeutically active component(s) may be administered to a subject prior to administration of an anti-MERS-CoV-S antibody of the present invention. For example, a first component may be deemed to be administered "prior to" a second component if the first component is administered 1 week before, 72 hours before, 60 hours before, 48 hours before, 36 hours before, 24 hours before, 12 hours before, 6 hours before, 5 hours before, 4 hours before, 3 hours before, 2 hours before, 1 hour before, 30 minutes before, 15 minutes before, 10 minutes before, 5 minutes before, or less than 1 minute before administration of the second component. In other embodiments, the additional therapeutically active component(s) may be administered to a subject after administration of an anti-MERS-CoV-S antibody of the present invention. For example, a first component may be deemed to be administered "after" a second component if the first component is administered 1 minute after, 5 minutes after, 10 minutes after, 15 minutes after, 30 minutes after, 1 hour after, 2 hours after, 3 hours after, 4 hours after, 5 hours after, 6 hours after, 12 hours after, 24 hours after, 36 hours after, 48 hours after, 60 hours after, 72 hours after administration of the second component. In yet other embodiments, the additional therapeutically active component(s) may be administered to a subject concurrent with administration of an anti-MERS-CoV-S antibody of the present invention. "Concurrent" administration, for purposes of the present invention, includes, e.g., administration of an anti-MERS-CoV-S antibody and an additional therapeutically active component to a subject in a single dosage form, or in separate dosage forms administered to the subject within about 30 minutes or less of each other. If administered in separate dosage forms, each dosage form may be administered via the same route (e.g., both the anti-MERS-CoV-S antibody and the additional therapeutically active component may be administered intravenously, etc.); alternatively, each dosage form may be administered via a different route (e.g., the anti-MERS-CoV-S antibody may be administered intravenously, and the additional therapeutically active component may be administered orally). In any event, administering the components in a single dosage from, in separate dosage forms by the same route, or in separate dosage forms by different routes are all considered "concurrent administration," for purposes of the present disclosure. For purposes of the present disclosure, administration of an anti-MERS-CoV-S antibody "prior to", "concurrent with," or "after" (as those terms are defined herein above) administration of an additional therapeutically active component is considered administration of an anti-MERS-CoV-S antibody "in combination with" an additional therapeutically active component.

The present invention includes pharmaceutical compositions in which an anti-MERS-CoV-S antibody of the present invention is co-formulated with one or more of the additional therapeutically active component(s) as described elsewhere herein.

Administration Regimens

According to certain embodiments, a single dose of an anti-MERS-CoV-S antibody of the invention (or a pharmaceutical composition comprising a combination of an anti-MERS-CoV-S antibody and any of the additional therapeutically active agents mentioned herein) may be administered to a subject in need thereof. According to certain embodiments of the present invention, multiple doses of an anti-MERS-CoV-S antibody (or a pharmaceutical composition comprising a combination of an anti-MERS-CoV-S antibody and any of the additional therapeutically active agents mentioned herein) may be administered to a subject over a defined time course. The methods according to this aspect of the invention comprise sequentially administering to a subject multiple doses of an anti-MERS-CoV-S antibody of the invention. As used herein, "sequentially administering" means that each dose of anti-MERS-CoV-S antibody is administered to the subject at a different point in time, e.g., on different days separated by a predetermined interval (e.g., hours, days, weeks or months). The present invention includes methods which comprise sequentially administering to the patient a single initial dose of an anti-MERS-CoV-S antibody, followed by one or more secondary doses of the anti-MERS-CoV-S antibody, and optionally followed by one or more tertiary doses of the anti-MERS-CoV-S antibody.

The terms "initial dose," "secondary doses," and "tertiary doses," refer to the temporal sequence of administration of the anti-MERS-CoV-S antibody of the invention. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of anti-MERS-CoV-S antibody, but generally may differ from one another in terms of frequency of administration. In certain embodiments, however, the amount of anti-MERS-CoV-S antibody contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In certain exemplary embodiments of the present invention, each secondary and/or tertiary dose is administered 1 to 48 hours (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) after the immediately preceding dose. The phrase "the immediately preceding dose," as used herein, means, in a sequence of multiple administrations, the dose of anti-MERS-CoV-S antibody which is administered to a patient prior to the administration of the very next dose in the sequence with no intervening doses.

The methods according to this aspect of the invention may comprise administering to a patient any number of secondary and/or tertiary doses of an anti-MERS-CoV-S antibody. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In certain embodiments of the invention, the frequency at which the secondary and/or tertiary doses are administered to a patient can vary over the course of the treatment regimen. The frequency of administration may also be adjusted during the course of treatment by a physician depending on the needs of the individual patient following clinical examination.

Diagnostic Uses of the Antibodies

The anti-MERS-CoV-S antibodies of the present invention may be used to detect and/or measure MERS-CoV in a sample, e.g., for diagnostic purposes. Some embodiments contemplate the use of one or more antibodies of the present invention in assays to detect a disease or disorder such as viral infection. Exemplary diagnostic assays for MERS-CoV may comprise, e.g., contacting a sample, obtained from a patient, with an anti-MERS-CoV-S antibody of the invention, wherein the anti-MERS-CoV-S antibody is labeled with a detectable label or reporter molecule or used as a capture ligand to selectively isolate MERS-CoV from patient samples. Alternatively, an unlabeled anti-MERS-CoV-S antibody can be used in diagnostic applications in combination with a secondary antibody which is itself detectably labeled. The detectable label or reporter molecule can be a radioisotope, such as $^{3}$H, $^{14}$C, $^{32}$P, $^{35}$S, or $^{125}$I; a fluorescent or chemiluminescent moiety such as fluorescein isothiocyanate, or rhodamine; or an enzyme such as alkaline phosphatase, β-galactosidase, horseradish peroxidase, or luciferase. Specific exemplary assays that can be used to detect or measure MERS-CoV in a sample include enzyme-linked immunosorbent assay (ELISA), radioimmunoassay (RIA), and fluorescence-activated cell sorting (FACS).

Samples that can be used in MERS-CoV diagnostic assays according to the present invention include any tissue or fluid sample obtainable from a patient, which contains detectable quantities of either MERS-CoV spike protein, or fragments thereof, under normal or pathological conditions. Generally, levels of MERS-CoV spike protein in a particular sample obtained from a healthy patient (e.g., a patient not afflicted with a disease associated with MERS-CoV) will be measured to initially establish a baseline, or standard, level of MERS-CoV. This baseline level of MERS-CoV can then be compared against the levels of MERS-CoV measured in samples obtained from individuals suspected of having a MERS-CoV-associated condition, or symptoms associated with such condition.

The antibodies specific for MERS-CoV spike protein may contain no additional labels or moieties, or they may contain an N-terminal or C-terminal label or moiety. In one embodiment, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, room temperature is about 25° C., and pressure is at or near atmospheric.

Example 1: Generation of Human Antibodies to MERS-CoV Spike Protein

Human antibodies to MERS-CoV spike protein were generated in a VELOCIMMUNE® mouse comprising DNA encoding human Immunoglobulin heavy and kappa light chain variable regions. The mice were immunized with a DNA construct encoding the full-length MERS-CoV spike protein followed by a booster dose comprising a purified fragment of the spike protein that ranges from amino acids 367-606 of GenBank Accession AFS88936.1 (SEQ ID NO: 457). Codon optimized cDNA sequence encoding for MERS-CoV S protein (EMC/2012—GenBank JX869059) was synthesized by GeneArt and cloned into standard expression vectors. Plasmids encoding MERS-CoV S protein variants in the Receptor Binding Domain (RBD) were generated by mutagenesis using QuikChange II (Agilent Technologies) according to the manufacturer's instructions.

The antibody immune response was monitored by a MERS-CoV-S-specific immunoassay. When a desired immune response was achieved splenocytes were harvested and fused with mouse myeloma cells to preserve their viability and form hybridoma cell lines. The hybridoma cell lines were screened and selected to identify cell lines that produce MERS-CoV-S-specific antibodies. Of a total of 696 hybridomas that express antigen-specific antibodies, 182 were found to block the interaction between DPP4 and spike protein and 123 blocked entry of MERSpp into target cells. Exemplary cell lines generated in this manner were designated as HBVX06H05, HBVX11H04, HBVX11D02, HBVZ10E10, HBVY09F08, HBVZ05G02, HBVZ09B06, HBVY01F08, HBVY10G02, HBVY04B06, HBVY07D10, HBVZ08A09, HBVZ05G04, HBVY06C07, HBVY03H06, HBVZ10G06, HBVZ04F10, HBVX11E09, HBVY06H09, HBVZ05B11, HBVY02E05 and HBVZ04C07. The cell lines were used to obtain several anti-MERS-CoV-S chimeric antibodies (i.e., antibodies possessing human variable domains and mouse constant domains); exemplary antibodies generated in this manner were designated as H1M15277N, H2aM15279N, H1M15280N, H2aM15278N, H2aM15271N, H1M15267N, H2bM15292N, H2bM15291N, H1M15290N, H1M15293N, H1M15289N, H1M15269N, H2aM15287N, H1M15288N, H2aM15268N, H2aM15270N, H2aM15281N, and H2aM15272N.

Table 1 shows selected chimeric antibodies obtained from the corresponding hybridoma supernatants.

TABLE 1

| Ab PID # | Clone Name |
|---|---|
| H1M15267N | HBVX11H04 |
| H1M15269N | HBVY07D10 |
| H1M15277N | HBVX06H05 |
| H1M15280N | HBVZ09B06 |
| H1M15288N | HBVY02E05 |
| H1M15289N | HBVY03H06 |
| H1M15290N | HBVZ04F10 |
| H1M15293N | HBVZ10G06 |
| H2aM15268N | HBVY04B06 |
| H2aM15270N | HBVY09F08 |
| H2aM15271N | HBVY10G02 |
| H2aM15272N | HBVZ05G02 |
| H2aM15278N | HBVX11D02 |
| H2aM15279N | HBVY01F08 |
| H2aM15281N | HBVZ10E10 |
| H2aM15287N | HBVX11E09 |
| H2bM15291N | HBVZ05G04 |
| H2bM15292N | HBVZ08A09 |

Anti-MERS-CoV-S antibodies were also isolated directly from antigen-positive mouse B cells without fusion to myeloma cells, as described in U.S. Pat. No. 7,582,298, herein specifically incorporated by reference in its entirety. Using this method, several fully human anti-MERS-CoV-S antibodies (i.e., antibodies possessing human variable domains and human constant domains) were obtained; exemplary antibodies generated in this manner were designated as H4sH15188P, H1H15188P, H1H15211P, H1H15177P, H4sH15211P, H1H15260P2, H1H15259P2, H1H15203P, H4sH15260P2, H4sH15231P2, H1H15237P2, H1H15208P, H1H15228P2, H1H15233P2, H1H15264P2, H1H15231P2, H1H15253P2, H1H15215P, and H1H15249P2.

The biological properties of the exemplary antibodies generated in accordance with the methods of this Example are described in detail in the Examples set forth below.

Example 2: Characterization of Hybridoma Supernatants

An ELISA binding assay was performed to identify antibody supernatants (obtained from the hybridomas described above) that bound to the MERS-CoV spike protein. A protein composed of the receptor binding domain of MERS-CoV-S (aa E367-Y606) expressed with the Fc portion of the human IgG1 molecule at the C-terminus (MERS RBD-hFc; SEQ ID NO: 458) was coated at 2 µg/ml on a 96-well plate in PBS buffer overnight at 4° C. Nonspecific binding sites were subsequently blocked using a 0.5% (w/v) solution of BSA in PBS. Hybridoma supernatants were diluted 1:50 in the blocking buffer and allowed to bind to the MERS RBD coated plates for 1 hour at room temperature. After washing, bound antibodies were detected using an HRP conjugated a-hFc polyclonal antibody (Jackson Immunochemical). Samples were developed with a 3,3',5,5'-tetramethylbenzidine solution (TMB; BD Biosciences) to produce a colorimetric reaction and then neutralized with 1M sulfuric acid before measuring absorbance at 450 nm on a Victor plate reader (Perkin Elmer). The results are shown in FIG. 1. Intensity of signal at 450 nm was used to select antibodies for further characterization.

Binding association and dissociation rate constants ($k_a$ and $k_d$, respectively), equilibrium dissociation constants and dissociation half-lives ($K_D$ and $t_{1/2}$, respectively) for antigen binding to hybridoma supernatants were determined using a real-time surface plasmon resonance biosensor assay on a Biacore 4000 or Biacore T200 instrument (details described in Example 4). As shown in FIG. 1, 21 of 22 hybridoma antibodies bound to MERS-CoV spike protein with $K_D$ values ranging from 245 pM to 21.5 nM.

The ability of anti-MERS coronavirus spike protein antibodies to block the receptor binding domain of MERS (MERS-RBD) binding to a cognate binding partner, human dipeptidyl peptidase 4 (hDPP4), was evaluated with an ELISA-based immunoassay. Briefly, human dipeptidyl peptidase 4 expressed with a 6× Histidine tag at the c-terminus (hDPP4-6His; R&D cat #1180-SE) was coated at 2 μg/mL on a 96-well plate in PBS buffer overnight at 4° C. Non-specific binding sites were subsequently blocked using a 0.5% (w/v) solution of BSA in PBS. This plate was used to measure MERS-RBD (aa E367-Y606) expressed with the Fc portion of the human IgG1 molecule at the c-terminus (MERS RBD-hFc; SEQ ID NO: 458) in a MERS RBD-hFc solution pre-equilibrated with a dilution of anti-MERS antibody supernatants. A constant concentration of 300 pM of MERS RBD-hFc was pre-mixed with a 10% volume of anti-MERS antibody supernatants, followed by an 1 hour incubation at room temperature (RT) to allow antibody-antigen binding to reach equilibrium. The equilibrated sample solutions were then transferred to hDPP4-6his-coated plates. After 1 hour of binding at RT, the plates were washed and bound MERS RBD was detected using HRP conjugated a-hFc polyclonal antibody (Jackson Immunochemical). Samples were developed with a TMB solution (BD Biosciences, #51-2606KC and #51-2607KC) to produce a colorimetric reaction and then neutralized with 1M sulfuric acid before measuring absorbance at 450 nm on a Victor X5 plate reader. The absorbance measured for the constant concentration of MERS RBD-hFc alone is defined as 0% blocking and the absorbance measured for no added MERS RBD-hFc is defined as 100% blocking. Percent blockade was calculated as the ratio of the reduction in signal observed in the presence of antibody relative to the difference between the signal with MERS RBD-hFc alone and background (signal from HRP conjugated a-hFc antibody alone) subtracted from 100% blocking as defined previously.

As shown in FIG. 1, 17 of 22 anti-MERS-CoV-S antibodies derived from separate independent hybridomas blocked more than 90% binding of MERS-CoV spike protein to DPP4.

The anti-MERS-CoV-S antibodies derived from separate independent hybridomas were tested for neutralization of MERS-infectivity (assay details in Example 5). As shown in FIG. 1, 12 of 22 cell anti-MERS-CoV-S hybridoma antibodies inhibited or neutralized more than 90% of MERS-infectivity and with $IC_{50}$ ranging from 68.4 pM to 3.58 nM.

Example 3: Heavy and Light Chain Variable Region Amino Acid and Nucleotide Sequences Table 2 sets forth the amino acid sequence identifiers of the heavy and light chain variable regions and CDRs of selected anti-MERS-CoV-S antibodies of the invention.

TABLE 2

Amino Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H1H15177P | 2 | 4 | 6 | 8 | 10 | 12 | 14 | 16 |
| H1H15188P | 18 | 20 | 22 | 24 | 26 | 28 | 30 | 32 |
| H1H15203P | 34 | 36 | 38 | 40 | 42 | 44 | 46 | 48 |
| H1H15208P | 50 | 52 | 54 | 56 | 58 | 60 | 62 | 64 |
| H1H15211P | 66 | 68 | 70 | 72 | 74 | 76 | 78 | 80 |
| H1H15215P | 82 | 84 | 86 | 88 | 90 | 92 | 94 | 96 |
| H1H15228P2 | 98 | 100 | 102 | 104 | 106 | 108 | 110 | 112 |
| H1H15231P2 | 114 | 116 | 118 | 120 | 106 | 108 | 110 | 112 |
| H1H15233P2 | 122 | 124 | 126 | 128 | 106 | 108 | 110 | 112 |
| H1H15237P2 | 130 | 132 | 134 | 136 | 106 | 108 | 110 | 112 |
| H1H15249P2 | 138 | 140 | 142 | 144 | 106 | 108 | 110 | 112 |
| H1H15253P2 | 146 | 148 | 150 | 152 | 106 | 108 | 110 | 112 |
| H1H15259P2 | 154 | 156 | 158 | 160 | 162 | 164 | 166 | 168 |
| H1H15260P2 | 170 | 172 | 174 | 176 | 162 | 164 | 166 | 168 |
| H1H15264P2 | 178 | 180 | 182 | 184 | 162 | 164 | 166 | 168 |
| H1M15267N2 | 186 | 188 | 190 | 192 | 194 | 196 | 198 | 200 |
| H1M15269N | 202 | 204 | 206 | 208 | 210 | 212 | 214 | 216 |
| H1M15277N | 218 | 220 | 222 | 224 | 226 | 228 | 230 | 232 |
| H1M15280N | 234 | 236 | 238 | 240 | 242 | 244 | 246 | 248 |
| H1M15289N | 250 | 252 | 254 | 256 | 258 | 260 | 262 | 264 |
| H1M15290N | 266 | 268 | 270 | 272 | 274 | 276 | 278 | 280 |
| H1M15293N | 282 | 284 | 286 | 288 | 290 | 292 | 294 | 296 |
| H2M15268N | 298 | 300 | 302 | 304 | 306 | 308 | 310 | 312 |
| H2M15270N | 314 | 316 | 318 | 320 | 322 | 324 | 326 | 328 |
| H2M15271N | 330 | 332 | 334 | 336 | 338 | 340 | 342 | 344 |
| H2M15272N | 346 | 348 | 350 | 352 | 354 | 356 | 358 | 360 |
| H2M15278N | 362 | 364 | 366 | 368 | 370 | 372 | 374 | 376 |
| H2M15279N | 378 | 380 | 382 | 384 | 386 | 388 | 390 | 392 |
| H2M15281N | 394 | 396 | 398 | 400 | 402 | 404 | 406 | 408 |
| H2M15287N | 410 | 412 | 414 | 416 | 418 | 420 | 422 | 424 |

TABLE 2-continued

Amino Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H2M15291N | 426 | 428 | 430 | 432 | 434 | 436 | 438 | 440 |
| H2M15292N | 442 | 444 | 446 | 448 | 450 | 452 | 454 | 456 |

The corresponding nucleic acid sequence identifiers are set forth in Table 3.

TABLE 3

Nucleic Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H1H15177P | 1 | 3 | 5 | 7 | 9 | 11 | 13 | 15 |
| H1H15188P | 17 | 19 | 21 | 23 | 25 | 27 | 29 | 31 |
| H1H15203P | 33 | 35 | 37 | 39 | 41 | 43 | 45 | 47 |
| H1H15208P | 49 | 51 | 53 | 55 | 57 | 59 | 61 | 63 |
| H1H15211P | 65 | 67 | 69 | 71 | 73 | 75 | 77 | 79 |
| H1H15215P | 81 | 83 | 85 | 87 | 89 | 91 | 93 | 95 |
| H1H15228P2 | 97 | 99 | 101 | 103 | 105 | 107 | 109 | 111 |
| H1H15231P2 | 113 | 115 | 117 | 119 | 105 | 107 | 109 | 111 |
| H1H15233P2 | 121 | 123 | 125 | 127 | 105 | 107 | 109 | 111 |
| H1H15237P2 | 129 | 131 | 133 | 135 | 105 | 107 | 109 | 111 |
| H1H15249P2 | 137 | 139 | 141 | 143 | 105 | 107 | 109 | 111 |
| H1H15253P2 | 145 | 147 | 149 | 151 | 105 | 107 | 109 | 111 |
| H1H15259P2 | 153 | 155 | 157 | 159 | 161 | 163 | 165 | 167 |
| H1H15260P2 | 169 | 171 | 173 | 175 | 161 | 163 | 165 | 167 |
| H1H15264P2 | 177 | 179 | 181 | 183 | 161 | 163 | 165 | 167 |
| H1M15267N2 | 185 | 187 | 189 | 191 | 193 | 195 | 197 | 199 |
| H1M15269N | 201 | 203 | 205 | 207 | 209 | 211 | 213 | 215 |
| H1M15277N | 217 | 219 | 221 | 223 | 225 | 227 | 229 | 231 |
| H1M15280N | 233 | 235 | 237 | 239 | 241 | 243 | 245 | 247 |
| H1M15289N | 249 | 251 | 253 | 255 | 257 | 259 | 261 | 263 |
| H1M15290N | 265 | 267 | 269 | 271 | 273 | 275 | 277 | 279 |
| H1M15293N | 281 | 283 | 285 | 287 | 289 | 291 | 293 | 295 |
| H2M15268N | 297 | 299 | 301 | 303 | 305 | 307 | 309 | 311 |
| H2M15270N | 313 | 315 | 317 | 319 | 321 | 323 | 325 | 327 |
| H2M15271N | 329 | 331 | 333 | 335 | 337 | 339 | 341 | 343 |
| H2M15272N | 345 | 347 | 349 | 351 | 353 | 355 | 357 | 359 |
| H2M15278N | 361 | 363 | 365 | 367 | 369 | 371 | 373 | 375 |
| H2M15279N | 377 | 379 | 381 | 383 | 385 | 387 | 389 | 391 |
| H2M15281N | 393 | 395 | 397 | 399 | 401 | 403 | 405 | 407 |
| H2M15287N | 409 | 411 | 413 | 415 | 417 | 419 | 421 | 423 |
| H2M15291N | 425 | 427 | 429 | 431 | 433 | 435 | 437 | 439 |
| H2M15292N | 441 | 443 | 445 | 447 | 449 | 451 | 453 | 455 |

Antibodies are typically referred to herein according to the following nomenclature: Fc prefix (e.g. "H4xH," "H1M," "H2M," etc.), followed by a numerical identifier (e.g. "15177," "15228," "15268," etc., as shown in Table 2), followed by a "P," "P2," "N," or "B" suffix. Thus, according to this nomenclature, an antibody may be referred to herein as, e.g., "H1H15177P," "H1H15228P2," "H2M15268N," etc. The H4sH, H1M, and H2M prefixes on the antibody designations used herein indicate the particular Fc region isotype of the antibody. For example, an "H4sH" antibody has a human IgG4 Fc with 2 or more amino acid changes as disclosed in US20100331527, an "H1M" antibody has a mouse IgG1 Fc, and an "H2M" antibody has a mouse IgG2 Fc (a or b isotype) (all variable regions are fully human as denoted by the first 'H' in the antibody designation). As will be appreciated by a person of ordinary skill in the art, an antibody having a particular Fc isotype can be converted to an antibody with a different Fc isotype (e.g., an antibody with a mouse IgG1 Fc can be converted to an antibody with a human IgG4, etc.), but in any event, the variable domains (including the CDRs)—which are indicated by the numerical identifiers shown in Table 2—will remain the same, and the binding properties to antigen are expected to be identical or substantially similar regardless of the nature of the Fc domain.

Example 4: Antibody Binding to MERS-CoV-S as Determined by Surface Plasmon Resonance Binding association and dissociation rate constants ($k_a$ and $k_d$, respectively), equilibrium dissociation constants and dissociation half-lives ($K_D$ and $t_{1/2}$, respectively) for antigen binding to purified anti-MERS-CoV-S antibodies or hybridoma supernatants were determined using a real-time surface plasmon resonance biosensor assay on a Biacore 4000 or Biacore T200 instrument. The Biacore sensor surface was derivatized with either a polyclonal rabbit anti-mouse antibody (GE, #BR-1008-38) or with a monoclonal mouse anti-human Fc antibody (GE, #BR-1008-39) to capture approximately 100-900 RUs of anti-MERS-CoV-S monoclonal antibodies, expressed with either a mouse Fc or a human Fc, respectively. The MERS-CoV reagents tested for binding to the anti-MERS-CoV-S antibodies included recombinant MERS-CoV-S receptor binding domain expressed with a C-terminal human IgG1 Fc (MERS RBD-hFc; SEQ ID NO: 458). Different concentrations of MERS-CoV reagent ranging from 3.7 nM to 200 nM were injected over the anti-MERS-CoV-S monoclonal antibody captured surface at a flow rate of 30 μL/min on Biacore 4000 or at 50 μL/min on Biacore T200. The binding of the MERS-CoV reagent to captured monoclonal antibodies was monitored for 3 to 5 minutes while their dissociation from the antibodies was monitored for 7 to 10 minutes in HBST running buffer (0.01 M HEPES pH 7.4, 0.15 M NaCl, 3 mM EDTA, 0.05% v/v Surfactant P20). Experiments were performed at 25° C. Kinetic association ($k_a$) and dissociation ($k_d$) rate constants were determined by processing and fitting the data to a 1:1 binding model using Scrubber 2.0c curve fitting software. Binding dissociation equilibrium constants ($K_D$) and dissociative half-lives ($t_{1/2}$) were then calculated from the kinetic rate constants as: $K_D$ (M)=$k_d/k_a$ and $t_{1/2}$ (min)= [ln 2/(60*$k_d$)].

In an initial experiment, binding dissociation equilibrium constants and dissociative half-lives were determined for 22 hybridoma supernatants (described in Example 2).

In subsequent experiments, the purified antibodies were tested for binding to MERS-CoV spike protein using the surface plasmon resonance assay described above.

TABLE 4

Binding Kinetics @ 25° C.

| mAb Captured | mAb Capture Level (RU) | 100 nM Ag Bound (RU) | ka (1/Ms) | kd (1/s) | KD (M) | t½ (min) |
|---|---|---|---|---|---|---|
| H2aM15281N | 223 ± 0.8 | 127 | 2.10E+06 | 8.18E−04 | 3.90E−10 | 14 |
| H1M15289N | 224 ± 1.5 | 88 | 2.10E+05 | 4.41E−05 | 2.10E−10 | 262 |
| H1M15267N | 173 ± 0.7 | 109 | 8.43E+05 | 1.53E−04 | 1.81E−10 | 75 |
| H2aM15272N | 229 ± 1.1 | 120 | 1.65E+06 | 7.33E−04 | 4.43E−10 | 16 |
| H2aM15279N | 195 ± 0.7 | 127 | 8.70E+05 | 8.91E−05 | 1.02E−10 | 130 |
| H2aM15278N | 230 ± 1 | 118 | 1.72E+06 | 8.73E−04 | 5.06E−10 | 13 |
| H2aM15268N | 174 ± 0.6 | 121 | 2.68E+06 | 9.50E−04 | 3.55E−10 | 12 |
| H2aM15270N | 182 ± 0.7 | 107 | 7.79E+05 | 6.05E−04 | 7.76E−10 | 19 |
| H1M15277N | 211 ± 1 | 150 | 2.63E+06 | 9.10E−04 | 3.46E−10 | 13 |
| H2bM15292N | 185 ± 1.2 | 95 | 4.57E+05 | 1.55E−04 | 3.40E−10 | 75 |
| H2aM15271N | 227 ± 1.4 | 112 | 9.08E+05 | 1.24E−03 | 1.37E−09 | 9 |
| H1M15269N | 268 ± 2.8 | 83 | 1.76E+05 | 1.08E−04 | 6.16E−10 | 107 |
| H1M15290N | 210 ± 1.9 | 108 | 4.82E+05 | 2.11E−04 | 4.38E−10 | 55 |
| H1M15293N | 187 ± 0.9 | 91 | 6.04E+05 | 1.98E−04 | 3.28E−10 | 58 |
| H2bM15291N | 179 ± 1.8 | 83 | 2.52E+05 | 1.41E−04 | 5.59E−10 | 82 |
| H1M15288N | 149 ± 1 | 55 | 1.73E+05 | 7.16E−04 | 4.15E−09 | 16 |
| H2aM15287N | 186 ± 1.9 | 50 | 6.33E+04 | 4.42E−04 | 6.98E−09 | 26 |
| H1M15280N | 168 ± 0.8 | 56 | 2.83E+05 | 5.25E−03 | 1.85E−08 | 2.2 |
| H1H15233P2 | 250 ± 13.2 | 141 | 1.99E+05 | 4.56E−05 | 2.29E−10 | 253 |
| H1H15231P2 | 228 ± 3.8 | 154 | 6.39E+05 | 7.44E−05 | 1.16E−10 | 155 |
| H1H15188P | 189 ± 1.4 | 158 | 1.48E+06 | 1.22E−04 | 8.25E−11 | 95 |
| H1H15211P | 226 ± 1.1 | 180 | 1.13E+06 | 8.72E−05 | 7.75E−11 | 133 |
| H1H15249P2 | 195 ± 1.2 | 99 | 3.49E+05 | 7.91E−05 | 2.27E−10 | 146 |
| H1H15260P2 | 242 ± 2 | 164 | 1.16E+06 | 1.60E−04 | 1.38E−10 | 72 |
| H1H15203P | 128 ± 1.4 | 100 | 4.43E+05 | 1.21E−04 | 2.73E−10 | 95 |
| H1H15237P2 | 171 ± 2.2 | 131 | 4.39E+05 | 1.20E−04 | 2.74E−10 | 96 |
| H1H15264P2 | 110 ± 2.9 | 66 | 2.23E+05 | 1.86E−04 | 8.33E−10 | 62 |
| H1H15228P2 | 144 ± 4.3 | 113 | 4.43E+05 | 1.85E−04 | 4.18E−10 | 63 |
| H1H15208P | 114 ± 4.3 | 98 | 4.39E+05 | 2.43E−04 | 5.53E−10 | 48 |
| H1H15177P | 135 ± 1.3 | 105 | 4.93E+05 | 1.92E−04 | 3.90E−10 | 60 |
| H1H15253P2 | 127 ± 1.7 | 94 | 3.56E+05 | 1.24E−04 | 3.48E−10 | 93 |
| H1H15215P | 171 ± 1 | 86 | 1.44E+06 | 9.67E−05 | 6.71E−10 | 119 |
| H1H15259P2 | 234 ± 2.1 | 142 | 2.26E+05 | 3.77E−04 | 1.67E−09 | 31 |

TABLE 5

Binding Kinetics @ 37° C.

| mAb Captured | mAb Capture Level (RU) | 100 nM Ag (RU) | ka (1/Ms) | kd (1/s) | KD (M) | t1/2 (min) |
|---|---|---|---|---|---|---|
| H2aM15281N | 276 ± 1.6 | 140 | 2.55E+06 | 5.43E−04 | 2.13E−10 | 21 |
| H1M15289N | 271 ± 2.2 | 119 | 4.59E+05 | 1.26E−04 | 2.75E−10 | 92 |
| H1M15267N | 202 ± 1.1 | 132 | 2.37E+06 | 7.45E−04 | 3.14E−10 | 16 |
| H2aM15272N | 284 ± 1.9 | 135 | 2.00E+06 | 6.34E−04 | 3.16E−10 | 18 |
| H2aM15279N | 229 ± 1 | 150 | 1.39E+06 | 4.45E−04 | 3.20E−10 | 26 |
| H2aM15278N | 266 ± 1.1 | 127 | 2.17E+06 | 1.13E−03 | 5.19E−10 | 10 |
| H2aM15268N | 208 ± 1.1 | 126 | 3.75E+06 | 2.02E−03 | 5.37E−10 | 6 |
| H2aM15270N | 219 ± 0.8 | 128 | 1.75E+06 | 1.14E−03 | 6.51E−10 | 10 |
| H1M15277N | 246 ± 1.1 | 156 | 3.24E+06 | 2.18E−03 | 6.71E−10 | 5 |
| H2bM15292N | 242 ± 0.6 | 117 | 5.44E+05 | 5.24E−04 | 9.63E−10 | 22 |

TABLE 5-continued

| | | Binding Kinetics @ 37° C. | | | |
|---|---|---|---|---|---|
| mAb Captured | mAb Capture Level (RU) | 100 nM Ag (RU) | ka (1/Ms) | kd (1/s) | KD (M) | t1/2 (min) |
| H2aM15271N | 276 ± 1.5 | 117 | 1.45E+06 | 1.45E−03 | 1.00E−09 | 8 |
| H1M15269N | 319 ± 1.7 | 107 | 2.54E+05 | 3.39E−04 | 1.34E−09 | 34 |
| H1M15290N | 243 ± 1.8 | 117 | 6.66E+05 | 9.84E−04 | 1.48E−09 | 12 |
| H1M15293N | 213 ± 1.7 | 112 | 5.12E+05 | 8.53E−04 | 1.66E−09 | 14 |
| H2bM15291N | 229 ± 1.7 | 97 | 3.42E+05 | 6.40E−04 | 1.87E−09 | 18 |
| H1M15288N | 176 ± 1 | 69 | 2.73E+05 | 2.08E−04 | 7.61E−09 | 6 |
| H2aM15287N | 228 ± 1.4 | 61 | 1.74E+05 | 1.89E−03 | 1.09E−08 | 6 |
| H1M15280N | 196 ± 1 | 59 | 4.97E+05 | 6.57E−03 | 1.32E−08 | 1.8 |
| H1H15233P2 | 317 ± 6.9 | 184 | 3.74E+05 | 4.74E−05 | 1.27E−10 | 244 |
| H1H15231P2 | 306 ± 4.3 | 228 | 6.59E+05 | 9.19E−05 | 1.39E−10 | 126 |
| H1H15188P | 267 ± 1.6 | 217 | 1.59E+06 | 2.65E−04 | 1.67E−10 | 44 |
| H1H15211P | 305 ± 2.7 | 232 | 8.27E+05 | 1.60E−04 | 1.94E−10 | 72 |
| H1H15249P2 | 260 ± 2.3 | 157 | 4.42E+05 | 1.27E−04 | 2.88E−10 | 91 |
| H1H15260P2 | 322 ± 2.5 | 220 | 1.05E+06 | 5.47E−04 | 5.19E−10 | 21 |
| H1H15203P | 179 ± 1.2 | 106 | 5.01E+05 | 3.23E−04 | 6.45E−10 | 36 |
| H1H15237P2 | 218 ± 1.4 | 181 | 5.14E+05 | 4.09E−04 | 7.97E−10 | 28 |
| H1H15264P2 | 149 ± 2.1 | 106 | 5.07E+05 | 4.75E−04 | 9.36E−10 | 24 |
| H1H15228P2 | 188 ± 2 | 157 | 4.76E+05 | 4.64E−04 | 9.75E−10 | 25 |
| H1H15208P | 151 ± 3.6 | 145 | 5.25E+05 | 5.31E−04 | 1.01E−09 | 22 |
| H1H15177P | 181 ± 1.5 | 149 | 5.68E+05 | 7.01E−04 | 1.23E−09 | 16 |
| H1H15253P2 | 172 ± 0.7 | 139 | 4.36E+05 | 6.29E−04 | 1.44E−09 | 18 |
| H1H15215P | 224 ± 2.1 | 96 | 1.38E+05 | 2.33E−04 | 1.68E−09 | 50 |
| H1H15259P2 | 282 ± 3.8 | 173 | 4.78E+05 | 8.88E−04 | 1.86E−09 | 13 |

As shown in Tables 4 and 5, the antibodies bound to MERS-CoV spike protein with $K_D$ values ranging from 77.5 pM to 18.5 nM at 25° C. and from 127 pM to 13.2 nM at 37° C. The antibodies showed dissociative half-life (t½) values ranging from 2.2 to 262 minutes at 25° C. and from 1.8 to 244 minutes at 37° C.

Example 5: Antibody-Mediated Neutralization of MERS Infectivity

Materials and Methods

Generation of Pseudoparticles

MERS pseudoparticles (MERSpp; also called as virus like particle—VLP) were generated by co-transfecting 293T cells with a mix of plasmid constructs expressing MERS spike protein, HIV gag-pol, and an HIV proviral vector encoding for firefly luciferase. Supernatants containing MERSpp were harvested at 72 hours post transfection, clarified using centrifugation, concentrated, aliquoted and frozen at −80° C. Control pseudoparticles were generated by substituting the plasmid expressing MERS-CoV Spike protein with a plasmid encoding for Vesicular Stomatitis Virus Glycoprotein (VSVg).

MERSpp-Based Assay

Dilutions of antibodies were incubated with MERSpp for 1 h at room temperature. Huh7 cells in complete DMEM media were detached using 1% EDTA, washed and incubated with the antibody/MERSpp mixtures for 72 h. Infection efficiency was quantitated by luciferase detection with the BrightGlo® luciferase assay (Promega, San Luis Obispo, Calif., USA) and read in a Victor® X3 plate reader (Perkin Elmer, Waltham, Mass., USA) for light production.

Virus-Based Assay $1\times10^4$ Vero E6 cells per well were seeded into 96-well plates 1 day prior to the experiment. 500 $TCID_{50}$ of MERS-CoV EMC/2012 strain was mixed with the stated amount of antibody in 100 ul normal Vero E6 growth media and incubated at room temperature for 30 minutes and the mixture was then added to the Vero E6 cells. At 2 days post-infection, cell death was assessed using the CellTiter-Glo® Luminescent Cell Viability Assay (Promega) according to the manufacturers' instructions. Luminescence was read on Spectramax M plate reader (Molecular Devices). Data was expressed as percent of mock-infected controls.

Results

Neutralization of MERS-CoV by Anti-MERS-CoV-S Antibodies

In an initial experiment, the anti-MERS-CoV-S antibodies derived from separate independent hybridomas were tested for neutralization of MERS-infectivity. As shown in FIG. 1, 12 of 22 cell anti-MERS-CoV-S hybridoma antibodies inhibited or neutralized more than 90% of MERS-infectivity and with $IC_{50}$ ranging from 68.4 pM to 3.58 nM.

In subsequent experiments, the purified antibodies were tested for neutralization of MERSpp and live MERS virus (Isolate: EMC/2012). The results are shown in Tables 6 and 7.

TABLE 6

| Antibody | IC50 against MERSpp (M) | IC50 against live virus (EMC2012) (M) |
|---|---|---|
| H1M15277N | 6.46E−11 | 2.87E−10 |
| H2aM15279N | 9.39E−11 | 8.25E−10 |
| H1M15280N | 1.11E−10 | 7.63E−10 |
| H2aM15278N | 1.42E−10 | 6.44E−10 |
| H2aM15271N | 1.27E−10 | 1.03E−09 |
| H1M15267N | 9.98E−11 | 8.91E−10 |
| H2bM15292N | 1.13E−10 | 2.26E−09 |
| H2bM15291N | 1.86E−10 | 2.22E−09 |
| H1M15290N | 2.10E−10 | 2.55E−09 |
| H1M15293N | 2.58E−10 | 2.58E−09 |
| H1M15289N | 2.81E−10 | 3.15E−09 |
| H1M15269N | 6.88E−10 | 6.80E−09 |
| H2aM15287N | 2.93E−09 | 8.92E−09 |
| H1M15288N | ~0.1209 | 2.66E−08 |
| H2aM15268N | 5.89E−11 | 2.72E−10 |
| H2aM15270N | 1.02E−10 | 7.11E−10 |
| H2aM15281N | 7.85E−11 | 2.92E−10 |
| H2aM15272N | 7.23E−11 | 5.69E−10 |

TABLE 7

| Antibody | IC50 against MERSpp (M) | IC50 against live virus (EMC2012) (M) |
|---|---|---|
| H1H15211P | 4.74E-11 | 3.69E-10 |
| H1H15188P | 6.20E-11 | 5.05E-10 |
| H1H15177P | 4.57E-11 | 6.29E-10 |
| H1H15203P | 7.65E-11 | 8.26E-10 |
| H1H15228P2 | 9.75E-11 | 8.98E-10 |
| H1H15231P2 | 1.02E-10 | 9.20E-10 |
| H1H15237P2 | 6.60E-11 | 1.01E-09 |
| H1H15233P2 | 8.73E-11 | 1.37E-09 |
| H1H15259P2 | 7.64E-11 | 1.63E-09 |
| H1H15264P2 | 1.34E-10 | 2.39E-09 |
| H1H15208P | 8.27E-11 | 2.41E-09 |
| H1H15253P2 | 1.51E-10 | 2.42E-09 |
| H1H15215P | 1.92E-10 | 2.67E-09 |
| H1H15260P2 | 6.43E-11 | 6.70E-09 |
| H1H15249P2 | 2.27E-10 | 1.20E-08 |
| H4sH15188P | 2.91E-11 | NA |
| H4sH15211P | 6.08E-11 | NA |
| H4sH15260P2 | 6.24E-11 | NA |
| H4sH15231P2 | 7.33E-11 | NA |

The data above suggest that the anti-MERS-CoV-S antibodies of the present invention potently block the entry of MERS-CoV into susceptible cells and neutralize infectivity.

Neutralization of Clinical Isolates by Anti-MERS-CoV-S Antibodies

RNA viruses encode low-fidelity genome replication machinery, which allows them to rapidly adapt to their host environment (Malpica et al 2002; Genetics 162: 1505-1511). However, coronaviruses, such as MERS-CoV, encode for a non-structural protein with a 3'-to-5' exo-ribonuclease activity, that provides a proof-reading function during their replication and greatly increases the coding capacity of the genome without leading to mutational catastrophe (Cotton et al 2013; Lancet doi:10.1016/S0140-6736(13)61887-5). Despite that, sequencing of multiple clinical isolates sampled during the first two years of the MERS-CoV epidemic has revealed that the MERS-CoV S protein of the virus is evolving (Cotton et al 2014; MBio 5 doi:10.1128/mBio.01062-13). For this study, 38 NCBI deposited sequences of MERS-CoV clinical isolates were aligned and compared to the sequence of the first isolated strain, EMC/2012. Based on the design of the screening assay, the antibodies of the present invention were expected to bind within the RBD of the MERS-CoV S protein, so the comparison of the sequences specifically focused on amino acids 367-606. Seven different amino acids were identified that differ between the sequenced clinical isolates and the prototype EMC/2012 sequence, A431P, S457G, S460F, A482V, L506F, D509G and V534A (Table 8).

TABLE 8

| Amino Acid change | Isolate |
|---|---|
| A431P | Riyadh_9 |
| S457G | KFU-HKU 1; KFU-HKU 13 |
| S469F | Qatar3; Qatar4 |
| A482V | Riyadh_9 |
| L506F | England 1; England-Qatar/2012 |
| D509G | Bisha_1; Riyadh_1 |
| V534A | Riyadh_2 |

To test the ability of the antibodies to bind to conserved regions within the RBD and neutralize all MERS-CoV clinical isolates sequenced as of July 2014, site-directed mutagenesis was used to create plasmid constructs encoding for all S protein variants. These were used to generate MERSpp pseudotyped with the modified S proteins and performed neutralization assays. The purified antibodies (described in Example 1) were tested for neutralization of MERS-infectivity using MERSpp generated with the above-mentioned mutations. Tables 9 and 10 show the percent neutralization of MERSpp variants.

TABLE 9

| RBD Variant | wt | A431P | S457G | S460F | A482V | L506F | D509G |
|---|---|---|---|---|---|---|---|
| Antibody µg/mL | 0.02 | 0.02 | 0.02 | 0.02 | 0.02 | 0.02 | 0.02 |
| H1M15267N | 71.65% | 68.15% | 70.81% | 76.82% | 66.78% | 57.11% | 84.91% |
| H1M15269N | 7.19% | 11.87% | 27.48% | 19.57% | 7.74% | 21.09% | 7.08% |
| H1M15280N | 56.69% | 59.42% | 74.42% | 73.14% | 65.89% | 65.90% | 38.21% |
| H1M15277N | 75.83% | 89.05% | 90.07% | 89.35% | 75.14% | 83.27% | 62.26% |
| H2aM15268N | 79.86% | 89.51% | 93.08% | 89.11% | 83.50% | 88.63% | 87.74% |
| H2aM15270N | 63.45% | 81.24% | 81.64% | 80.51% | 67.96% | 79.63% | 45.28% |
| H2aM15271N | 53.38% | 63.32% | 67.50% | 65.52% | 52.90% | 4.79% | 38.21% |
| H2aM15272N | 62.88% | 72.97% | 78.34% | 80.51% | 58.90% | 16.58% | 7.08% |
| H2aM15281N | 78.99% | 85.38% | 86.76% | 83.70% | 73.96% | 17.87% | 19.81% |
| H2aM15279N | 48.92% | 68.84% | 69.91% | 65.27% | 55.36% | 71.27% | 53.77% |
| H2aM15278N | 50.50% | 65.39% | 70.81% | 73.87% | 48.97% | 56.25% | -29.72% |
| H1M15288N | 1.29% | 11.64% | 20.86% | 26.45% | 23.68% | 8.22% | -2.83% |
| H1M15289N | 43.74% | 44.26% | 45.54% | 51.27% | 36.86% | 42.32% | 28.30% |
| H1M15290N | 36.55% | 39.20% | 43.73% | 48.08% | 22.89% | -0.14% | -39.62% |
| H1M15293N | 27.91% | 29.10% | 34.40% | 40.21% | 20.33% | 1.57% | -15.57% |
| H2aM15287N | 11.65% | 5.90% | 12.14% | 15.15% | 19.06% | 15.30% | -1.42% |
| H2bM15291N | 45.90% | 38.74% | 50.05% | 49.80% | 28.30% | -3.57% | 18.40% |
| H2bM15292N | 42.01% | 41.04% | 49.45% | 51.02% | 40.21% | 14.87% | -16.98% |
| Isotype control (mIgG1) | -0.14% | 10.03% | -3.81% | 1.39% | -5.25% | 2.64% | -24.06% |
| Isotype control (mIgG2a) | 5.32% | -1.00% | 7.32% | 8.76% | 10.30% | 5.65% | -26.89% |
| Isotype control (mIgG2b) | 0.43% | -5.13% | 26.88% | 5.08% | 13.35% | 6.08% | -4.25% |
| H1H15211P | 87.77% | 90.20% | 93.98% | 93.78% | 88.82% | 91.85% | 80.66% |
| H4sH15211P | 91.65% | 95.02% | 98.80% | 91.81% | 95.41% | 96.35% | 67.92% |
| Isotype control (hIgG1) | 11.80% | 10.26% | -11.63% | 3.60% | 15.61% | 6.08% | -8.49% |
| Isotype control (hIgG4) | -4.60% | -0.54% | -0.50% | -0.33% | 13.84% | -5.50% | 8.49% |

TABLE 10

| RBD variant | wt | A431P | S457G | S460F | A482V | L506F | D509G |
|---|---|---|---|---|---|---|---|
| Ab ID µg/mL | 0.02 | 0.02 | 0.02 | 0.02 | 0.02 | 0.02 | 0.02 |
| H4sH15188P | 81.6% | 89.7% | 95.7% | 92.6% | 74.2% | 93.6% | 101.4% |
| H4sH15211P | 77.1% | 91.6% | 88.1% | 86.0% | 73.8% | 88.2% | 57.2% |
| H4sH15231P2 | 70.6% | 72.3% | 74.5% | 75.7% | 70.5% | 80.6% | 60.0% |
| H4sH15260P2 | 73.3% | 82.8% | 77.7% | 74.8% | 79.0% | 73.3% | 73.8% |
| H1H15177P | 82.8% | 83.2% | 84.4% | 84.5% | 75.9% | 90.9% | 35.2% |
| H1H15188P | 81.4% | 88.9% | 86.8% | 85.5% | 86.4% | 92.4% | 90.3% |
| H1H15203P | 61.0% | 80.5% | 74.5% | 74.0% | 74.0% | 61.3% | 35.2% |
| H1H15208P | 53.9% | 79.3% | 73.8% | 77.7% | 65.2% | 76.5% | 82.1% |
| H1H15211P | 77.8% | 87.3% | 93.5% | 94.6% | 80.2% | 82.6% | 79.3% |
| H1H15215P | 20.2% | 43.0% | 42.4% | 44.0% | 41.7% | 15.8% | −47.6% |
| H1H15228P2 | 47.8% | 64.1% | 68.4% | 57.4% | 63.1% | 74.8% | 62.8% |
| H1H15231P2 | 48.1% | 60.6% | 71.4% | 55.7% | 60.0% | 55.2% | 46.2% |
| H1H15233P2 | 55.4% | 66.8% | 69.7% | 59.9% | 65.0% | 50.8% | 65.5% |
| H1H15237P2 | 52.6% | 74.4% | 82.7% | 73.5% | 70.5% | 73.8% | 79.3% |
| H1H15249P2 | 15.6% | 34.6% | 19.8% | 34.2% | 37.2% | 30.7% | 29.7% |
| H1H15253P2 | 52.9% | 66.4% | 56.0% | 57.7% | 58.2% | 56.9% | 51.7% |
| H1H15259P2 | 61.2% | 79.3% | 77.1% | 63.8% | 68.1% | 73.0% | 79.3% |
| H1H15260P2 | 68.8% | 85.6% | 74.5% | 86.7% | 80.4% | 82.1% | 54.5% |
| H1H15264P2 | 23.1% | 55.5% | 52.3% | 52.3% | 40.1% | 47.4% | −20.0% |
| Isotype control (hIgG1) | −38.0% | −0.3% | 1.6% | −36.9% | 0.8% | −16.9% | 15.9% |
| Isotype control (hIgG4) | −19.9% | 1.1% | −4.5% | −8.1% | 6.7% | −7.4% | 15.9% |
| H1M15277N | 35.2% | 86.7% | 83.1% | 65.0% | 75.1% | 73.0% | 71.0% |
| Isotype control (mIgG1) | −8.8% | 2.6% | −3.6% | 3.7% | 0.2% | −9.6% | 26.9% |

These data suggest that the antibodies of the present invention bind to regions of the MERS-CoV spike protein that are conserved during natural evolution of the virus.

Anti-MERS-CoV-S Antibodies of the Inventions are More Effective Neutralizers that Previously Isolated Anti-MERS-CoV Antibodies The potency of selected antibodies of the invention was compared with previously isolated monoclonal antibodies. Three groups have used in vitro antibody isolation methods, i.e. phage display (Tang et al 2014, PNAS doi:10.1073/pnas.1402074111; and Ying et al 2014, J. Virol. doi:10.1128/JVI.00912-14) and yeast display (Jiang et al 2014, Sci. Transl. Med. doi:10.1126/scitranslmed.3008140), to select for antibodies that bind to MERS-CoV S protein and block virus entry. For this study, a panel of three antibodies with published variable domain sequences which were reported to neutralize MERS-CoV and bind to diverse epitopes was selected. Sequences for antibodies 3B12 (Tang et al 2014, PNAS doi:10.1073/pnas.1402074111), MERS-4 and MERS-27 (Jiang et al 2014, Sci. Transl. Med. doi:10.1126/scitranslmed.3008140) were cloned onto human IgG1 constant domains, then expressed and purified similarly to selected antibodies of the present invention. The neutralization efficacy of all antibodies was tested using pseudoparticles generated with the prototypical EMC/2012 sequence and all clinical isolates described above.

The neutralization IC50 of selected antibodies against MERSpp variants is shown in Table 11. As seen in Table 11, H1H15211P was able to neutralize all isolates with $IC_{50}$ values ranging from 1.3E−11M to 6.5E−11M. Similar values were also observed for H1H15277N, with the exception of the V534A variant, which exhibited a partial resistance to the antibody. It is worth noting however, that this amino acid change was only observed in a single MERS-CoV isolate (Riyadh_2), which was isolated in 2012 and is part of a dead branch of the MERS-CoV evolutionary tree.

H1H15211P and H1H277N neutralize MERSpp with $IC_{50}$ values at least one log lower than the most potent comparator antibody, MERS-4. In addition, both 3B12 and MERS-27 appear to bind to less conserved sites on the MERS-CoV S protein, as pseudoparticles with sequences of multiple clinical isolates cannot be neutralized with these antibodies.

TABLE 11

| | H1H15177P | H1H15188P | H1H15211P | H1H15277N | H1H15267N2 | 3B12 | MERS-4 | MERS-27 |
|---|---|---|---|---|---|---|---|---|
| wt | 5.374E−11 | 4.819E−11 | 6.525E−11 | 6.978E−11 | 7.621E−11 | 1.69E−09 | 3.90E−10 | 8.36E−09 |
| A431P | 1.924E−11 | 1.323E−11 | 2.15E−11 | 3.162E−11 | 4.877E−11 | 6.35E−10 | 2.02E−10 | 4.50E−09 |
| S457G | 3.022E−11 | 1.99E−11 | 2.578E−11 | 3.532E−11 | 4.973E−11 | 7.43E−10 | 2.81E−10 | 5.06E−09 |
| S460F | 2.435E−11 | 1.49E−11 | 2.031E−11 | 3.19E−11 | 6.805E−11 | 6.69E−10 | 3.14E−10 | 6.36E−09 |
| A482V | 2.044E−11 | 1.955E−11 | 2.735E−11 | 8.094E−11 | 6.533E−11 | 9.58E−10 | 6.83E−10 | 1.26E−08 |
| L506F | 1.624E−11 | 1.017E−11 | 1.341E−11 | 3.967E−11 | 3.537E−11 | ~0.001534 | 5.64E−10 | 6.64E−09 |
| D509G | 1.792E−10 | 1.682E−11 | 4.036E−11 | 4.322E−11 | 4.846E−11 | 1.17E−07 | 1.37E−09 | 4.57E−09 |
| V534A | 3.663E−11 | 2.034E−11 | 3.195E−11 | 7.064E−09 | 4.317E−10 | 5.63E−08 | 2.19E−10 | 1.31E−07 |

These data suggest that antibodies of the present invention are able to neutralize a broader range of MERS-CoV isolates with improved potency compared to several antibodies isolated solely based on in vitro biochemical properties.

Example 6: Octet Cross-Competition Between Anti-MERS-CoV-S Antibodies

Binding competition between MERS-CoV S antibodies was determined using a real time, label-free bio-layer interferometry assay on an Octet® RED96 biosensor (Pall ForteBio Corp). The entire experiment was performed at 25° C. in HBS-P Octet buffer (10 mM HEPES, 150 mM NaCl, and 0.05% v/v Surfactant Tween-20, pH 7.4, 1 mg/mL BSA) with the plate shaking at the speed of 1000 rpm. To assess whether antibodies are able to compete with one another for binding to their respective epitopes on a recombinantly expressed MERS spike protein receptor binding domain fused to a human Fc tag (MERS RBD-hFc; SEQ ID: 458), a pre-mix assay format was adopted and 50 nM of MERS-CoV-RBD-mFc was pre-incubated with 500 nM of different anti-MERS monoclonal antibody (subsequently referred to as mAb-2) for at least 2 hours prior to performing the binding competition assay. A non-specific monoclonal antibody was incubated with MERS-RBS.mFc as an Isotype control. Octet biosensors coated with an anti-hFc polyclonal antibody (Pall ForteBio Corp., Cat #18-5060) were first submerged into wells containing 50 µg/mL solution for 4 minutes to capture around 2 nm of anti-MERS antibody (subsequently referred to as mAb-1). Following the capture step, unoccupied anti-hFc polyclonal antibodies were then saturated by submerging Octet biosensors into wells containing 100 µg/mL of non-specific fully human monoclonal antibody. Finally, the biosensors were immersed for 4 minutes into wells containing the pre-mixed samples of 50 nM of MERS-RBD-mFc and 500 nM of mAb-2. The biosensors were washed in HBS-P Octet buffer in between every step of the experiment. The real-time binding response was monitored during the course of the experiment and the binding response at the end of every step was measured. The response of mAb-1 binding to the pre-complex of MERS-RBD-mFc and mAb-2 was compared and competitive/non-competitive behavior of different anti-MERS monoclonal antibodies was determined.

Figure 2:
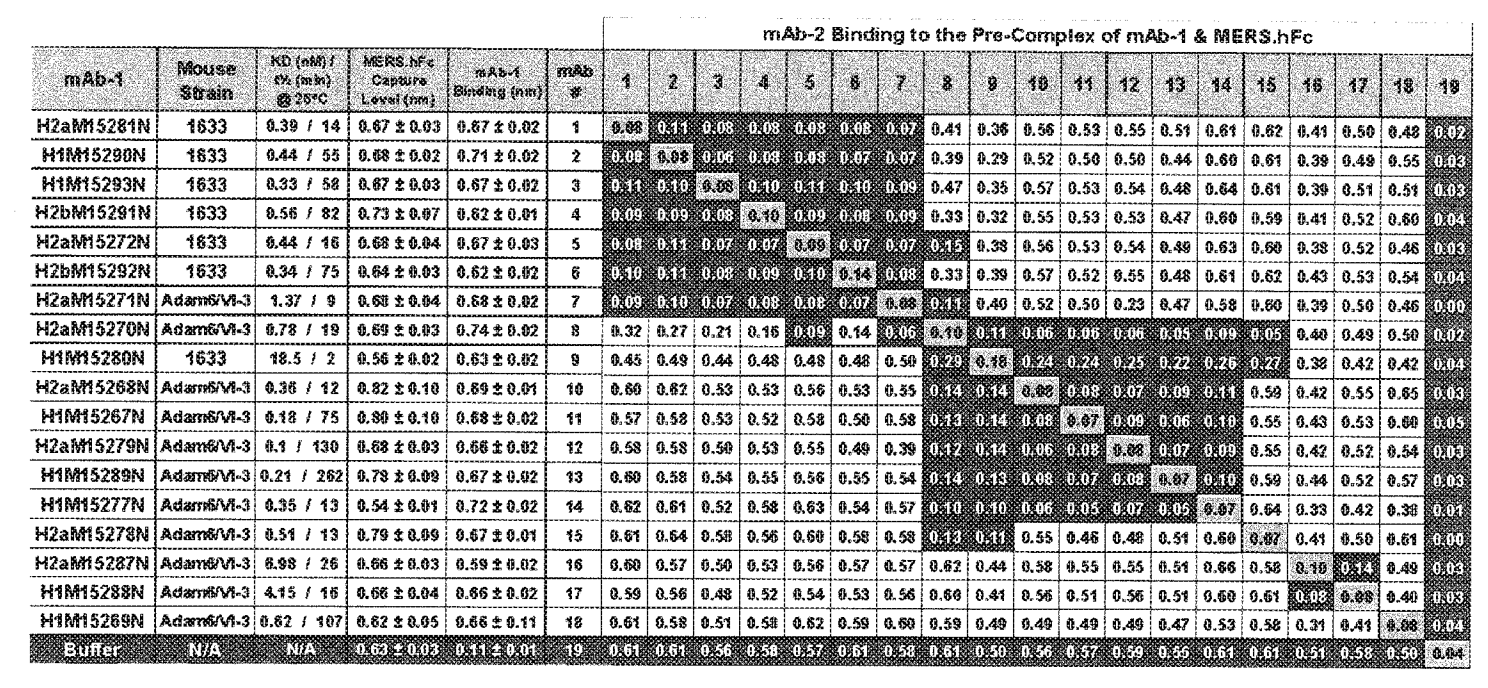

Under the experimental conditions used in this Example, cross competition (i.e., competition between antibodies in both orientations) was observed, for example, for: (a) H2aM15281N, H1M15290N, H1M15293N, and H2bM15291N; (b) H2aM15272N, H2bM15292N, and H2aM15271N; and (c) H2aM15268N, H1M15267N, H2M15279N, H1M15289N, and H1M15277N (FIG. 2).

Figure 3:
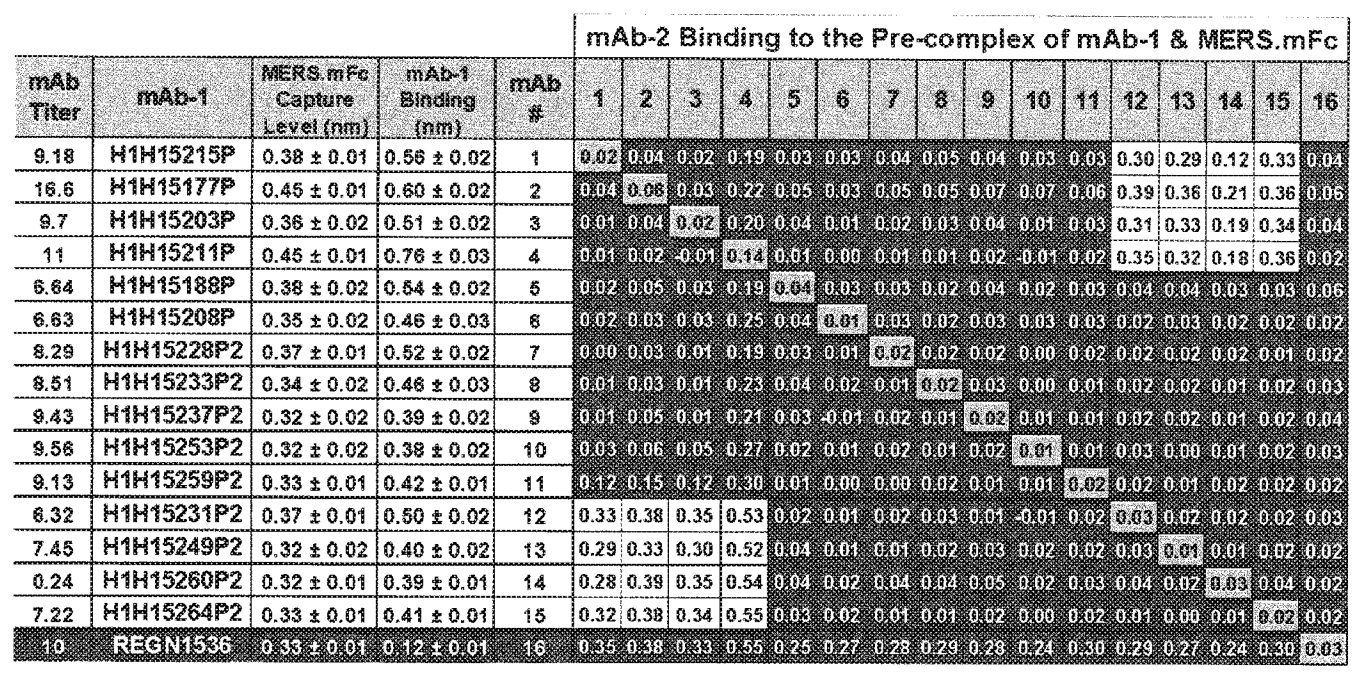

In another experiment, binding competition between selected antibodies isolated directly from antigen-positive mouse B cells (described in Example 1) was determined. Under the experimental conditions used in this Example, cross competition (i.e., competition between antibodies in both orientations) was observed, for example, for: (a) H1H15215P, H1H15177P, H1H15203P, and H1H15211P; (b) H1H15188P, H1H15208P, H1H15228P2, H1H15233P2, H1H15237P2, H1H15253P2, and H1H15259P2; and (c) H1H15231P2, H1H15249P2, H1H15260P2, and H1H15264P2 (FIG. 3).

In another experiment, the binding competition between two antibodies H1H15211P and H1H15277N was monitored.

TABLE 12

| mAb1 | mAb1 capture level (nm) | Binding of pre-complex of mAb2 and MERS-RBD-mFc to captured mAb1 | | | |
|---|---|---|---|---|---|
| | | H1H15277N | H1H15211P | Isotype control mAb | No mAb |
| H1H15277N | 2.19 | 0.22 | 0.55 | 1.03 | 0.96 |
| H1H15211P | 2.08 | 0.68 | 0.22 | 0.73 | 0.69 |

Table 12 shows that the two antibodies do not inhibit each other and that binding of one antibody to MERS-CoV RBD still allows binding of the second antibody. These data suggest that the two antibodies bind to discrete, non-overlapping epitopes. Mutation of one epitope as a result of selective pressure by one antibody should not affect binding of the other one.

Example 7: In Vivo Efficacy of Anti-MERS-CoV-S Antibodies

Materials and Methods
Generation of Human DPP4 Knockin Mice

Since the MERS spike protein does not interact with mouse DPP4, a humanized model of MERS-CoV infection was generated using VelociGene® technology (Valenzuela et al 2003, Nat. Biotechnol. 21: 652-659). Briefly, a large targeting vector (LTVEC) was constructed to contain 82 kb human DPP4 genomic DNA from exons 2 to 26 including 3' UTR to replace 79 kb mouse Dpp4 counterparts sequence. Human BAC RP11-68L22 and mouse BAC RP23-362N15 containing the Dpp4 gene were identified using Blast and sequence confirmed using Illumina bench top sequencer MiSeq. The LTVEC was electroporated in F1 hybrid (129S6SvEvTac/C57BL6NTac) ES cells. G418-resistant colonies were picked 10 days after electroporation and screened for correct targeting by the loss-of-allele assay. The VelociMouse® method was used (Poueymirou, et. al. 2007; Nature Biotechnology 25: 91-99), in which targeted ES cells were injected into un-compacted 8-cell stage Swiss Webster embryos, to produce fully ES cell-derived F0 generation mice carrying the human DPP4 gene allele. All animal procedures were carried out in strict accordance with the recommendations in the Guide for the Care and Use of Laboratory Animals of the NIH. The protocol was approved by the Regeneron Pharmaceuticals Institutional Animal Care and Use Committee (IACUC). The method is described in detail in U.S. Patent Application No. 62/051,626, filed on Sep. 17, 2014, incorporated herein in its entirety. Transgenic mice were also generated by random insertion of the hDPP4 gene in the mouse genome.

Animal Experiments

Six- to eight-week-old humanized DPP4 mice were injected intraperitoneally (i.p.) with indicated amounts of antibody or sterile saline as a control at 1 day pre-infection or 1 day post-infection, depending on the experiment. Prior to intranasal inoculation, mice were anaesthetized by intraperitoneal injection using a mix of xylazine (0.38 mg/mouse; Lloyd laboratories) and ketamine (1.3 mg/mouse; Henry Schein animal health), diluted in PBS to make a total volume of 50 µl per mouse. Once anaesthetized, mice were intranasally inoculated with either PBS or $2\times10^5$ pfu of MERS-CoV (Jordan) diluted into PBS for a total inoculum of 50 µl. During the experiment, mice were weighed prior to infection and every day of the experiment to assess MERS-CoV induced weight loss. Mice were euthanized at day 2 or day 4 post-infection using a lethal dose of isofluorane (Butler Animal Health Supply). Lungs were harvested for further analysis of MERS-CoV replication and pathology.

MERS-CoV RNA Analysis

RNA was extracted from mouse lung by homogenization in 1 ml of Trizol® (Life Technologies Inc) using a Magnalyzer (Roche) according to manufacturer's instructions. Levels of MERS-CoV RNA were assessed using the Taqman® Fast virus one-step master mix (Applied Biosystems) according to the manufacturers' instructions using a duplex of primers obtained from Life Technologies targeting a region of the genome upstream of the envelope gene (UpE); the leader sequence of the nucleocapsid messenger RNA (leader primer) and compared to mouse 18S rRNA (endogenous control). qPCR reactions in Microamp® fast optical reaction plates (Applied Biosystems) were read on a 7500 fast DX real-time PCR instrument (Applied Biosystems) and data was analyzed using the delta Ct method, with an uninfected control set to 1. Percent MERS-CoV RNA detected was expressed relative to levels of RNA detected in infected mice treated with isotype-matched control antibodies.

Plaque Assay for MERS-CoV Titers

Mouse lung was homogenized in 1 ml of PBS with glass beads for 60 seconds at 6000 rpm using a Magnalyzer (Roche). Homogenate was then centrifuged for 10 minutes at 10,000 rpm and supernatant analyzed by plaque assay on Vero E6 cells to quantitate levels of virus remaining after treatment. Plaque assays were performed as previously described, except that plates were left for 3 days for plaques to appear.

Histological Analysis

Histological slides were prepared from 5-µm sections of fixed, paraffin-embedded tissues, and stained with hematoxylin and eosin. Fields were examined by light microscopy and analyzed. The degrees of interstitial, peribronchiolar and perivascular inflammation were scored from 0 to 5. For each experimental group, the slides were blinded and scored from 0 to 5 and tabulated to compare strains, time points and treatments. Other histologic features, such as the presence of bronchiolar epithelial and alveolar damage, pleural changes and the extent of peribronchovascular inflammation, were also noted for each group in the text. The overall inflammatory scores for each mouse were averaged for each group, and presented as average scores of all mice in each group and time-point.

Results

Humanized Mice for DPP4 are Susceptible to MERS-CoV Infection

In vivo testing of anti-viral molecules requires a small animal model that is susceptible to MERS-CoV infection. Mice are not susceptible to MERS-CoV infection. Sequence comparison of the sequence of mouse and human DPP4 revealed that the amino acids that have previously been identified as contact sites between MERS-CoV S protein and its receptor differ between the two species. In addition, expression of human DPP4 in mouse cells allows for MER-Spp entry and MERS-CoV propagation, indicating that entry of the virus is the limiting step in infection of mouse cells and the lack of interaction between mouse DPP4 and the MERS-CoV glycoprotein defines the species tropism in vitro.

The inventors hypothesized that mice expressing human DPP4 in place of mouse DPP4 would be susceptible to MERS-CoV and allow for in vivo testing of anti-MERS-CoV therapeutics. VelociGene® technology was employed to replace the 79 kb of the mouse Dpp4 gene with 82 kb of its human ortholog. The resulting mice express fully human DPP4 under the control of the mouse regulatory elements, to preserve the proper expression regulation and protein tissue distribution.

To test if humanized mice and transgenic mice could support MERS-CoV infection, in one initial experiment, transgenic mice were treated intraperitoneally with 200 µg of anti-MERS-CoV-S antibodies or isotype control on day −1 and infected intranasally with MERS-CoV (~$10^6$ pfu of EMC2012) on day 0. Four days post-infection, the lungs were harvested and RNA levels of the virus were measured by RT-PCR to check the effect of the antibodies on viral load. Table 13 shows the average levels of viral genomic RNA and the replicating RNA expressed as percentage of isotype controls. Treatment with H1H15211P resulted in about 500-fold reduction of viral RNA in the infected mice.

TABLE 13

| Antibody | Genomic RNA | Replicating RNA (leader) |
|---|---|---|
| H1H15177P | 0.356839562 | 0.273565089 |
| H1H15211P | 0.254493202 | 0.206006238 |
| H4sH15211P | 1.989548316 | 1.112094283 |
| lgG1 isotype control | 104.0889287 | 101.2578723 |
| lgG4 isotype control | 100 | 100 |

Figure 5:
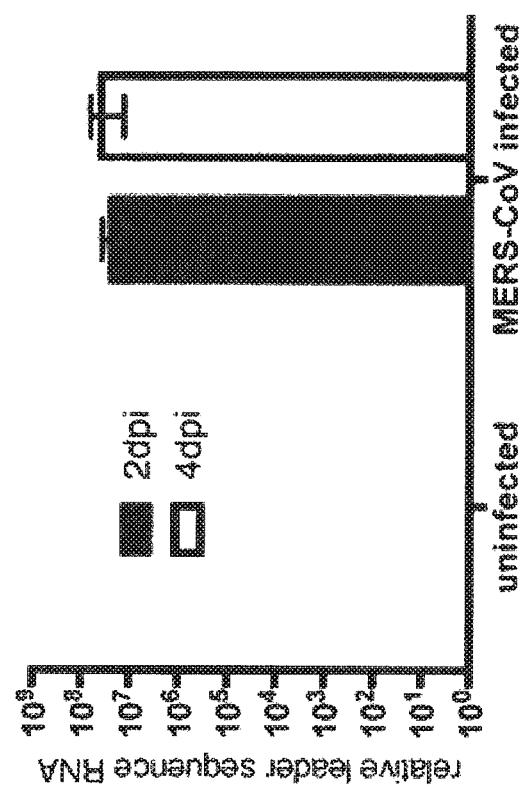
FIG. 5 shows quantitative PCR of MERS-CoV transcript (MERS-CoV genome—leader sequence) in humanized DPP4 mice at days 2 and 4 post infection.
Figure 6:
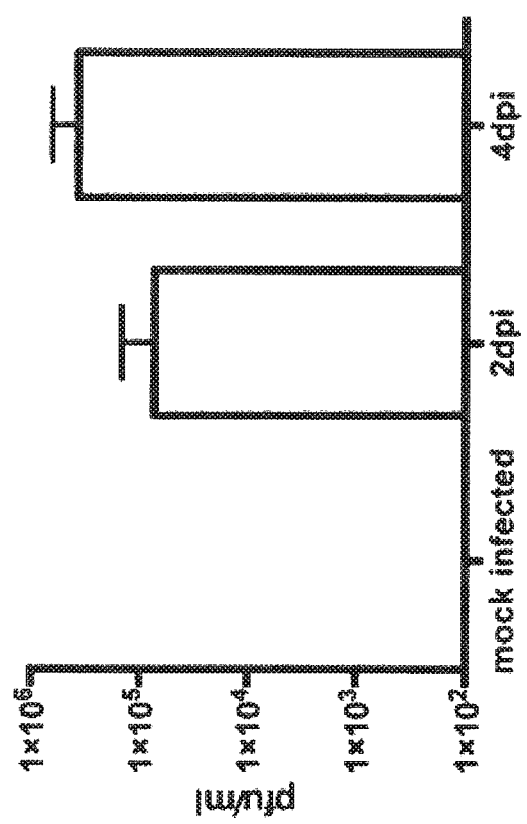
FIG. 6 shows MERS-CoV viral titer quantitation of infected mouse lung at day 4 post infection. Mouse lung MERS-CoV levels were quantified and expressed as pfu/ml of homogenized mouse lung.

In another experiment, 6 to 8 week old humanized DPP4 (huDPP4) mice were intranasally inoculated with MERS-CoV. Although no mortality or clinical signs of disease was observed up to day 4, at days 2 and 4 post-inoculation mice were euthanized and their lungs were dissected. To obtain virus RNA levels, lungs were homogenized in Trizol®, and analyzed by Realtime PCR using primers specific to MERS-CoV (FIGS. 4 and 5). To obtain virus titers, lungs were homogenized in PBS, clarified by centrifugation and titered on Vero E6 cells (FIG. 6). Robust MERS-CoV replication in the lungs was evident at 2 and 4 days post infection. RNA quantification, using a primer set specific for MERS-CoV leader, which were designed to only amplify replicating MERS-CoV, demonstrated high levels of MERS-CoV replicating RNA in lungs collected at day 2, and these levels were maintained through day 4 post infection (FIG. 5). Plaque assay of lung homogenate on Vero E6 cells quantified MERS-CoV (Jordan) levels of ~$7.27 \times 10^4$ pfu/g lung at day 2 and ~$3.75 \times 10^5$ pfu/g lung at 4 days post infection (FIG. 6), demonstrating active replication of MERS-CoV in the lungs of the huDPP4 mice. These data suggest that humanization of the receptor DPP4 using VelociGene® technology has created a robust model of MERS-CoV in mice that can be used to assess MERS-CoV treatment in vivo.

Lungs from huDPP4 mice intranasally inoculated with either MERS-CoV (Jordan strain) or PBS (mock infected) were analyzed for pathological changes. At day 2 post infection, peri-bronchiolar inflammation was evident with alterations in bronchiolar cell structure found throughout the lungs. Minimal peri-vascular inflammation or effects on alveolar structures were noted at this time point. At 4 days post infection, significant interstitial infiltration was observed with peri-vascular cuffing and extensive alveolar thickening. Bronchiolar alterations were still present as well. Importantly, this pathology is consistent with the radiographic findings of development of interstitial pneumonia and significant lung disease seen in humans with MERS-CoV, suggesting that this humanized DPP4 in vivo model of MERS-CoV infection recapitulates pathological sequelae that are seen in MERS-CoV infection of humans.

In further experiments (see below), the infected mice were administered with one or more doses of purified antibodies (as described in Example 1) or a combination of antibodies prophylactically and/or therapeutically to test their efficacy against MERS infection.

H1H15211P and H1H15277N Protect Humanized DPP4 Mice from MERS-CoV Infection

Figure 7:
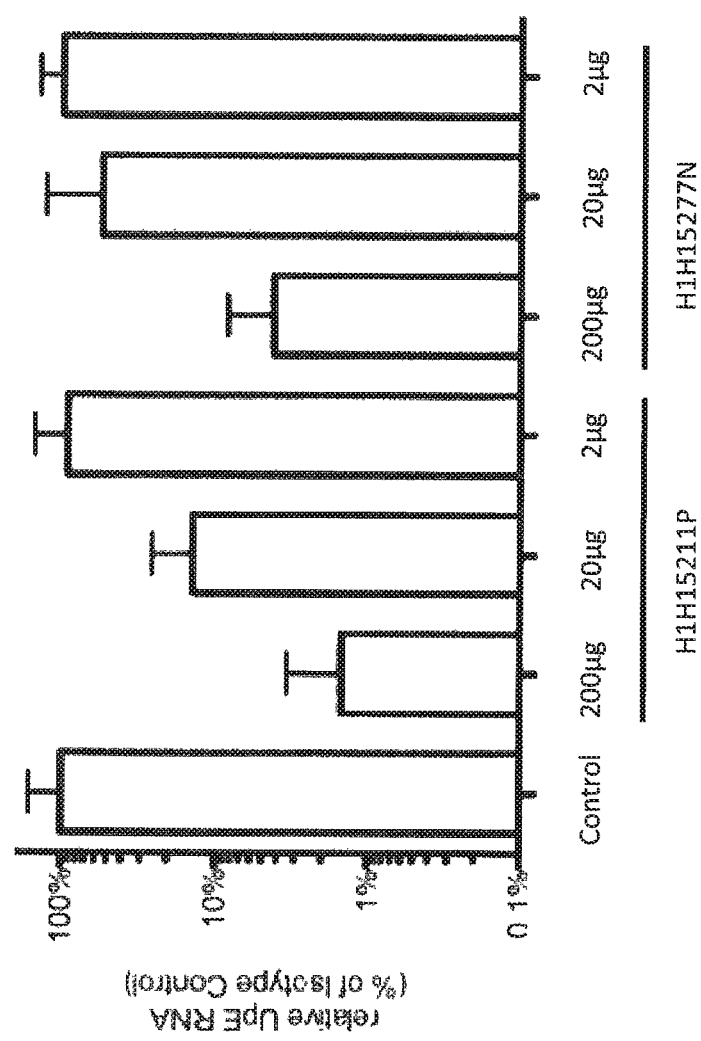
FIG. 7 shows quantitative PCR of MERS-CoV transcript (transcribed mRNA of the genome upstream of the envelope gene—UpE) from lungs of mice treated with 200 µg, 20 µg, or 2 µg of H1H15211P or H1H15277N antibodies, or with a hIgG isotype control one day before infection with MERS-CoV. All samples were compared to hIgG1 isotype control set at 100%.
Figure 8:
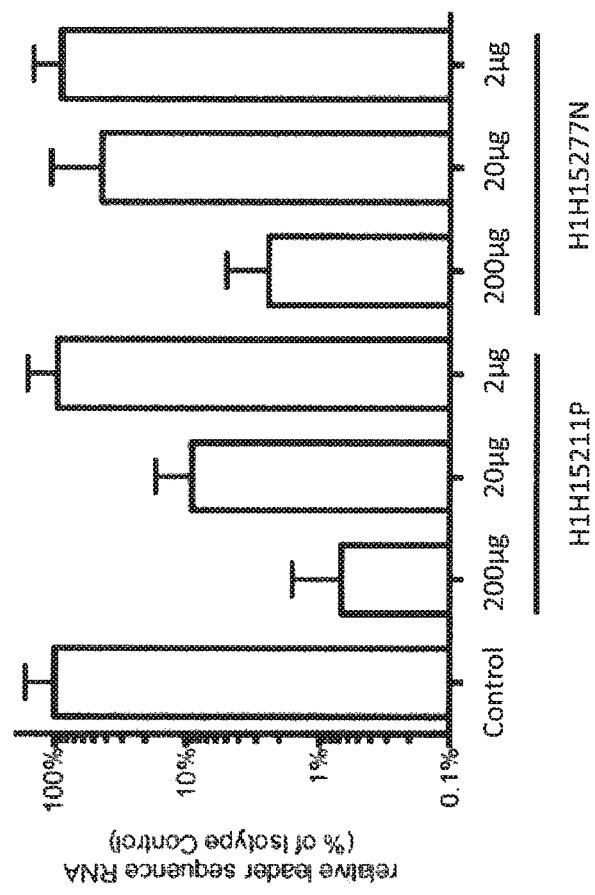
FIG. 8 shows quantitative PCR of MERS-CoV transcript (MERS-CoV genome—leader sequence) from lungs of mice treated with 200 µg, 20 µg, or 2 µg of H1H15211P or H1H15277N antibodies, or with a hIgG isotype control one day before infection with MERS-CoV. All samples were compared to hIgG1 isotype control set at 100%.
Figure 9:
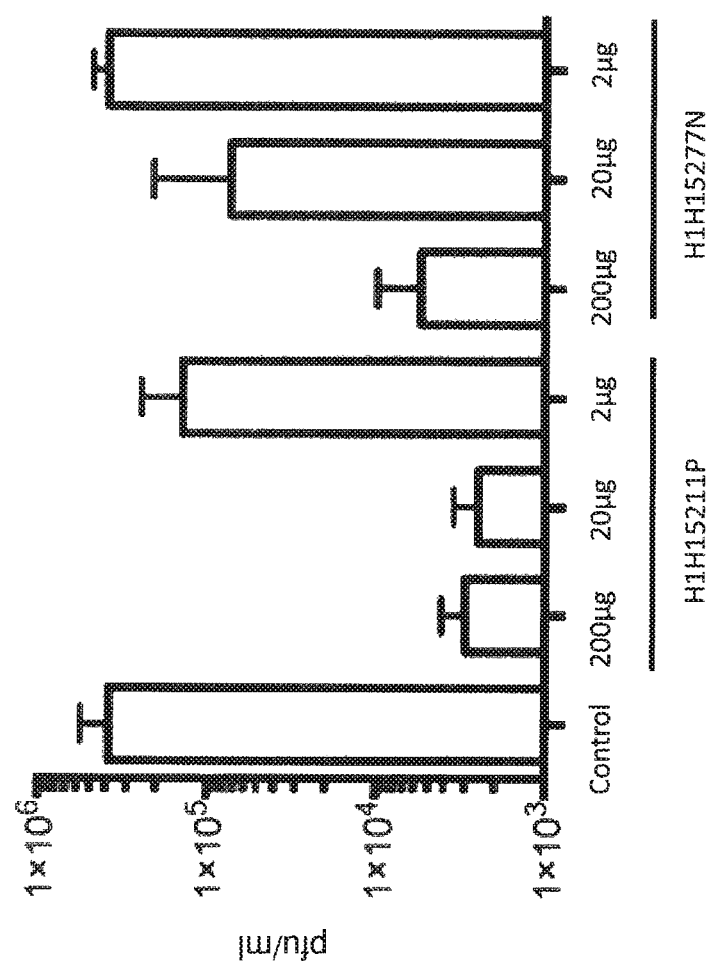
FIG. 9 shows analysis of viral titer in the lungs as quantitated by plaque assay and reported as pfu/ml from lungs of mice treated with 200 µg, 20 µg, or 2 µg of H1H15211P or H1H15277N antibodies, or with a hIgG isotype control one day before infection with MERS-CoV. All samples were compared to hIgG1 isotype control set at 100%.

Having established that humanized DPP4 mice were susceptible to MERS-CoV, this model was used to evaluate the activity of two monoclonal antibodies in vivo. Mice were i.p. injected with 200 ug, 20 ug or 2 ug of either H1H15211P, or of H1H15277N or with 200 ug of hIgG1 isotype control antibody 24 hours before intranasal infection with $1 \times 10^5$ pfu of MERS-CoV (Jordan strain). As seen in FIGS. 7 and 8, both antibodies were able to significantly decrease MERS-CoV specific RNA levels in the lungs by over 2 logs at the 200 ug per mouse dose, compared to the isotype control antibody. H1H15211P was more effective at reducing MERS-CoV RNA levels at the 20 ug dose compared to H1H15277N at the same dose. The 2 ug dosing of either antibody was ineffective at reducing viral RNA levels compared to isotype control treated mice. When MERS-CoV titer was analyzed in the lungs (FIG. 9) it was found that both the 200 ug and 20 ug dose of H1H15211P reduces virus levels to near the level of detection in the assay ($2 \times 10^3$ pfu/ml). H1H15277N is equally efficient at the 200 ug dose as H1H15211P, while the 20 ug and 2 ug display a dose dependent inhibition of viral inhibition. These data suggest that H1H15211P and H1H15277N can effectively block MERS-CoV infection in vivo.

Figure 10:
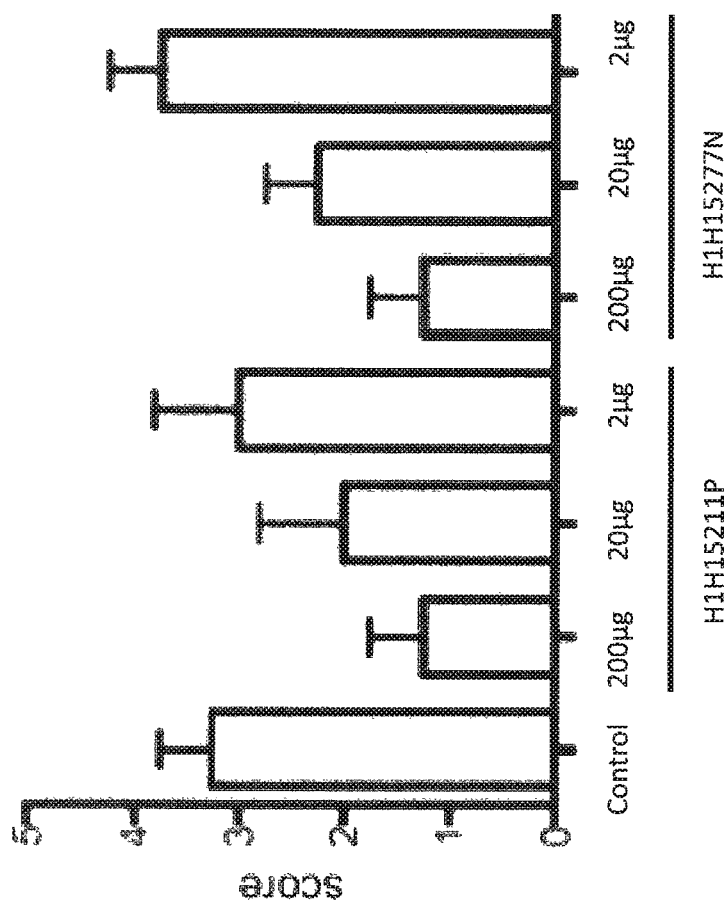
FIG. 10 shows inflammatory scores from histological analysis of the lungs of mice treated with 200 µg, 20 µg, or 2 µg of H1H15211P or H1H15277N antibodies, or with a hIgG isotype control one day before infection with MERS-CoV.

Histological analysis was also performed on lungs from mice treated 24 hours pre-infection with H1H15277N, H1H15211P or hIgG1 isotype control antibody at 4 days post infection. Lungs from mice pre-treated with hIgG isotype control mice displayed significant lung pathology with increased interstitial inflammation, perivascular cuffing, and thickening of alveolar septa. Mice treated with 200 ug of either H1H15277N or H1H15211P had reduced inflammation with minimal foci of inflammatory cells in the interstitium and minor bronchiolar cuffing. In mice pre-treated with 20 ug of H1H15277N and H1H15211P, moderate levels of perivascular cuffing and interstitial inflammation were found as compared to the higher antibody group. In contrast, the 2 ug antibody pre-treated group had similar pathology to the hIgG1 isotype control displaying significant interstitial inflammation and predominant perivascular inflammation. Blinded histological scoring (FIG. 10) reflects the reduced inflammation scores for treated mice. These findings demonstrate that H1H15277N and REGN 3051 confer a dose-dependent reduction in lung pathology following MERS-CoV infection corroborating viral RNA levels and virus titers determined for these mice.

Taken together, these data indicate that H1H15211P and H1H15277N can block MERS-CoV infection and disease in vivo when injected 1 day before infection. To our knowledge, H1H15211P and H1H15277N are the first fully-human antibodies that have been shown to display efficacy in an in vivo model of MERS-CoV infection.

H1H15211P and H1H15277N can Treat Humanized DPP4 Mice Infected with MERS-CoV

Figure 11:
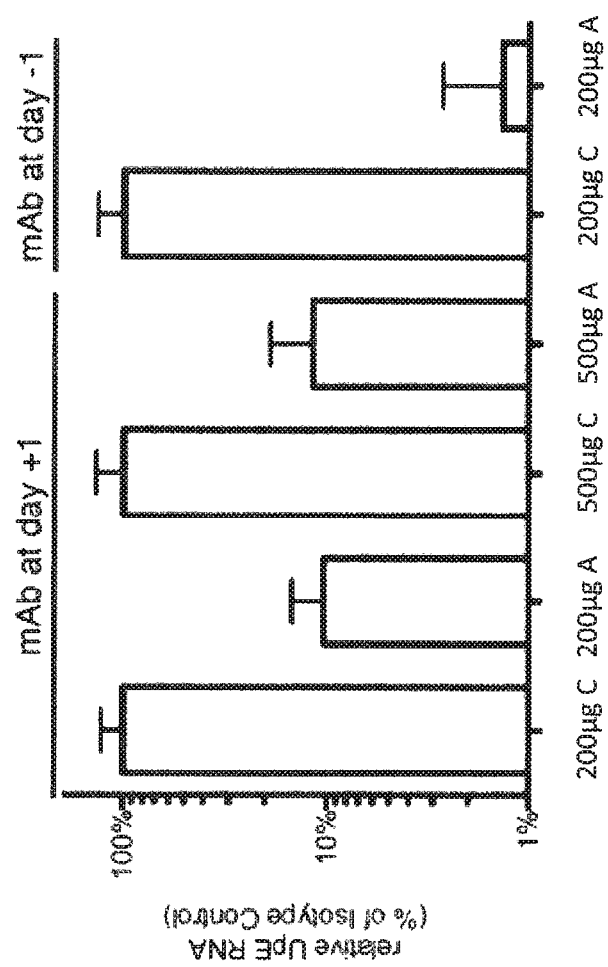
FIG. 11 shows quantitative PCR of MERS-CoV transcript (transcribed mRNA of the genome upstream of the envelope gene—UpE) from lungs of mice treated with 200 µg or 500 µg of H1H15211P or a hIgG isotype control at one day post infection or with 200 µg of H1H15211P at one day before infection with MERS-CoV. All samples were compared to hIgG1 isotype control set at 100%.
Figure 12:
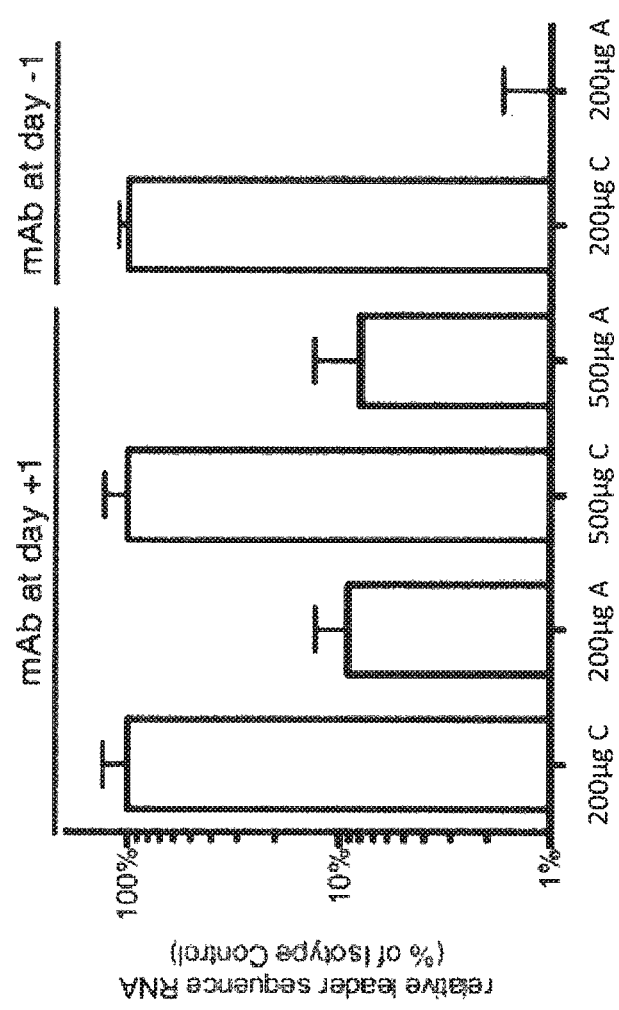
FIG. 12 shows quantitative PCR of MERS-CoV transcript (MERS-CoV genome—leader sequence) from lungs of mice treated with 200 µg or 500 µg of H1H15211P or a hIgG isotype control at one day post infection or with 200 µg of H1H15211P at one day before infection with MERS-CoV. All samples were compared to hIgG1 isotype control set at 100%.
Figure 13:
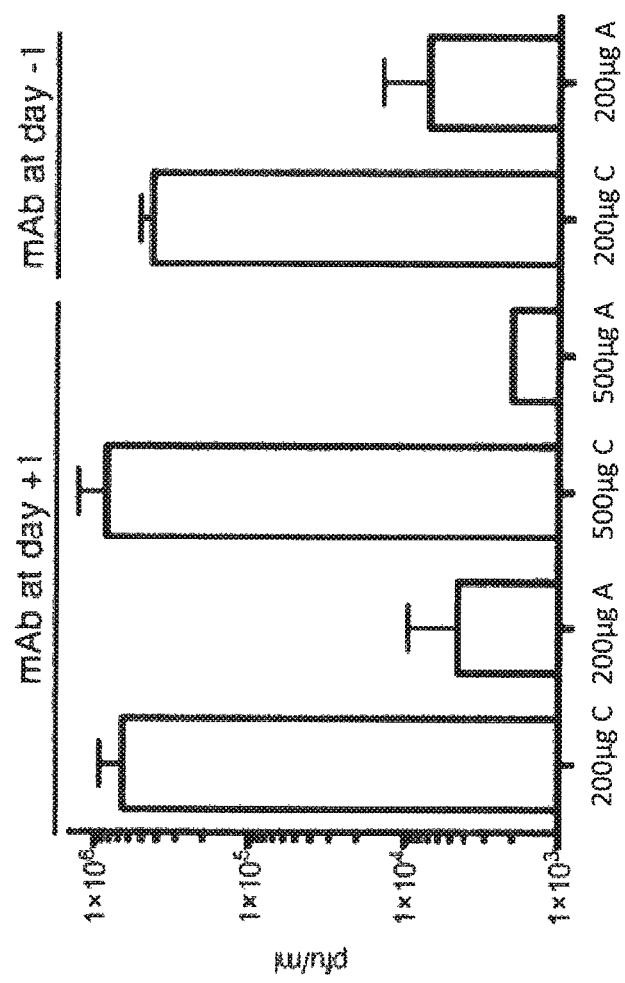
FIG. 13 shows analysis of viral titer in the lungs as quantitated by plaque assay and reported as pfu/ml from lungs of mice treated with 200 µg or 500 µg of H1H15211P or a hIgG isotype control at one day post infection or with 200 µg of H1H15211P at one day before infection with MERS-CoV. All samples were compared to hIgG1 isotype control set at 100%.

The ability to inhibit MERS-CoV replication and lung pathology after infection is a desired trait in a potential therapeutic. To assess whether H1H15211P is able have an effect therapeutically, huDPP4 mice were infected with MERS-CoV, and then 24 hours later injected i.p. with either 500 ug of hIgG isotype control or H1H15211P at 500 ug or 200 ug. At 4 days post infection mice were euthanized and mouse lungs were analyzed for viral RNA, virus titer and lung pathology. Both the 500 ug and 200 ug doses of H1H15211P were able to reduce viral RNA levels by about 10 fold in the lungs of mice compared to control antibody treated mice (FIGS. 11 and 12). Lung titers of the same mice demonstrated significant reduction in viral levels in the lungs with a greater than 2 log reduction at day 4 post infection (FIG. 13). These data demonstrate H1H15211P can significantly inhibit viral replication even when administered 24 hours following viral inoculation.

Figure 14:
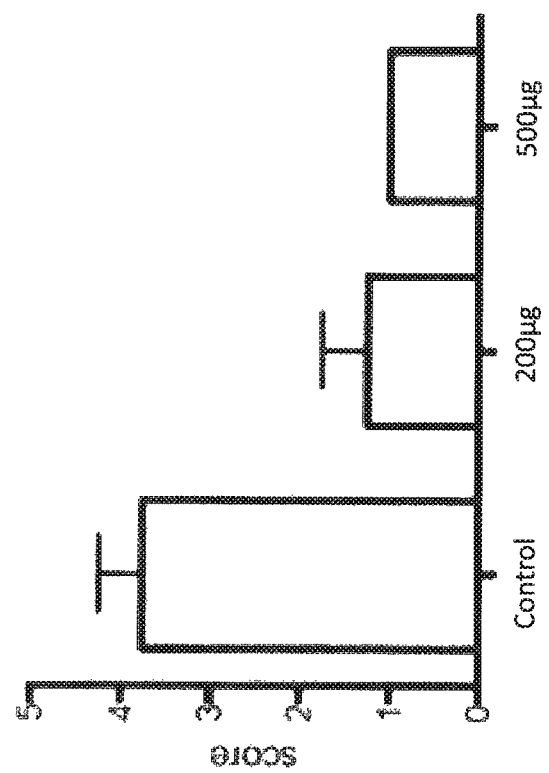
FIG. 14 shows inflammatory scores from histological analysis of the lungs of mice treated with 200 μg or 500 μg of H1H15211P or with a hIgG isotype control one day post infection with MERS-CoV.

Histological analysis was performed on mice treated 24 hours post infection with hIgG control antibody, 500 ug or 200 ug H1H15211P. Mice treated with control antibody displayed similar pathology to the control above with significant interstitial inflammation, peri-vascular cuffing and thickening of alveolar septa. Mice treated with either 200 ug or 500 ug of H1H15211P had minimal interstitial inflammation and with reduced and only focal peri-vascular inflammation throughout the lungs. Blinded histological scoring demonstrates reduced inflammation scores for treated mice (FIG. 14). These data demonstrates that therapeutic doses of H1H15211P reduce MERS-CoV induced lung pathology even when given 24 hour post-infection.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

---

What is claimed is:

1. A method of preventing, treating or ameliorating at least one symptom or indication of MERS-CoV infection, the method comprising administering a pharmaceutical composition comprising a human monoclonal antibody or antigen-binding fragment thereof that specifically binds to Middle East Respiratory Syndrome corona virus (MERS-CoV) spike protein, wherein the antibody or antigen-binding fragment comprises a HCVR/LCVR amino acid sequence pair selected from the group consisting of SEQ ID NOs: 2/10, 18/26, 34/42, 50/58, 66/74, 82/90, 98/106, 114/106, 122/106, 130/106, 138/106, 146/106, 154/162, 170/162, 178/162, 186/194, 202/210, 218/226, 234/242, 250/258, 266/274, 282/290, 298/306, 314/322, 330/338, 346/354, 362/370, 378/386, 394/402, 410/418, 426/434, and 442/450.

2. The method of claim 1, wherein the antibody has one or more of the following characteristics:
 (a) is a fully human monoclonal antibody;
 (b) interacts with one or more amino acid residues in the receptor binding domain of the MERS-CoV spike protein selected from amino acid residues 367 to 606 of SEQ ID NO: 457;
 (c) binds to MERS-CoV spike protein with a dissociation constant ($K_D$) of less than 18.5 nM, as measured in a surface plasmon resonance assay;
 (d) blocks binding of MERS-CoV spike protein to dipeptidyl peptidase 4 (DPP4) by more than 90%, as measured in a blocking ELISA assay;
 (e) neutralizes MERS-CoV infectivity of human host cells by more than 90% and with $IC_{50}$ less than 4 nM, as measured in a virus-like particle (VLP) neutralization assay;
 (f) neutralizes MERS-CoV infectivity wherein the MERS-CoV comprises an isolate of the virus selected from the group consisting of EMC/2012, Jordan-N3/2012, England-Qatar/2012, Al-Hasa_1_2013, Al-Hasa_2_2013, Al-Hasa_3_2013, Al-Hasa_4_2013, Al-Hasa_12, Al-Hasa_15, Al-Hasa_16, Al-Hasa_17, Al-Hasa_18, Al-Hasa_19, Al-Hasa_21, Al-hasa_25, Bisha_1, Buraidah_1, England 1, Hafr-Al-batin_1, Hafr-Al-Batin_2, Hafr-Al-Batin_6, Jeddah_1, KFU-HKU 1, KFU-HKU 13, Munich, Qatar3, Qatar4, Riyadh_1, Riyadh_2, Riyadh_3, Riyadh_3, Riyadh_4, Riyadh_5, Riyadh_9, Riyadh_14, Taif_1, UAE, and Wadi-Ad-Dawasir;
 (g) is a bi-specific antibody comprising a first binding specificity to a first epitope in the receptor binding domain of MERS-CoV spike protein and a second binding specificity to a second epitope in the receptor binding domain of MERS-CoV spike protein wherein the first and second epitopes are distinct and non-overlapping; and
 (h) prevents entry of MERS-CoV into a host cell.

3. The method of claim 1, wherein the at least one symptom or indication is selected from the group consisting of inflammation in the lung, alveolar damage, viral load, fever, cough, shortness of breath, pneumonia, diarrhea, organ failure, and septic shock.

4. The method of claim 3, wherein the pharmaceutical composition is administered prophylactically or therapeutically to the subject in need thereof.

5. The method of claim 4, wherein the subject is selected from the group consisting of an immunocompromised individual, an adult more than 65 years of age, a traveler to an area in the Middle East, healthcare worker, a person with a history of medical problems, a person with occupational or recreational contact with camels or bats, and a person with contact with a person(s) with confirmed or suspected MERS infection, and wherein the pharmaceutical composition is administered prophylactically to the subject.

6. The method of claim 1, wherein the pharmaceutical composition is administered in combination with a second therapeutic agent.

7. The method of claim 6, wherein the second therapeutic agent is selected from the group consisting of an anti-inflammatory drug, an anti-viral drug, a different antibody to MERS-CoV spike protein, a vaccine for MERS-CoV, antibiotics, a dietary supplement and any other palliative therapy to treat MERS infection.

8. The method of claim 1, wherein the pharmaceutical composition is administered subcutaneously, intravenously, intradermally, intraperitoneally, orally, intramuscularly or intracranially.

9. The method of claim 5, wherein the subject is a person with a history of medical problems, wherein the history of medical problems comprises heart problems, diabetes or both.

10. The method of claim 7, wherein the second therapeutic agent is an anti-inflammatory drug, wherein the anti-inflammatory drug comprises a corticosteroid, a non-steroidal anti-inflammatory drug or both.

11. The method of claim 7, wherein the second therapeutic agent is a dietary supplement, wherein the dietary supplement is an anti-oxidant.

* * * * *